United States Patent
Bright et al.

(10) Patent No.: US 11,890,393 B2
(45) Date of Patent: Feb. 6, 2024

(54) METHODS AND DEVICES FOR IN SITU FORMED NERVE CAP

(71) Applicants: Tulavi Therapeutics, Inc., Los Gatos, CA (US); Incept, LLC, Campbell, CA (US)

(72) Inventors: Corinne Bright, Mountain View, CA (US); Yong Ren, Mountain View, CA (US); Kenneth M. Martin, Mountain View, CA (US); Farhad Khosravi, Sunnyvale, CA (US); Amarpreet S. Sawhney, Lexington, MA (US)

(73) Assignees: Tulavi Therapeutics, Inc., Los Gatos, CA (US); Incept, LLC, Campbell, CA (US)

( * ) Notice: Subject to any disclaimer, the term of this patent is extended or adjusted under 35 U.S.C. 154(b) by 0 days.

(21) Appl. No.: 17/138,703

(22) Filed: Dec. 30, 2020

(65) Prior Publication Data

US 2021/0187160 A1 Jun. 24, 2021

Related U.S. Application Data

(63) Continuation of application No. PCT/US2019/040429, filed on Jul. 2, 2019.
(Continued)

(51) Int. Cl.
*A61B 17/11* (2006.01)
*A61F 2/00* (2006.01)
(Continued)

(52) U.S. Cl.
CPC .......... *A61L 27/26* (2013.01); *A61B 17/1128* (2013.01); *A61F 2/00* (2013.01);
(Continued)

(58) Field of Classification Search
None
See application file for complete search history.

(56) References Cited

U.S. PATENT DOCUMENTS 2,339,482 A 1/1944 Huttkay
2,339,846 A 1/1944 Du Bois et al.
(Continued)

FOREIGN PATENT DOCUMENTS

CA 2 351 787 A1 12/2001
CN 1682693 A 10/2005
(Continued)

OTHER PUBLICATIONS

Dimatteo et al. In situ forming injectable hydrogels for drug delivery and wound repair, Advanced Drug Delivery Reviews, 127 (Mar. 2018) pp. 167-184. (Year: 2018).*
(Continued)

*Primary Examiner* — Carlos A Azpuru
*Assistant Examiner* — Casey S Hagopian
(74) *Attorney, Agent, or Firm* — Knobbe Martens Olson & Bear, LLP

(57) ABSTRACT

Disclosed are methods, devices and materials for the in situ formation of a nerve cap to inhibit neuroma formation following planned or traumatic nerve injury. The method includes the steps of identifying a severed end of a nerve, and positioning the severed end into a cavity defined by a form. A transformable media is introduced into the form cavity to surround the severed end. The media is permitted to undergo a transformation from a first, relatively flowable state to a second, relatively non flowable state to form a protective barrier surrounding the severed end. The media may be a hydrogel, and the transformation may produce a
(Continued)

synthetic crosslinked hydrogel protective barrier. The media may include at least one anti-regeneration agent to inhibit nerve regrowth.

18 Claims, 24 Drawing Sheets

Related U.S. Application Data

(60) Provisional application No. 62/822,881, filed on Mar. 24, 2019, provisional application No. 62/692,858, filed on Jul. 2, 2018.

(51) Int. Cl.
  *A61F 2/02* (2006.01)
  *A61K 9/00* (2006.01)
  *A61L 27/52* (2006.01)
  *A61L 31/14* (2006.01)
  *A61B 17/00* (2006.01)
  *A61L 27/26* (2006.01)
  *A61L 27/18* (2006.01)

(52) U.S. Cl.
  CPC .............. *A61F 2/02* (2013.01); *A61K 9/0004* (2013.01); *A61L 27/18* (2013.01); *A61L 27/52* (2013.01); *A61L 31/14* (2013.01); *A61B 2017/00526* (2013.01); *A61F 2210/00* (2013.01); *A61F 2210/008* (2013.01); *A61F 2240/00* (2013.01); *A61F 2240/001* (2013.01); *A61F 2250/00* (2013.01); *A61L 2400/06* (2013.01); *A61L 2430/32* (2013.01)

(56) References Cited

U.S. PATENT DOCUMENTS

| | | |
|---|---|---|
| 4,029,793 A | 6/1977 | Adams et al. |
| 4,582,865 A | 4/1986 | Balazs et al. |
| 4,601,169 A | 7/1986 | Hesse et al. |
| 5,279,825 A | 1/1994 | Wehling |
| 6,152,943 A | 11/2000 | Sawhney |
| 6,165,201 A | 12/2000 | Sawhney et al. |
| 6,179,862 B1 | 1/2001 | Sawhney |
| 6,379,373 B1 | 4/2002 | Sawhney et al. |
| 6,514,534 B1 | 2/2003 | Sawhney |
| 6,545,067 B1 | 4/2003 | Büchner et al. |
| 6,566,406 B1 | 5/2003 | Pathak et al. |
| 6,605,294 B2 | 8/2003 | Sawhney |
| 6,610,713 B2 | 8/2003 | Tracey |
| 6,629,969 B2 | 10/2003 | Chan et al. |
| 6,632,457 B1 | 10/2003 | Sawhney |
| 6,673,093 B1 | 1/2004 | Sawhney |
| 6,676,675 B2 | 1/2004 | Mallapragada et al. |
| 6,689,148 B2 | 2/2004 | Sawhney et al. |
| 6,703,047 B2 | 3/2004 | Sawhney et al. |
| 6,746,464 B1 | 6/2004 | Makower |
| 6,818,018 B1 | 11/2004 | Sawhney |
| 6,887,974 B2 | 5/2005 | Pathak |
| 6,932,971 B2 | 8/2005 | Bachmann et al. |
| 6,937,896 B1 | 8/2005 | Kroll |
| 7,009,034 B2 | 3/2006 | Pathak et al. |
| 7,025,990 B2 | 4/2006 | Sawhney |
| 7,057,019 B2 | 6/2006 | Pathak |
| 7,211,651 B2 | 5/2007 | Pathak |
| 7,220,270 B2 | 5/2007 | Sawhney et al. |
| 7,332,566 B2 | 2/2008 | Pathak et al. |
| 7,347,850 B2 | 3/2008 | Sawhney |
| 7,413,752 B2 | 8/2008 | Sawhney |
| 7,592,418 B2 | 9/2009 | Pathak et al. |
| 7,597,882 B2 | 10/2009 | Pathak et al. |
| 7,605,232 B2 | 10/2009 | Pathak |
| 7,648,713 B2 | 1/2010 | Sawhney |
| 7,708,979 B2 | 5/2010 | Lowman et al. |
| 7,744,913 B2 | 6/2010 | Noyes |
| 7,772,359 B2 | 8/2010 | Pacetti |
| 7,776,063 B2 | 8/2010 | Sawhney et al. |
| 7,780,980 B2 | 8/2010 | Sawhney |
| 7,790,192 B2 | 9/2010 | Sawhney et al. |
| 7,862,538 B2 | 1/2011 | Sawhney et al. |
| 7,872,068 B2 | 1/2011 | Khosravi et al. |
| 7,914,541 B2 | 3/2011 | Sawhney et al. |
| 7,928,141 B2 | 4/2011 | Li |
| 8,003,705 B2 | 8/2011 | Sawhney et al. |
| 8,044,137 B2 | 10/2011 | Khosravi et al. |
| 8,105,622 B2 | 1/2012 | Sawhney |
| 8,175,711 B2 | 5/2012 | Demarais et al. |
| 8,206,299 B2 | 6/2012 | Foley et al. |
| 8,211,017 B2 | 7/2012 | Foley et al. |
| 8,257,723 B2 | 9/2012 | Noyes |
| 8,383,161 B2 | 2/2013 | Campbell et al. |
| 8,399,443 B2 | 3/2013 | Seward |
| 8,409,606 B2 | 4/2013 | Sawhney et al. |
| 8,465,752 B2 | 6/2013 | Seward |
| 8,470,362 B2 | 6/2013 | Sawhney et al. |
| 8,480,651 B2 | 7/2013 | Abuzaina et al. |
| 8,512,749 B2 | 8/2013 | Sawhney et al. |
| 8,535,705 B2 | 9/2013 | Pathak et al. |
| 8,557,535 B2 | 10/2013 | Pathak |
| 8,563,027 B2 | 10/2013 | Jarrett et al. |
| 8,708,995 B2 | 4/2014 | Seward et al. |
| 8,741,328 B2 | 6/2014 | Suzuki et al. |
| 8,795,709 B2 | 8/2014 | Sawhney et al. |
| 8,852,230 B2 | 10/2014 | Sawhney et al. |
| 8,852,646 B2 | 10/2014 | Campbell et al. |
| 8,916,611 B2 | 12/2014 | Roy et al. |
| 8,961,501 B2 | 2/2015 | Jarrett et al. |
| 8,986,730 B2 | 3/2015 | Sawhney et al. |
| 9,011,879 B2 | 4/2015 | Seward |
| 9,023,023 B2 | 5/2015 | McKay et al. |
| 9,125,807 B2 | 9/2015 | Sawhney et al. |
| 9,131,975 B2 | 9/2015 | McKay |
| 9,186,197 B2 | 11/2015 | McKay |
| 9,199,065 B2 | 12/2015 | Seward |
| 9,205,150 B2 | 12/2015 | Jarrett et al. |
| 9,254,267 B2 | 2/2016 | Sawhney |
| 9,308,283 B2 | 4/2016 | Campbell et al. |
| 9,358,374 B2 | 6/2016 | Dacey et al. |
| 9,370,485 B2 | 6/2016 | Sawhney et al. |
| 9,386,969 B2 | 7/2016 | Sawhney et al. |
| 9,386,990 B2 | 7/2016 | Muir et al. |
| 9,463,004 B2 | 10/2016 | Campbell et al. |
| 9,498,557 B2 | 11/2016 | Pathak et al. |
| 9,669,117 B2 | 6/2017 | Campbell et al. |
| 9,687,216 B2 | 6/2017 | Sawhney et al. |
| 9,707,000 B2 | 7/2017 | Hoke et al. |
| 9,730,986 B2 | 8/2017 | Roy et al. |
| 9,775,906 B2 | 10/2017 | Sawhney et al. |
| 9,789,161 B2 | 10/2017 | Roy et al. |
| 9,855,317 B2 | 1/2018 | Bright |
| 10,420,724 B2 | 9/2019 | Jarrett et al. |
| 10,842,494 B2 | 1/2020 | Agarwal et al. |
| 10,550,187 B2 | 2/2020 | Sawhney et al. |
| 10,675,085 B2 | 6/2020 | Clark et al. |
| 10,786,462 B2 | 9/2020 | Jarrett et al. |
| 11,154,547 B2 | 10/2021 | Bright et al. |
| 11,246,879 B2 | 2/2022 | Bright et al. |
| 11,446,359 B2 | 9/2022 | Bright |
| 2002/0037919 A1 | 3/2002 | Hunter |
| 2003/0152637 A1 | 8/2003 | Chasin et al. |
| 2004/0096507 A1 | 5/2004 | Kwang et al. |
| 2004/0166088 A1 | 8/2004 | Shalaby |
| 2004/0186488 A1 | 9/2004 | Droese |
| 2004/0220296 A1 | 11/2004 | Lowman et al. |
| 2005/0203206 A1 | 9/2005 | Trieu |
| 2005/0228460 A1 | 10/2005 | Levin et al. |
| 2005/0261672 A1 | 11/2005 | Deem et al. |
| 2006/0159823 A1* | 7/2006 | Melvik ................ A61K 31/715 426/575 |
| 2006/0177481 A1 | 8/2006 | Sawhney |
| 2006/0184185 A1 | 8/2006 | Olausson et al. |
| 2006/0280797 A1 | 12/2006 | Shoichet et al. |
| 2006/0287678 A1 | 12/2006 | Shafer |

(56) References Cited

U.S. PATENT DOCUMENTS

| | | |
|---|---|---|
| 2007/0016274 A1 | 1/2007 | Boveja et al. |
| 2007/0168044 A1 | 7/2007 | Phillips et al. |
| 2007/0253960 A1 | 11/2007 | Roy et al. |
| 2007/0255379 A1 | 11/2007 | Williams et al. |
| 2008/0114092 A1 | 5/2008 | Sawhney |
| 2008/0147137 A1 | 6/2008 | Cohen et al. |
| 2008/0319506 A1 | 12/2008 | Cauller |
| 2009/0047349 A1 | 2/2009 | Bennett et al. |
| 2010/0119451 A1 | 5/2010 | Sawhney |
| 2010/0168625 A1* | 7/2010 | Swain ............... A61B 17/11 623/23.72 |
| 2010/0255060 A1 | 10/2010 | Kajii et al. |
| 2011/0104061 A1 | 5/2011 | Seward |
| 2011/0137328 A1 | 6/2011 | Muir et al. |
| 2012/0039862 A1 | 2/2012 | Borodic |
| 2012/0049689 A1 | 3/2012 | Bennett et al. |
| 2013/0035682 A1 | 2/2013 | Weil |
| 2013/0071462 A1 | 3/2013 | Jarrett et al. |
| 2013/0204068 A1 | 8/2013 | Gnanashanmugam et al. |
| 2013/0225664 A1 | 8/2013 | Horsager et al. |
| 2013/0274674 A1 | 10/2013 | Fischell et al. |
| 2013/0287698 A1 | 10/2013 | Seward |
| 2013/0296646 A1 | 11/2013 | Barbut et al. |
| 2013/0304174 A1* | 11/2013 | Langhals ............ A61F 2/0811 623/23.76 |
| 2014/0052168 A1 | 2/2014 | Sawhney |
| 2014/0094932 A1* | 4/2014 | Deister ............... A61N 1/0558 623/23.76 |
| 2014/0221975 A1 | 8/2014 | Gnanashanmugam et al. |
| 2014/0271717 A1 | 9/2014 | Goshayeshgar et al. |
| 2014/0276590 A1 | 9/2014 | Hiller et al. |
| 2014/0336681 A1 | 11/2014 | Agarwal et al. |
| 2014/0341836 A1 | 11/2014 | Sawhney et al. |
| 2014/0350327 A1 | 11/2014 | Poon et al. |
| 2014/0363382 A1 | 12/2014 | Campbell et al. |
| 2014/0363498 A1 | 12/2014 | Sawhney et al. |
| 2015/0065945 A1 | 3/2015 | Zarins et al. |
| 2015/0132409 A1 | 5/2015 | Stein et al. |
| 2015/0305799 A1 | 10/2015 | Trieu |
| 2015/0367033 A1 | 12/2015 | Brown et al. |
| 2015/0374887 A1 | 12/2015 | Romero-Ortega et al. |
| 2016/0045602 A1 | 2/2016 | Jarrett et al. |
| 2016/0106587 A1 | 4/2016 | Jarrett et al. |
| 2016/0166504 A1 | 6/2016 | Jarrett et al. |
| 2016/0166733 A1 | 6/2016 | Phillips et al. |
| 2016/0296623 A1 | 10/2016 | Sawhney et al. |
| 2016/0331738 A1 | 11/2016 | Jarrett et al. |
| 2016/0367235 A1 | 12/2016 | Campbell et al. |
| 2017/0020729 A1 | 1/2017 | Jarrett et al. |
| 2017/0143409 A1 | 5/2017 | Clark et al. |
| 2017/0266324 A1 | 9/2017 | Campbell et al. |
| 2018/0147260 A1 | 5/2018 | Bright |
| 2018/0185390 A1 | 7/2018 | Eviston et al. |
| 2019/0038646 A1 | 2/2019 | Bright et al. |
| 2019/0216899 A1 | 7/2019 | Bright |
| 2019/0381144 A1 | 12/2019 | Friel |
| 2020/0085809 A1 | 3/2020 | Bright et al. |
| 2020/0206365 A1 | 7/2020 | Campbell et al. |
| 2020/0206366 A1 | 7/2020 | Campbell et al. |
| 2020/0206367 A1 | 7/2020 | Campbell et al. |
| 2020/0207860 A1 | 7/2020 | Sawhney et al. |
| 2021/0046221 A1 | 2/2021 | Deister |
| 2021/0205501 A1 | 7/2021 | Bright |
| 2021/0268271 A1 | 9/2021 | Bright |
| 2021/0315587 A1 | 10/2021 | Bright et al. |
| 2021/0361292 A1 | 11/2021 | Bright et al. |
| 2022/0054705 A1 | 2/2022 | Bright et al. |
| 2022/0096711 A1 | 3/2022 | Bright et al. |
| 2022/0280497 A1 | 9/2022 | Bright et al. |
| 2022/0370345 A1 | 11/2022 | Bright |
| 2022/0409902 A1 | 12/2022 | Bright |

FOREIGN PATENT DOCUMENTS

| | | | |
|---|---|---|---|
| CN | 102125516 A | 7/2011 | |
| CN | 103385850 A | 11/2013 | |
| CN | 103750919 A | 4/2014 | |
| CN | 103816111 A | 5/2014 | |
| CN | 104069485 A | 10/2014 | |
| CN | 104288091 A | 1/2015 | |
| CN | 104399131 A | 3/2015 | |
| CN | 105963792 | 9/2016 | |
| CN | 109395165 A | 3/2019 | |
| EP | 18163397.5 | 3/2018 | |
| EP | 3 581 175 | 12/2019 | |
| JP | 2000-139976 | 5/2000 | |
| JP | 5453776 B2 | 3/2014 | |
| RU | 2582226 C1 | 4/2016 | |
| WO | WO 2001/089526 | 11/2001 | |
| WO | WO 2004/002449 | 1/2004 | |
| WO | WO-2009117127 A2 * | 9/2009 | ......... A61B 17/1128 |
| WO | WO 2009/132153 | 10/2009 | |
| WO | WO 2009/146030 | 12/2009 | |
| WO | WO 2011/085166 | 7/2011 | |
| WO | WO 2012/075337 A2 | 6/2012 | |
| WO | WO-2013082590 A1 * | 6/2013 | ........... A61K 31/343 |
| WO | WO 2013/165714 | 11/2013 | |
| WO | WO 2014/130419 | 8/2014 | |
| WO | WO 2014/138085 | 9/2014 | |
| WO | WO 2016/019000 | 4/2016 | |
| WO | WO 2016/144166 | 9/2016 | |
| WO | WO-2016144166 A1 * | 9/2016 | ............. A61B 90/08 |
| WO | WO 2016/168669 | 10/2016 | |
| WO | WO 2016/176333 | 11/2016 | |
| WO | WO 2017/139487 | 8/2017 | |
| WO | WO 2018/005848 | 1/2018 | |
| WO | WO 2018/022838 | 2/2018 | |
| WO | WO 2018/125822 A2 | 7/2018 | |
| WO | WO 2018/232145 | 12/2018 | |
| WO | WO 2019/027272 | 2/2019 | |
| WO | WO 2019/178564 | 9/2019 | |
| WO | WO 2019/180208 | 9/2019 | |
| WO | WO 2019/206998 | 10/2019 | |
| WO | WO 2020/010123 | 1/2020 | |
| WO | WO 2020/010164 | 1/2020 | |
| WO | WO 2021/112772 | 6/2021 | |
| WO | WO 2021/146330 | 7/2021 | |
| WO | WO 2023/288218 | 1/2023 | |

OTHER PUBLICATIONS

Wang et al. Engineering interconnected 3D vascular networks in hydrogels using molded sodium alginate lattice as the sacrificial template, Lab Chip, 2014, 14, pp. 2709-2716. (Year: 2014).*

DuraSeal® Xact Spinal Sealant System. Integra LifeSciences Corp. Accessed online on Jan. 19, 2023 at <https://integralife.eu>. (Year: 2023).*

Yan et al. Mechanisms of Nerve Capping Technique in Prevention of painful Neuroma Formation, PLoS One, Apr. 4, 2014, 9(4), pp. 1-11. (Year: 2014).*

Barton et al. Nerve repair: toward a sutureless approach, Neurosurg Rev (2014) 37:585-595. (Year: 2014).*

Abbott, O. A., W. A. Hopkins, et al. (1950). "Therapeutic status of pulmonary autonomic nerve surgery." J Thorac Surg 20(4): 571-83; passim.

Abdi, Salahadin, et al. "A new and easy technique to block the stellate ganglion." Pain Physician 7.3 (2004): 327-332.

Adar, R., A. Kurchin, et al. (1977). "Palmar hyperhidrosis and its surgical treatment: a report of 100 cases." Ann Surg 186(1): 34-41.

Albers, James, et al. "Interventions for preventing neuropathy caused by cisplatin and related compounds." Cochrane Database Syst Rev 1.1 (2007).

Antila, H., and O. Kirvelä. "Neurolytic thoracic paravertebral block in cancer pain." Acta anaesthesiologica scandinavica 42.5 (1998): 581-585.

Antolak SJ, et al. "Therapeutic Pudendal Nerve Blocks Using Corticosteriods Cure Pelvic Pain after Failure of Sacral Neuromodulation" Pain Medicine 2009, vol. 10, No. 1, pp. 185-189.

(56) References Cited

OTHER PUBLICATIONS

B Braun Plexus Anaesthesia product guide (2014) in 10 pages.
Baumgartner, F. J. (2008). "Surgical approaches and techniques in the management of severe hyperhidrosis." Thorac Surg Clin 18(2): 167-81.
Baumgartner, Fritz J., et al. "Thoracoscopic sympathicotomy for disabling palmar hyperhidrosis: a prospective randomized comparison between two levels." The Annals of thoracic surgery 92.6 (2011): 2015-2019.
BD PuraMatrix Peptide Hydrogel Brochure (2004) in 4 pages.
Blades, B., E. J. Beattie, Jr., et al. (1950). "The surgical treatment of intractable asthma." J Thorac Surg 20(4): 584-91; passim.
Boezaart, André P. Atlas of peripheral nerve blocks and anatomy for orthopaedic anesthesia. Elsevier Health Sciences, p. 218, 2008.
Bolderman et al., International Journal of Cardiology, 2011, 149, p. 341-346 (Year: 2011).
Cai, "Injectable glycosaminoglycan hydrogels for controlled release of human basic fibroblast growth factor" Biomaterials 26 (2005) 6054-6067 (Year: 2005).
Carli, Mirjana, et al. "Tph2 gene deletion enhances amphetamine-induced hypermotility: effect of 5-HT restoration and role of striatal noradrenaline release." Journal of neurochemistry 135.4 (2015): 674-685.
Carr, D. and H. Chandler (1948). "Dorsal sympathetic ganglionectomy for intractable asthma." J Thorac Surg 17(1): 1-12.
Chaibundit, Chiraphon, et al. "Effect of ethanol on the gelation of aqueous solutions of Pluronic F127." Journal of colloid and interface science 351.1 (2010): 190-196.
Chaibundit, Chiraphon, et al. "Effect of Ethanol on the Micellization and Gelation of Pluronic P123." Langmuir 24.21 (2008): 12260-12266.
Chang, Jason Y., Kevin D. Phelan, and Janet A. Chavis. "Neurotoxicity of 25-OH-cholesterol on sympathetic neurons." Brain research bulletin 45.6 (1998): 615-622.
Cheema, S., J. Richardson, and P. McGurgan. "Factors affecting the spread of bupivacaine in the adult thoracic paravertebral space." Anaesthesia 58.7 (2003): 684-687.
Cressman, Erik NK, and David A. Jahangir. "Dual mode single agent thermochemical ablation by simultaneous release of heat energy and acid: hydrolysis of electrophiles." International Journal of Hyperthermia 29.1 (2013): 71-78.
Cunningham, D. J. (1913). Cunningham's Textbook of Anatomy, William Wood (648-734).
Da Rocha, R. P., A. Vengjer, et al. (2002). "Size of the collateral intercostal artery in adults: anatomical considerations in relation to thoracocentesis and thoracoscopy." Surg Radiol Anat 24(1): 23-6.
Denby, Christine, et al. "Temporary sympathectomy in chronic refractory angina: a randomised, double-blind, placebo-controlled trial." British journal of pain 9.3 (2015): 142-148.
Dimitrov-Szokodi, D., G. Balogh, et al. (1957). "Lung denervation in the therapy of intractable bronchial asthma." J Thorac Surg 33(2): 166-84.
Downing, S. Evans, and John C. Lee. "Nervous control of the pulmonary circulation." Annual Review of Physiology 42.1 (1980): 199-210.
Drott, C. and G. Claes (1996). "Hyperhidrosis treated by thoracoscopic sympathicotomy." Cardiovasc Surg 4(6): 788-90; discussion 790-1.
Dumont, Pascal. "Side effects and complications of surgery for hyperhidrosis." Thoracic surgery clinics 18.2 (2008): 193-207.
Dun, N. J., and A. G. Karczmar. "Evidence for a presynaptic inhibitory action of 5-hydroxytryptamine in a mammalian sympathetic ganglion." Journal of Pharmacology and Experimental Therapeutics 217.3 (1981): 714-718.
Evicore. Clinical Guidelines. Aug. 11, 2017. [Retrieved Sep. 3, 2019] Retrieved from online URL: https://www.evicore.corn/-/media/files/evicore/clinical-guidelines/solut1on /m sk-advance/archive/cmm-207---oain-eoidural-adhesiolvsiseffOB1117 102118.pdf.
Feinberg, Samuel M. "Progress in Asthma: Literature for 1934 and 1935." Journal of Allergy 7.3 (1936): 268-294.

Finucane 2017, "complications of regional anesthesia" published by Springer, 2017 p. 213.
Fredman, B., E. Zohar, et al. (2000). "Video-assisted transthoracic sympathectomy in the treatment of primary hyperhidrosis: friend or foe?" Surg Laparosc Endosc Percutan Tech 10(4): 226-9.
Freeman, N. E., R. H. Smithwick, et al. (1934). "Adrenal Secretion in Man." Am. J. Physiol. 107(3): 529.
http://www.fziomed.com/core-science/ web page last updated Aug. 19, 2016 in 2 pages.
Garcia-Morales, Luis et al., "Intraoperative Surgical Sealant Application during Cardia Defect Repair", Texas Heart Institute Journal, vol. 41, No. 4, Aug. 1, 2014, pp. 440-442.
Gay, L. N. and W. M. Reinhoff (1934). "Further Observations on the Treatment of Intractable Bronchial Asthma by Bilateral Resection of the Pulmonary Plexus." J. Allergy 13(6): 626-631.
Gloor et al., J Clin Invest., 1983, 71(5), p. 1457-1466 (Year: 1983).
Gossot, D., H. Kabiri, et al. (2001). "Early complications of thoracic endoscopic sympathectomy: a prospective study of 940 procedures." Ann Thorac Surg 71(4): 1116-9.
Gossot, D., L. Toledo, et al. (1997). "Thoracoscopic sympathectomy for upper limb hyperhidrosis: looking for the right operation." Ann Thorac Surg 64(4): 975-8.
Haam, Seokjin, et al. "An anatomical study of the relationship between the sympathetic trunk and intercostal veins of the third and fourth intercostal spaces during thoracoscopy." Clinical Anatomy 23.6 (2010): 702-706.
Hayakawa, Kazuhiro, et al. "Nerve growth factor prevention of aged-rat sympathetic neuron injury by cisplatin, vincristine and taxol-in vitro explant study." Neuroscience letters 274.2 (1999): 103-106.
Hsu, C. P., C. Y. Chen, et al. (1998). "Resympathectomy for palmar and axillary hyperhidrosis." Br J Surg 85(11): 1504-5.
Huang, B., et al. "[Therapeutic feasibility of percutaneous puncture and chemical neurolysis of thoracic sympathetic nerve block in palmar hyperhidrosis under the guidance of computed tomograph]." Zhonghua yi xue za zhi 91.38 (2011): 2710-2713.
Illfeld, et al. "Ultrasound-guided Percutaneous Peripheral Nerve Stimulation for Analgesia Following Total Knee Arthroplsaty: a Prospective Feasibility Study" Journal of Orthopaedic Surgery and Research 2017, vol. 12, No. 4, pp. 1-9.
Imrich, Richard, et al. "Functional effects of cardiac sympathetic denervation in neurogenic orthostatic hypotension." Parkinsonism & related disorders 15.2 (2009): 122-127.
International Preliminary Report on Patentability in co-pending Application No. PCT/US2019/040429, dated Jan. 5, 2021, in 7 pages.
International Search Report and Written Opinion in co-pending Application No. PCT/US2019/40429, dated Oct. 25, 2019 in 18 pages.
Ireland, S. J., and C. C. Jordan. "Pharmacological characterization of 5-hydroxytryptamine-induced hyperpolarization of the rat superior cervical ganglion." British journal of pharmacology 92.2 (1987): 417-427.
Ischemia. Wikipedia. Dec. 24, 2017. [Retrieved Sep. 3, 2019] Retrieved from online URL:https://en.wikipedia.org/w/index.php?title=Ischemia&oldid=816854406.
Karmakar, M. K., T. Gin, and AM-H. Ho. "Ipsilateral thoracolumbar anaesthesia and paravertebral spread after low thoracic paravertebral injection." British journal of anaesthesia 87.2 (2001): 312-316.
Kaur, Gurjinder, et al. "Estrogen regulation of neurotrophin expression in sympathetic neurons and vascular targets." Brain research 1139 (2007): 6-14.
Kimura, Tomohiko, Toshitake Shimamura, and Susumu Satoh. "Effects of pirenzepine and hexamethonium on adrenal catecholamine release in responses to endogenous and exogenous acetylcholine in anesthetized dogs." Journal of cardiovascular pharmacology 20.6 (1992): 870-874.
Klodell, Charles T., et al. "Oximetry-derived perfusion index for intraoperative identification of successful thoracic sympathectomy." The Annals of thoracic surgery 80.2 (2005): 467-470.
Koyama et al., Circ. J., 2002, 66, p. 645-648 (Year: 2002).

(56) References Cited

OTHER PUBLICATIONS

Krediet, Annelot C., et al. "Different Approaches to Ultrasound-guided Thoracic Paravertebral BlockAn Illustrated Review." The Journal of the American Society of Anesthesiologists 123.2 (2015): 459-474.

Lee, Ju Young, et al. "In vivo efficacy of paclitaxel-loaded injectable in situ-forming gel against subcutaneous tumor growth." International journal of pharmaceutics 392.1 (2010): 51-56.

Lee, Sang Beom, et al. "Morphometric Study of the Upper Thoracic Sympathetic Ganglia." Journal of Korean Neurosurgical Society 50.1 (2011): 30-35.

Levin, G. L. (1935). "The Treatment of Bronchial Asthma by Dorsal Sympathectomy: Direct and Indirect." Ann Surg 102(2): 161-70.

Li, et al. "Controlled Release of Protein from Biodegradable Mutio-Senstitive Injectable Poly (etherurethane) Hydrogel" ACS Appl. Mater. Interfaces 2014, vol. 6, No. 5, pp. 3640-3647.

Lin K L et al. "DuraSeal as a Ligature in the Anastomosis of rat Sciatic Nerve Gap Injury", Journal of Surgical Research, Academic Press Inc. San Diego CA US, vol. 161, No. 1, Jun. 1, 2010, pp. 101-110.

Lin, Zhiqiang, et al. "Novel thermo-sensitive hydrogel system with paclitaxel nanocrystals: High drug-loading sustained drug release and extended local retention guaranteeing better efficacy and lower toxicity." Journal of Controlled Release 174 (2014): 161-170.

Liu, et al, 2009, European J of Cariothoracic Surgery, 35, 398-402.

Macaya, D., and M. Spector. "Injectable hydrogel materials for spinal cord regeneration: a review." Biomedical materials 7.1 (2012): 012001.

Mahajan, Mohit, P. Utreja, and S. K. Jain. "Paclitaxel Loaded Nanoliposomes in Thermosensitive Hydrogel: A Dual Approach for Sustained and Localized Delivery." Anti-cancer agents in medicinal chemistry (2015).

Malik, Tariq. "Ultrasound-Guided Paravertebral Neurolytic Block: A Report of Two Cases." Pain Practice 14.4 (2014): 346-349.

Marinescu, Mark A., et al. "Coronary microvascular dysfunction, microvascular angina, and treatment strategies." JACC: Cardiovascular Imaging 8.2 (2015): 210-220.

Matchett, Gerald. "Intercostal Nerve Block and Neurolysis for Intractable Cancer Pain." Journal of Pain & Palliative Care Pharmacotherapy (2016): 1-4.

Mehdizadeh, Mohammadreza, and Jian Yang. "Design strategies and applications of tissue bioadhesives." Macromolecular bioscience 13.3 (2013): 271-288.

Microstimulation. Wikipedia. Jun. 30, 2016. [Retrieved Sep. 3, 2019) Retrieved from online URL:https://en.wikipedia.org/w/index.php?title=Microstimulation&oldid=727594711.

Moawad, H. M. M., and H. Jain. "Development of nano-macroporous soda-lime phosphofluorosilicate bioactive glass and glass-ceramics." Journal of Materials Science: Materials in Medicine 20.7 (2009): 1409-1418.

Murray, Gary L., and Joseph Colombo. "Ranolazine preserves and improves left ventricular ejection fraction and autonomic measures when added to guideline-driven therapy in chronic heart failure." Heart International 9.2 (2014): 66-73.

Naja, M. Z., et al. "Varying anatomical injection points within the thoracic paravertebral space: effect on spread of solution and nerve blockade." Anaesthesia 59.5 (2004): 459-463.

Ng, Ivan, and Tseng-Tsai Yeo. "Palmar hyperhidrosis: intraoperative monitoring with laser Doppler blood flow as a guide for success after endoscopic thoracic sympathectomy." Neurosurgery 52.1 (2003): 127-131.

Nunn, J. F., and G. Slavin. "Posterior intercostal nerve block for pain relief after cholecystectomy anatomical basis and efficacy." British journal of anaesthesia 52.3 (1980): 253-260.

Oblasti primeneniya protivospacchnogo gelya Mezogel [online] Nov. 27, 2010 retrieved on Aug. 2, 2016 from URL: http://www.mesogel.ru/prod/mesogel4.htm>.

Ostermann Pa et al. "The ligament system of the spleen and its significance for surgical interventions" Langenbecks Arch Chir 1987;371 (3):207-16, abstract.

Pai, et al, "Spleen Anatomy" (Medscape, 2014, p. 1-6). (Year: 2014).

Pandin, Pierre, Samia Rettab, and Alphonse Lubansu. "Ultrasound Guidance is Helpful for Paravertebral Block Performance and Catheter Placement in Patients with Laminectomy after Thoracotomy or Lumbotomy: A Case Series Imaging Study." (2013).

Paredi, P. and P. J. Barnes (2009). "The airway vasculature: recent advances and clinical implications." Thorax 64(5): 444-50.

Parlato, Matthew, et al. "Adaptable poly (ethylene glycol) microspheres capable of mixed-mode degradation." Acta biomaterialia 9.12 (2013): 9270-9280.

Phillips, E. W. and W. J. M. Scott (1929). "The Surgical Treatment of Bronchial Asthma." Arch Surg. 19(6): 1425-1456.

Pierce, Nathan E. et al, "Hydrogel sutureless facial nerve repair: Pilot Clinical Investigation: Sutureless Facial Nerve Repair", The Laryngoscope, Jun. 2015. vol. 125, No. 6, First Published, Dec. 4, 2014, pp. 1456-1459.

Ponce Gonzalez, M. A., G. J. Serda , et al. (2005). "Long-term pulmonary function after thoracic sympathectomy." The Journal of Thoracic and Cardiovascular Surgery 129(6): 1379-1382.

Richardson and Lonnqvist, (1998) "Thoracic Paravertebral Block" British Journal of Anaesthesia 81: 230-238.

Rienhoff WF Jr, G. L. (1938). "Treatment of Intractable Bronchial Asthma by Bilateral Resection of the Posterior Pulmonary Plexus." Arch Surg. 37(3): 456-469.

Riquet, M. (2007). "Bronchial arteries and lymphatics of the lung." Thorac Surg Clin 17(4): 619-38, viii.

Robinson, Eric A., et al. "Estimating sympathetic tone by recording subcutaneous nerve activity in ambulatory dogs." Journal of cardiovascular electrophysiology 26.1 (2015): 70-78.

Rongen, Gerard A., et al. "Presynaptic inhibition of norepinephrine release from sympathetic nerve endings by endogenous adenosine." Hypertension 27.4 (1996): 933-938.

Rosas-Ballina, et al., "Cholingergic control of inflammation" *J. Intern Med.* Jun. 2009; 265(6): 663-679.

Shvaichak E. Zavisimost vyazkosti vodnogo rastvora gialuronovoi kisloty ot ee mikrostruktury. Chast 1. Rossysky zhurnal biomekhaniki, tom 7, No. 3: 87-98, 2003.

Singh, Narendra K., and Doo Sung Lee. "In situ gelling pH-and temperature-sensitive biodegradable block copolymer hydrogels for drug delivery." Journal of Controlled Release 193 (2014): 214-227.

Takatori, Mayumi, Yoshihiro Kuroda, and Munetaka Hirose. "Local anesthetics suppress nerve growth factor-mediated neurite outgrowth by inhibition of tyrosine kinase activity of TrkA." Anesthesia & Analgesia 102.2 (2006): 462-467.

Vallieres, E. (2007). "The costovertebral angle." Thorac Surg Clin 17(4): 503-10.

Van der Velden, Vincent HJ, and Anthon R. Hulsmann. "Autonomic innervation of human airways: structure, function, and pathophysiology in asthma." Neuroimmunomodulation 6.3 (1999): 145-159.

Van Maanen, et al., "The cholinergic anti-inflammatory pathway: towards innovative treatment of rheumatoid arthritis" (Nature Reviews, Rheumatology, 5, Apr. 2009, 229-232) (Year: 2009).

Vanaclocha, V., N. Saiz-Sapena, et al. (2000). "Uniportal endoscopic superior thoracic sympathectomy." Neurosurgery 46(4): 924-8.

Vida, Gergely, et al., "α7-Cholinergic Receptor Mediates Vagal Induction of Splenic Norepinephrine", *J Immunol* 2011; 186:4340-4346; Prepublished online Feb. 21, 2011.

Vida, Gergely, et al., "β2-Adrenoreceptors of regulatory lymphocytes are essential for vagal neuromodulcation of the innate immune system", The FASEB Journal, vol. 25, Dec. 2011, pp. 4476-4485.

Wallace D G et al., "A tissue sealant based on reactive multifunctional polyenthylene glycol", Journal of BioMedical Materials Research, Wiley, New York, NY US. vol. 58, No. 5, Apr. 25, 2015 pp. 545-555.

Wang, Peizong, et al. "Antinociceptive effect of intrathecal amiloride on neuropathic pain in rats." Neuroscience letters 604 (2015): 24-29.

Wang, William et al.: "Clinical efficacy of epicardial application of drug-releasing hydrogels to prevent postoperative atrial fibrillation", Journal of thoracic and Cardiovascular Surgery, vol. 151, No. 1, First read: Apr. 25, 2015, pp. 80-85.

(56) References Cited

OTHER PUBLICATIONS

Weksler et al, 2008, Thorac Surg Clin, 18, 183-191.
Westerlund, Taina, Ville Vuorinen, and Matias Röyttä. "The perineurium modifies the effects of phenol and glycerol in rat sciatic nerve." Acta neuropathologica 108.4 (2004): 319-331.
Wilensky, H. M. (1940). "Peri-Sympathetic Injection Treatment of Asthma." Can Med Assoc J 43(1): 59-62.
Xu, Xian, et al. "Hyaluronic acid-based hydrogels: from a natural polysaccharide to complex networks." Soft matter 8.12 (2012): 3280-3294.
Yahagi, Naoki, Tsuyoshi Akiyama, and Toji Yamazaki. "Effects of ω-conotoxin GVIA on cardiac sympathetic nerve function." Journal of the autonomic nervous system 68.1 (1998): 43-48.
Yamazaki, Toji, Tsuyoshi Akiyama, and Toru Kawada. "Effects of ouabain on in situ cardiac sympathetic nerve endings." Neurochemistry international 35.6 (1999): 439-445.
Yohn, Samantha E., et al. "Not all antidepressants are created equal: differential effects of monoamine uptake inhibitors on effort-related choice behavior." Neuropsychopharmacology (2015).
Zarse, Markus, et al. "Selective increase of cardiac neuronal sympathetic tone: a catheter-based access to modulate left ventricular contractility." Journal of the American College of Cardiology 46.7 (2005): 1354-1359.
Zhang, Hongling, and Javier Cuevas. "Sigma Receptors Inhibit High-Voltage-Activated Calcium Channels in Rat Sympathetic and Parasympathetic Neurons." Journal of neurophysiology 87.6 (2002): 2867-2879.
Zhao, Ying-Zheng, et al. "Using NGF heparin-poloxamer thermosensitive hydrogels to enhance the nerve regeneration for spinal cord injury." Acta biomaterialia 29 (2016): 71-80.
Kopecek, "Peptide-directed self assembly of hydrogels" Acta Biomater. Mar. 2009; 5(3): 805-816 (Year: 2009).
Sudoh, "Tricyclic antidepressants as long-acting local anesthetics" Pain 103 (2003) 49-55 (Year: 2003).
Ajijola, "Bilateral Cardiac Sympathetic Denervation for the Management of Electrical Storm" JACC, 2012; 59(1): 91-92.
Ajijola, "Remodeling of stellate ganglion neurons after spatially targeted myocardial infarction: neuropeptide and morphologic changes" Heart Rhythm, 2015; 12(5), 1027-1035.
Collura, "Left cardiac sympathetic denervation for the treatment of long QT syndrome and catecholaminergic polymorphic ventricular tachycardia using video-assisted thoracic surgery" Heart Rhythm, 2009; 6: 752-59.
Fernandez, "Adrenergic and Cholinergic Plasticity in Heart Failure" Circulation Research, 2015; 116: 1639-1642.
Fukuda, "Cardiac Innervation and Sudden Cardiac Death" Circulation Research, 2015; 116: 2005-2019.
Ripplinger, "The nervous heart" Progress in Biophysics and Molecular Biology, 2016; 120:199-209.
Schlaich, "Sympathetic Augmentation in Hypertension Role of Nerve Firing, Norepinephrine Reuptake, and Angiotensin Neuromodulation" Hypertension, 2004; 43: 169-175.
Schwartz, "Prevention of Sudden Cardiac Death After a First Myocardial Infarction by Pharmacologic or Surgical Antiadrenergic Interventions" J. Cardiovasc Electrophysiol, 1992; 3: 2-16.
Shen, "Role of the Autonomic Nervous System in Modulating Cardiac Arrhythmias" Circulation Research, 2014; 114: 1004-1021.
Vaseghi, "Cardiac sympathetic denervation in patients with refractory ventricular arrhythmias or electrical storm: Intermediate and long-term follow-up" Heart Rhythm, 2014; 11: 360-366.
Gou, Malin, et al., "Polymeric matrix for drug delivery: Honokiol-loaded PCL-PEG-PCL nanoparticles in PEG-PCL-PEG thermosensitive hydrogel," *J Biomed Mater Res A.*, 2010, vol. 93, No. 1, pp. 219-226. < DOI: 10.1002/jbm.a.32546> Abstract; p. 220, col. 1—p. 221, col. 2; Table 1; Fig. 4.
Kabiri, Maryam, et al., "A stimulus-responsive, in situ-forming, nanoparticle-laden hydrogel for ocular drug delivery," *Drug Delivery and Translational Research*, 2018, vol. 8, pp. 484-495. <doi: 10.1007/s13346-018-0504-x> Abstract; p. 486, col. 1—p. 488, col. 1; p. 493.
Kehoe, S., et al. "FDA approved guidance conduits and wraps for peripheral nerve injury: A review of materials and efficacy", Injury, vol. 43, No. 5, May 1, 2012, pp. 553-572 (2012).
Küçüktürkmen, Berrin, et al., "In Situ Hydrogel Formulation for Intra-Articular Application of Diclofenac Sodium-Loaded Polymeric Nanoparticles," *Turk J Pharm Sci*, 2017, col. 14, No. 1, pp. 56-64. <doi: 10.4274/tjps.84803> p. 57, col. 2—p. 59, col. 1; Table 2; p. 59, col. 2; p. 60, col. 2; Figs 2-4.
"Plane definition" accessed online at https://www.cuemath.com/geometry/plane-definition/ on May 9, 2022 in 4 pages.
Ridderström et al., "Brilliant blue G treatment facilities regernation after optic nerve injury in the adult rat", Neuroreport, 2014, 25(17), pp. 1405-1410 in 6 pages.
Tan "Injectable, Biodegradable Hydrogels for Tissue Engineering Applications" Materials 2010, 3, 1746-1767 (Year: 2010).
Yin, Na, et al., "Intra-articular injection of indomethacin/methotrexate in situ hydrogel for the synergistic treatment of rheumatoid arthritis," *J. Mater. Chem. B*, 2020, vol. 8, pp. 993-1007. <DOI: 10.1039/c9tb01795j> Abstract; p. 995, col. 1; p. 996; p. 998, p. 1000, col. 1, Figs. 4, 8.
Andersen et al., "3D Cell Culture in Alginate Hydrogels", Microarrays, dated 2015, 4, pp. 133-161.
Chester et al., "Long-term benefits of stellate ganglion block in severe chronic refractory angina," Pain, 2000, 87, p. 103-105. (dated Year 2000).
Clark et al., "Self-Assembling Semiconducting Polymers;Rods and Gels from Electronic Materials", American Chemical Society, dated 2013, vol. 7, No. 2, pp. 962-977.
Gordon et al., Electrical Stimulation to Enhance Axon Regeneration After Peripheral Nerve Injuries in Animal Models and Humans', Neurotherapeutics. Dated 2016, vol. 13, No. 2, pp. 295-310.
Han et al., "Self-Assembling Peptide-Based Hydrogels in Angiogenesis", International Journal of Nanomedicine, dated 2020, pp. 10257-10269.
Moradi et al., "BD PuraMatrix Peptide Hydrogel as a Culture System for Human Fetal Schwann Cells in Spinal Cord Regeneration", Journal of Neuroscience Research, dated 2012, vol. 90, pp. 2335-2348.
Palakurthy et al., "Unusual Neurotoxicity Associated With Amiodarone Therapy," Arch. Intern. Med., 1987, 147, p. 881-884. (dated Year: 1987).
Smith, Adam Eugene, "Self-Assembly and Gold Nanoparticle Cross-Linking of Stimuliresponsive Block Copolymers Synthesized bt Reversible Addition-Fragmentation Chain Transfer Polymerization", The University of Southern Mississippi, The Aquila Digital Community, Dissertation, dated Spring May 2010, pp. 165.
Uchida et al., "Current Progress in Cross-Linked Peptide Self-Assemblies", International Journal of Molecular Sciences, dated 2020, vol. 21, No. 7577, pp. 17.
Varga, Melinda, "Self-Assembly of Nanobiomaterials", Fabrication and Self-Assembly of Nanobiomaterials, dated 2016, Ch. 3, pp. 57-90.
VWR.com, "Corning® PuraMatrix™ Peptide Hydrogel", https://us.vwr.com/store/product/20094082/corning-puramatrixtm-peptide-hydrogel#, dated Nov. 1, 2022, pp. 3.
Wei et al., "Self-crosslinking assemblies with tunable nanostructures from photoresponsive polypeptoid-based block copolymers", Polymer Chemistry, dated 2020, vol. 11, pp. 337-343.
Wu et al., "Recent Advances in the Solution Self-Assembly of Amphiphilic "Rod-Coil" Copolymers", Journal of Polymer Science, Polymer Chemistry, dated 2017, vol. 55, pp. 1459-1477.
Yang, Wenjing et al., "Electrostatic self-assembly of pFe3O4 nanoparticles on graphene oxide: A co-dispersed nanosystem reinforces PLLA scaffolds", Journal of Advanced Research, dated 2020, vol. 24, pp. 191-203.

\* cited by examiner

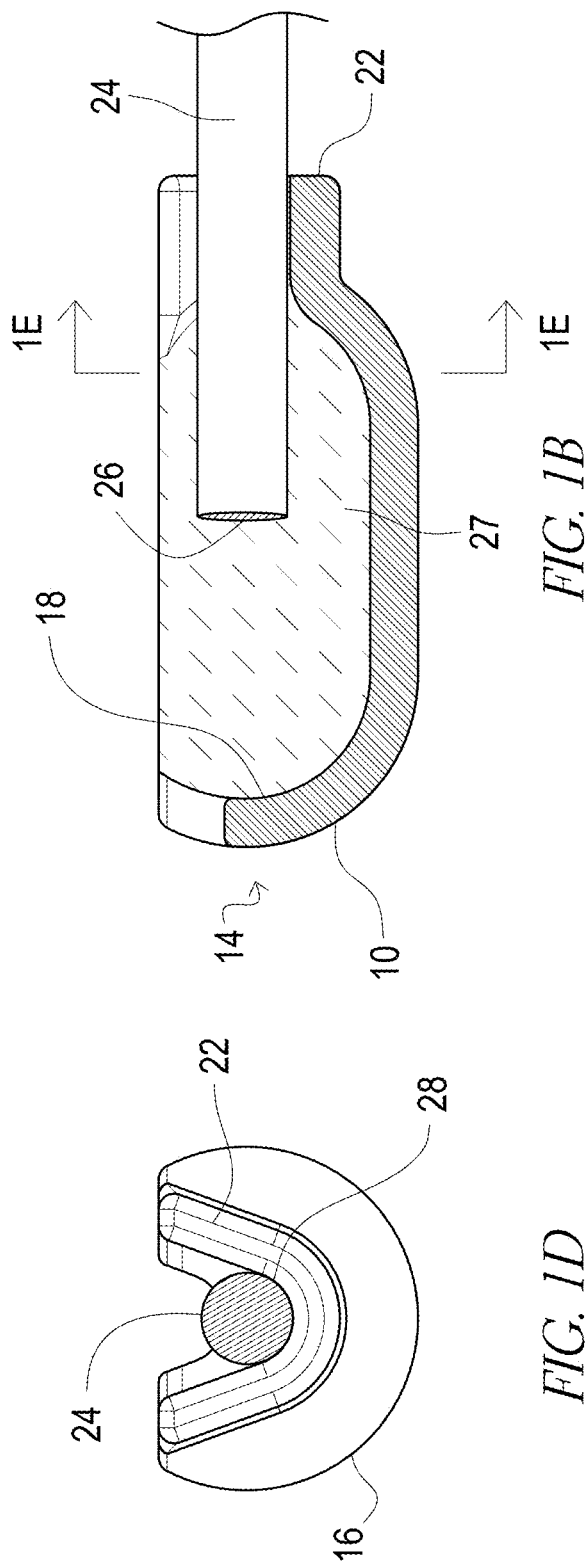

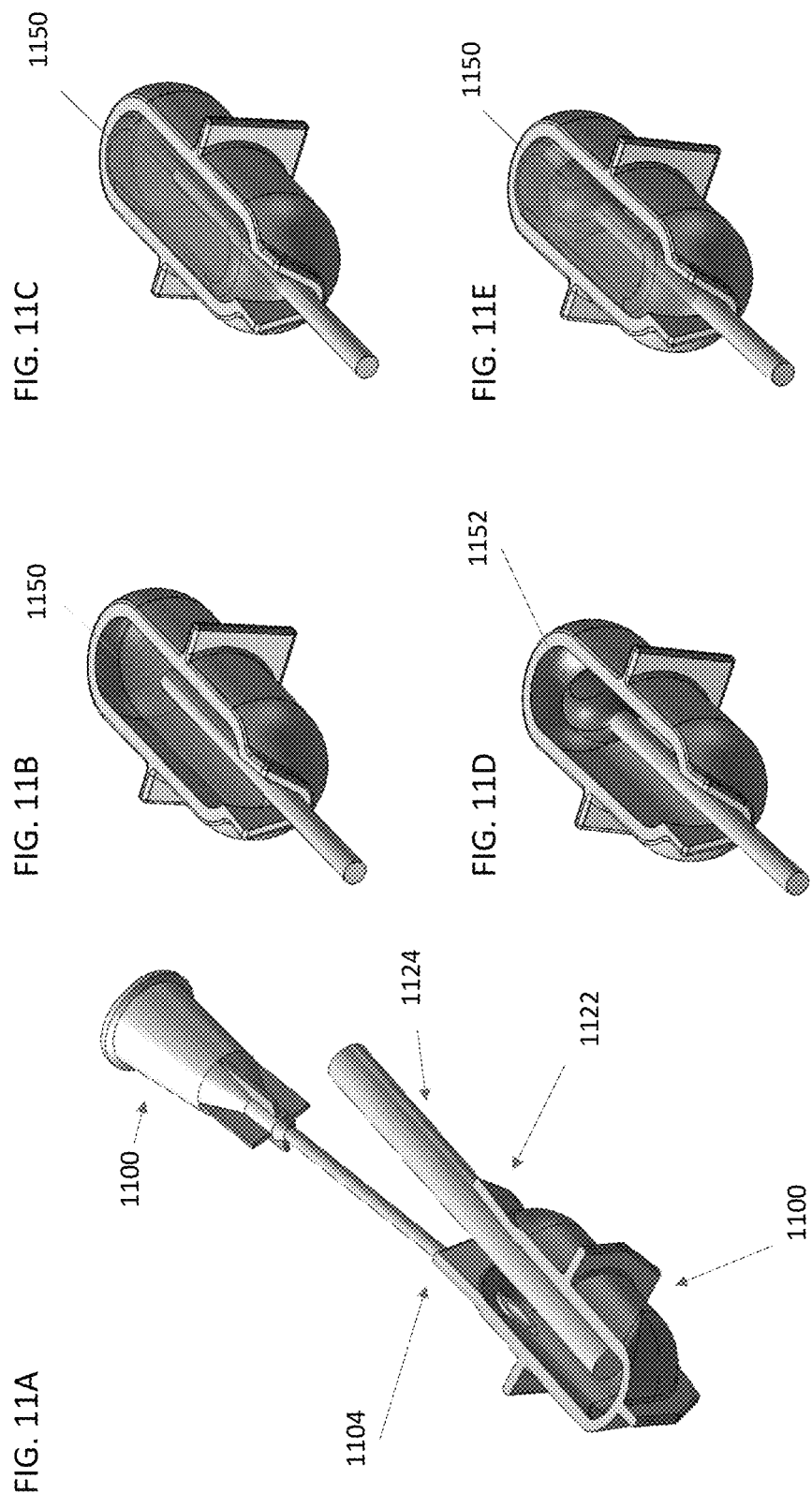

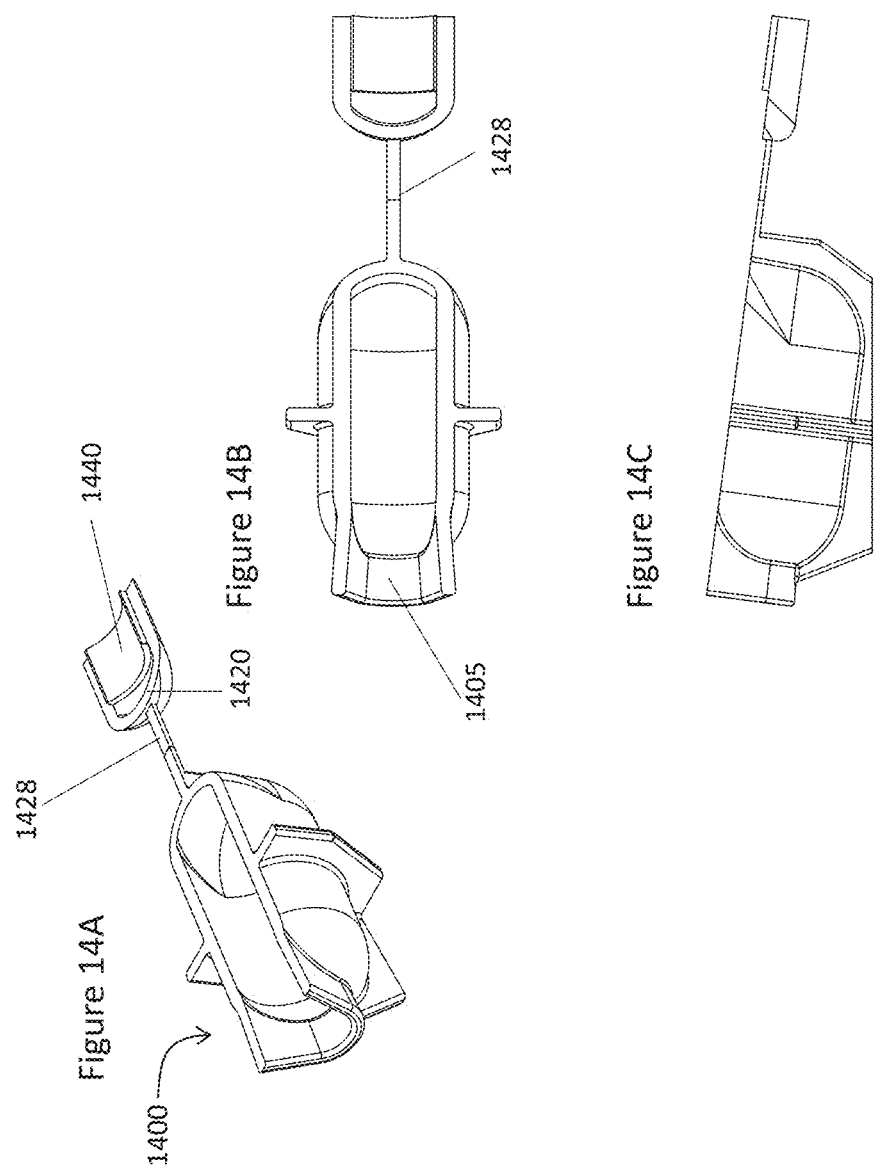

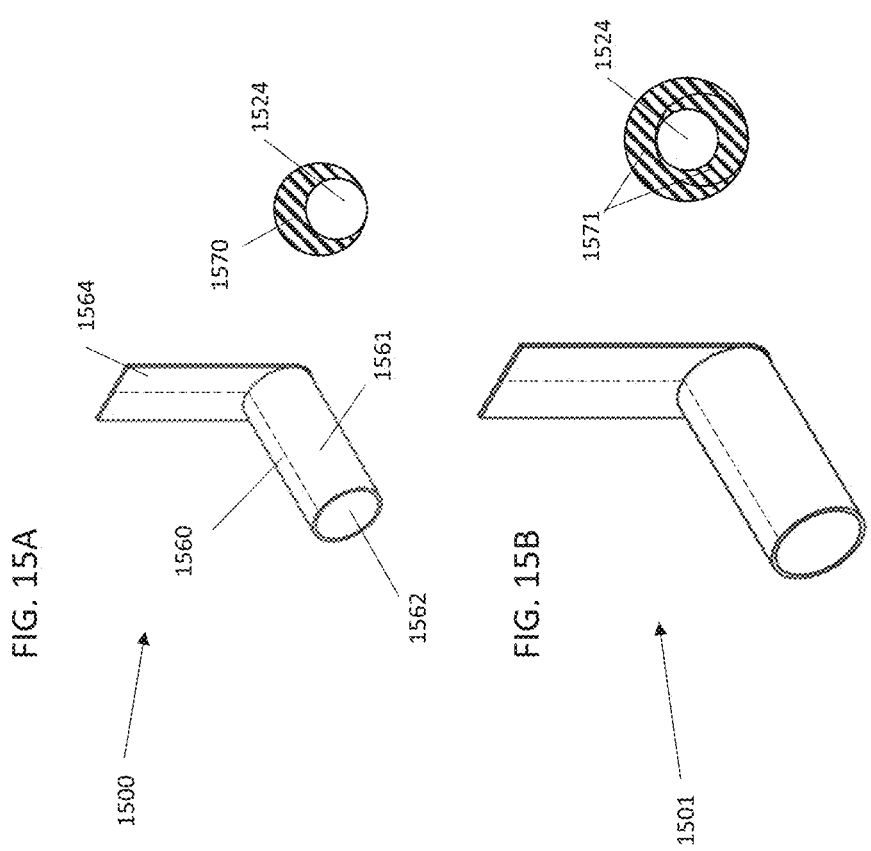

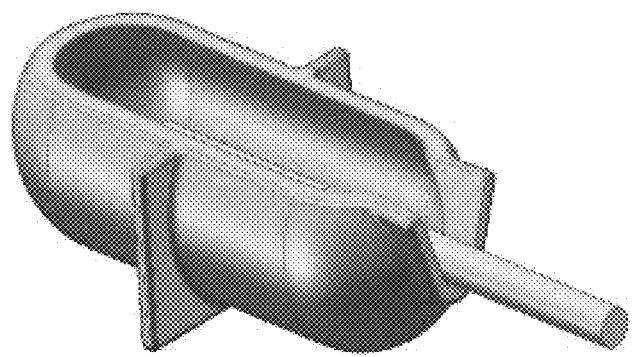
FIG. 16Ai
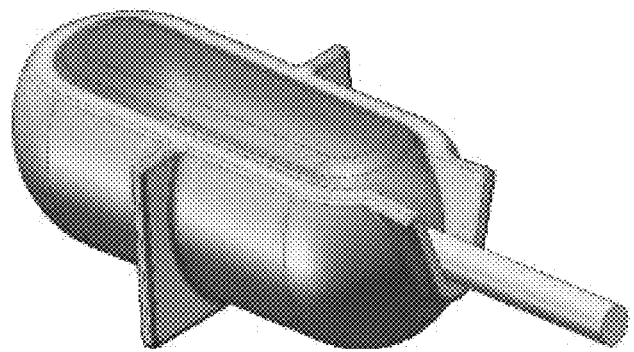
FIG. 16Aii
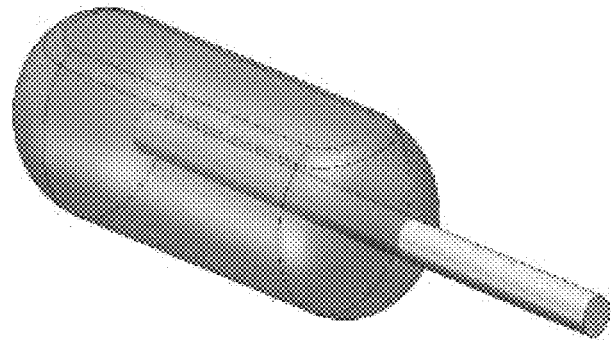
FIG. 16Aiii

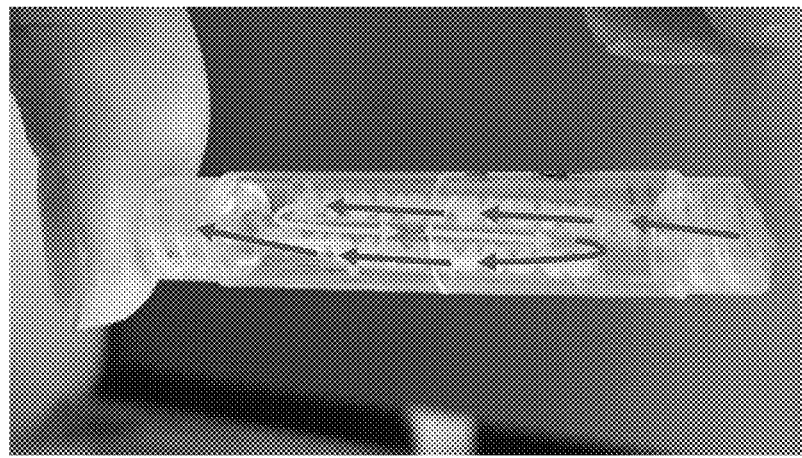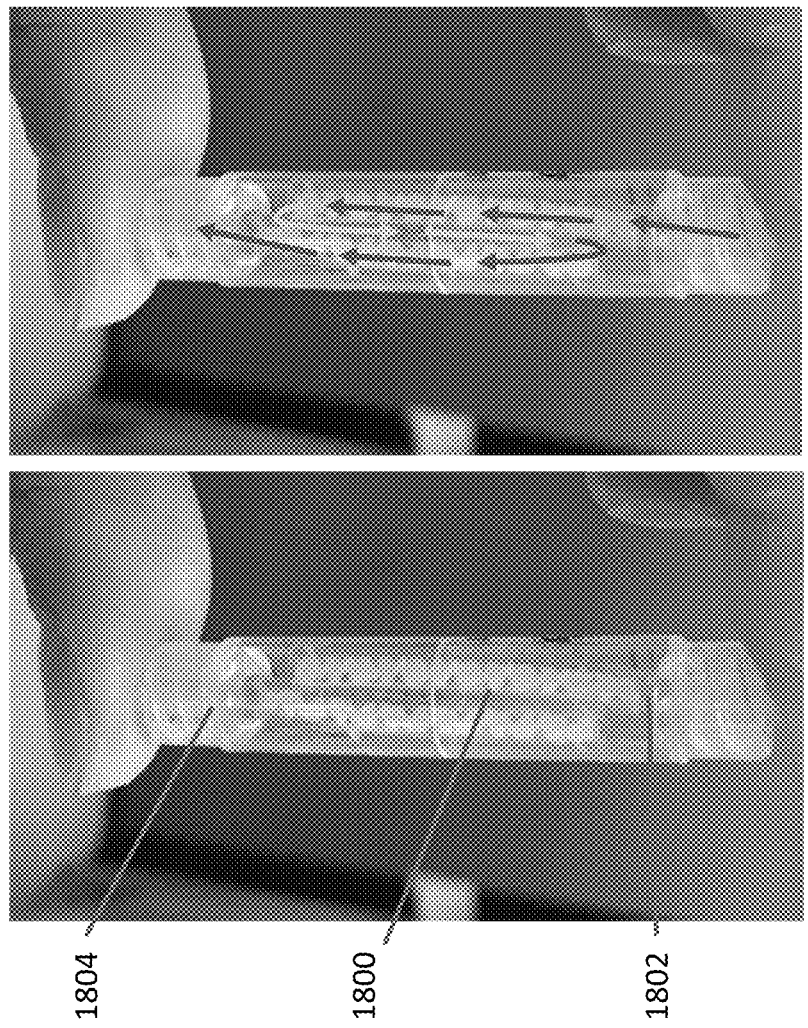

METHODS AND DEVICES FOR IN SITU FORMED NERVE CAP

INCORPORATION BY REFERENCE TO ANY PRIORITY APPLICATIONS

This application claims the benefit under 35 U.S.C. § 119(e) as a bypass continuation of PCT App. No. PCT/US2019/040429 filed on Jul. 2, 2019, which in turn is a nonprovisional application of U.S. Prov. App. No. 62/692,858 filed on Jul. 2, 2018 and U.S. Prov. App. No. 62/822,881 filed on Mar. 24, 2019, each of the foregoing of which are hereby incorporated by reference in their entireties.

BACKGROUND

Neuromas are benign tumors that arise from neural tissue and are composed of abnormally sprouting axons, Schwann cells, and connective tissue. Even though neuromas can appear following various types of injuries, some of the most common and challenging to treat are derived from trauma or surgical procedures in which neural tissue was damaged or transected. Amputation surgeries necessitate the transection of one or more sensory or mixed nerves. Chronic neuropathic pain, attributed to neuroma formation, develops in up to 30% of patient's post-surgery and results in downstream challenges with wearing a prosthesis. In addition to traumatic and amputation related neuromas, neuromas form across multiple clinical indications such as in general surgery (hernia repair, mastectomy, laparoscopic cholecystectomy), gynecologic surgery (C-section, hysterectomy), and orthopedics (arthroscopy, amputation, knee replacement).

Neuromas develop as a part of a normal reparative process following peripheral nerve injury. They are formed when nerve recovery towards the distal nerve end or target organ fails and nerve fibers improperly and irregularly regenerate into the surrounding scar tissue. Neuromas include a deranged architecture of tangled axons, Schwann cells, endoneurial cells, and perineurial cells in a dense collagenous matrix with surrounding fibroblasts (Mackinnon S E et al. 1985. Alteration of neuroma formation by manipulation of its microenvironment. Plast Reconstr Surg. 76:345-53). The up regulation of certain channels and receptors during neuroma development can also cause abnormal sensitivity and spontaneous activity of injured axons (Curtin C and Carroll I. 2009. Cutaneous neuroma physiology and its relationship to chronic pain. J. Hand Surg Am. 34:1334-6). Haphazardly arranged nerve fibers are known to produce abnormal activity that stimulates central neurons (Wall P D and Gutnick M. 1974. Ongoing activity in peripheral nerves; physiology and pharmacology of impulses originating from neuroma. Exp Neurol. 43:580-593). This ongoing abnormal activity can be enhanced by mechanical stimulation, for example, from the constantly rebuilding scar at the injury site (Nordin M et al. 1984. Ectopic sensory discharges and paresthesia in patients with disorders of peripheral nerves, dorsal roots and dorsal columns. Pain. 20:231-245; Scadding J W. 1981. Development of ongoing activity, mechanosensitivity, and adrenaline sensitivity in severed peripheral nerve axons. Exp Neurol. 73:345-364).

Neuromas of the nerve stump or neuromas-in-continuity are unavoidable consequences of nerve injury when the nerve is not, or cannot be, repaired and can result in debilitating pain. It has been estimated that approximately 30% of neuromas become painful and problematic. This is particularly likely if the neuroma is present at or near the skin surface as physical stimulation induces signaling in the nerve resulting in a sensation of pain.

The number of amputees in the world has risen significantly in recent years, with war injuries and dysvascular diseases such as diabetes accounting for approximately 90% of all amputee cases. There are currently about 1.7 million amputees living in the United States alone, and over 230,000 new amputee patients are discharged annually from hospitals. Further, it has been estimated that there will be a 20% increase in the number of new amputee cases per year by 2050.

Unfortunately, due to persistent pain in limb remnants, about 25% of amputees are not able to commence rehabilitation, much less resume ordinary daily activities. The cause of such pain can be a neuroma. One recent study reported that 78% of amputees experienced mild to severe pain as a consequence of neuroma formation over the 25-year study period, of which 63% described the pain as constant aching pain. The pain is also frequently described as sharp, shooting, or electrical-like phantom sensations that persist for years after surgical amputation. In addition, patients experience tenderness to palpation of the skin overlying the neuroma, spontaneous burning pain, allodynia, and hyperalgesia.

While various methods have been used to prevent, minimize, or shield neuromas in an attempt to minimize neuropathic pain, the current clinical "gold standard" for treating neuromas is traction neurectomy, in which the nerve is pulled forward under traction and transected as far back as possible in the hope that, if a neuroma forms, that it will be located deep in the tissue. Another well recognized approach is to bury the proximal nerve end (that will form the neuroma) into muscle or a hole drilled in bone. The nerve is then sutured to the muscle or periosteum of the bone to maintain its position. The rationale for this is that the surrounding tissue cushions and isolates the neuroma to inhibit stimulation and the resulting painful sensations. However, this procedure can greatly complicate surgery, as significant additional dissection of otherwise healthy tissue is required to place the nerve stump. This, coupled with poor and variable efficacy, the lack of appropriate/available tissue, and the additional procedural time required, result in the procedure being rarely performed to prevent neuroma formation.

Another method is to cut the nerve stump back to leave a segment or sleeve of overhanging epineurium. This overhang can be ligated to cover the face of the nerve stump. Alternatively, a segment of epineurium can be acquired from other nerve tissue or a corresponding nerve stump can be cut back to create an epineurium sleeve that can be used to connect with and cover the other nerve stump.

Yet another method that is commonly used is a suture ligation, where a loop of suture is placed around the end of the nerve and tightened. This pressure is believed to mechanically block the exit of axons and causes the terminal end to eventually form scar tissue over the site. Clinical and pre-clinical evidence has shown, however, that this procedure can cause a painful neuroma to form behind the ligation. Furthermore, the ligated nerve is generally not positioned to minimize mechanical stimulation of the neuroma, since it is anticipated that the scar tissue will provide sufficient protection to the nerve end.

Other methods used clinically include placing the nerve stump within a solid implantable silicone or biodegradable polymer tube with an open, or more recently, a sealed end (e.g. Polyganics NEUROCAP); wrapping the proximal nerve end with a harvested vein or fat graft, again with the goal of providing a physical barrier to aberrant nerve regeneration. The use of biomaterial implant devices and methods necessitate insertion and securing the nerve with sutures in the opening of the device, which can be difficult and further damage the nerve end. For example, the current procedure for securing the NEUROCAP requires a suture be placed in the epineurium of the nerve and through the wall of the tube and followed by pulling and stuffing the nerve into the lumen of the tube using the suture and the placement of several sutures to retain the nerve in the device. These methods and devices can also result in mechanical stimulation of the neuroma tissue as a result of 1) mismatch between the tissue compliance and the rigidity of the conduit and 2) inability of the cap to prevent neuroma formation within the cap, with resulting sensation of pain. Although these nerve caps degrade over a period of 3 months to 18 months, substantial degradation-mediated mass loss occurs in the first three to six months resulting in the exposure of a temporarily protected neuroma to the surrounding environment. Thus, the efficacy of these solid implantable caps is limited by the ability of the cap to conform to the proximal end of the nerve and prevent neuroma formation and secondarily their subsequent degradation to expose the neuroma to the surrounding environment. Finally, since these methods require suturing using fine sutures (9-0 nylon) the procedural time and skill required to secure these implants under surgical magnification (loupes) or harvested tissue prohibits surgeons from more broadly adopting these procedures.

Unfortunately, current methods for addressing the formation of and pain caused by neuromas have not been widely adopted. The need therefore remains for an effective technology or therapy for controlling or inhibiting neuroma formation following inadvertent or planned surgical or traumatic nerve injury in addition to reducing scar formation and perineural adhesions.

A variety of biomaterial conduits have been explored preclinically to try to prevent neuroma formation, including other solid implantable biodegradable polymeric conduits based on polylactide/polycaprolactone (Onode et al (2019) Nerve capping with a nerve conduit for the treatment of painful neuroma in the rat sciatic nerve, J Neurosurg. p. 1-9; Yan et al (2014) Mechanisms of Nerve Capping Technique in Prevention of Painful Neuroma Formation, PLOS One, 9(4) p. 1-11; Yi et al (2018) Painful Terminal Neuroma Prevention by Capping PGRD/PDLLA Conduit in Rat Sciatic Nerves Adv. Sci, 1-11), atelocollagen (Sakai et al (2005) Prevention and Treatment of Amputation Neuroma by an Atelocollagen Tube in Rat Sciatic Nerves. J Biomed Mater Res Part B: Appl Biomater 73B: 355-360) or porcine small intestine submucosa (Tork et al (2018), ePoster: Prevention of Neuromas with a Porcine SIS Nerve Cap: Histopathologic Evaluation, http://meeting.handsurgery.org/files/2018/ePosters/HSEP106.pdf) or microcrystalline chitosan (Marcol et al (2011) Reduction of Post-Traumatic Neuroma and Epineural Scar Formation in Rat Sciatic Nerve by Application of Microcrystallic Chitosan. Microsurgery, 31: 642-649). These approaches have not been successful to date in preventing the formation of neuromas either because, again, the solid implants do not form in situ and create a potential space to permit nerve outgrowth and varying degrees of neuroma formation or, critically, because the in vivo persistence of the materials was not sufficient to prevent neuroma formation.

Some embodiments as disclosed here have been demonstrated to prevent neuroma formation preclinically and 1) eliminate the need for suturing, dragging or stuffing of the nerve inside a conduit, 2) conform to the end of the nerve stump providing a physical barrier to nerve regeneration, and 3) provide mechanical strength to prevent nerve regeneration for a period of two months, preferably three months or more necessary to prevent nerve outgrowth during the growth regenerative phase after nerve injury. In situ forming implants described herein can be compliant with the surrounding tissue, adhere to but do not compress the underlying nerve tissue, are flexible such that they can move over regions of tissue involving joints or where nerves slide relative to other tissues and prevent scar tissue and adhesions forming around nerves. Finally, some of these in situ forming implants can be delivered without advanced surgical training. In other situations, there remains a need for a technology that prevent nerve outgrowth into the surrounding tissue and direct the outgrowth of a transected or compressed nerve into the distal nerve stump or allograft/autograft. With this, in some aspects, a suture-free technology that can direct nerve regeneration from a proximal nerve stump directly (via direct coaptation/anastomoses with distal nerve stump) or indirectly (through a nerve conduit, guidance channel, allograft, autograft), or through a growth-permissive matrix into the distal nerve stump is described. In addition, in some aspects, a technology that allows detensioning of the anastomoses site is described to promote better nerve regeneration. Lastly, in some aspects, a technology that can be quickly and broadly applied to nerves to prevent inadvertent damage to adjacent nerves during a variety of surgical procedures is desirable.

SUMMARY

There is provided in accordance with one aspect of the present invention a method of in situ formation of a conforming, protective nerve cap to inhibit neuroma formation at a severed nerve end. The method comprises the steps of identifying a severed end of a nerve; positioning the severed end into a cavity defined by a form; introducing media into the form to surround the severed end; and permitting the media to undergo a transformation from a first, relatively flowable state to a second, relatively non flowable state to form a protective conforming barrier surrounding the severed end. The method may further comprise the step of removing the form, to leave behind a formed biocompatible in situ protective nerve cap.

The identifying a severed end of a nerve step may comprise identifying a nerve severed such as by cutting or ablation, or severed traumatically. The form may comprise a nerve guide, and the positioning step may comprise positioning the nerve such that the nerve guide maintains the severed end within the cavity spaced apart from a sidewall of the form. The severed end may be positioned at least about 0.1 mm or 2 mm away from the sidewall or more preferably about 1 mm away. Preferably the form is either bioresorbable or is composed of a flexible nondegradable material that can easily be removed from the surgical site after formation of the in situ nerve cap.

The transformation from flowable to nonflowable state may occur within about 1 minute, or within about 30 seconds or within about 10 seconds of the introducing step. The method may additionally comprise the step of blotting a volume of axoplasm from the severed nerve prior to the introducing step.

In one implementation of the invention, the form may comprise a first configuration in which the cavity is exposed, and a second configuration in which the cavity is partially or completely covered; and further comprising the step of advancing the form from the first configuration to the second configuration following the introducing nerve step. Alternatively, the step of advancing the form from the first configuration to the second configuration may occur prior to the introducing the nerve or media steps. The form may alternatively comprise an open cell foam, and the cavity comprises a tortuous, interconnected interstitial volume within the foam. In the latter embodiment, the form would remain in place in situ after integration with and formation of the nerve cap.

The identifying a severed nerve step may include the step of severing a target nerve. The step may additionally comprise transecting the nerve cleanly at an oblique angle prior to placing the nerve within the form. The transformation step may comprise a crosslinking reaction or a polymerization and the use of an in situ forming hydrogel that can intercalate with the host tissue to form an adhesion between the hydrogel and the tissue. In the preferred embodiment, the hydrogel is a neutral or negatively charged material with submicron or smaller pores which permit nutrient and protein exchange but not cellular infiltration. In one implementation, the transformation produces a synthetic crosslinked hydrogel protective barrier through which nerves cannot regenerate around the end of a transected nerve stump.

The use of PEG as a biomaterial for delivery to nerves is well known in the art. Increasingly, there is an appreciation that biomaterials, including PEG hydrogels, need to be tuned for specific applications. Properties, including molecular weight, degradation kinetics, PEG shape (linear vs multi-arm vs dendritic), degree of crosslinking, degree of substitution, crosslinking type (electrophilic-nucleophilic or free radical), gelation time, arm length (in the case of multi-arm PEGs), functional groups, hydrolytic linkages, and other factors such as pH and buffer selection are tailored for specific applications directed towards nerves to prevent neuroma formation.

In some embodiments, disclosed herein is a dual component in situ forming biomaterial composition comprising a nerve growth permissive component and a nerve growth inhibitory component.

In some embodiments, the nerve growth permissive component is delivered first and the nerve growth inhibitory component delivered second.

In some embodiments, the nerve growth permissive components conform to the nerve and facilitate nerve ingrowth into, through and across the biomaterial into the distal stump.

In some embodiments, the nerve growth inhibitory components prevents nerve growth into the material.

In some embodiments, the nerve growth inhibitory components acts as a guide upon which nerve regeneration can occur.

In some embodiments, the biomaterial components comprise an in situ forming gel.

In some embodiments, the biomaterial components comprise in situ forming crosslinked gel, microparticles, nanoparticle, slurry or micelles.

In some embodiments, both the growth permissive and growth inhibitory components both contain polyethylene glycol (PEG).

In some embodiments, the PEG is a multi-arm PEG.

In some embodiments, the PEG is comprised of a urethane or amide linkage.

In some embodiments, the PEG comprised of an ester linkage.

In some embodiments, the PEG additionally comprises a linear end-capped PEG of 5,000 Daltons or less.

In some embodiments, the crosslinking is performed between a PEG-NHS ester and a PEG-amine or trilysine.

In some embodiments, the in situ forming gel contains pores 1 μm in size or larger.

In some embodiments, the in situ forming gel contains rods or filaments.

In some embodiments, the growth permissive component contains chitosan.

In some embodiments, the growth permissive component contains polylysine, preferably between 0.001 and 10 wt %, more preferably between 0.01 and 0.1 wt %.

In some embodiments, the nerve growth permissive components contains between 0.001 and 20% collagen, preferably between 3 and 6 w t %.

In some embodiments, the nerve growth permissive component contains between fibronectin.

In some embodiments, the growth permissive component contains poly-L-ornithine.

In some embodiments, the growth permissive component includes laminin, preferably between 0 and 5 wt %, more preferably between 0 and 0.5%.

In some embodiments, the swelling of the growth permissive component is less than 20%, preferably between 5 and 20%.

In some embodiments, the swelling of the growth inhibitory component is less than 30%, preferably between 0 and 10%.

In some embodiments, the swelling of the growth permissive component is less than or equal to the swelling of the growth inhibitory component.

In some embodiments, the compressive strength of the growth inhibitory component is greater than 10 kPa, preferably >30 kPa.

In some embodiments, the growth permissive and growth inhibitory component are different colors.

In some embodiments, the growth permissive region comprises agents that support nerve survival, outgrowth, and regeneration.

In some embodiments, the growth permissive region permits infiltration of Schwann or glial cells.

In some embodiments, a composition includes agents which may comprise one or more of growth factors, anti-inhibitory peptides or antibodies, and/or axon guidance cues.

In some embodiments, the system contains supporting cells such as glial cells, including Schwann cells, oligodendrocytes, or progenitor cells such as stems cells.

In some embodiments, the system is delivered to peripheral nerves or the spinal cord.

In some embodiments, the growth permissive and growth inhibitory region include a P2XR receptor antagonist.

In some embodiments, the P2XR receptor antagonist is a P2X7 receptor antagonist, including Brilliant Blue FCF (BB FCF) or Brilliant Blue G (BBG).

In some embodiments, the P2XR antagonist is a P2X3 receptor antagonist, such as

In some embodiments, the concentration of the P2XR antagonist is between 0.001 and 0.55% the hydrogel.

In some embodiments, disclosed is a kit including two or more in situ forming hydrogels. The kit includes a dual applicator system clearly marked with indicia as the growth permissive applicator and a dual applicator system clearly marked as the growth inhibitory applicator. Each component can be clearly color coded and includes a powder vial, a reconstitution/diluent solution, and an accelerator solution for use in the dual applicator system. The kit also may include two or more forms—one form for receiving the growth inhibitory hydrogel, the other for the growth permissive hydrogel.

In some embodiments, disclosed herein is a method of delivering dual in situ forming hydrogels to treat conditions involving nerves. The nerves can need repair, such as, for example, end-to-end anastomoses, coaptation, repair with allograft or autograft or conduit or wrap, or gap repair.

In some embodiments, a growth permissive region is delivered between the proximal and distal nerve stumps, between end-to-end anastomoses sites, between proximal stump and allograft/autograph.

In some embodiments, a growth permissive region is delivered between the proximal and graft and/or graft and distal stumps.

In some embodiments, a growth permissive region is delivered inside a conduit or wrap.

In some embodiments, a growth permissive region is delivered into a form that permits adherence of the growth permissive gel to the nerves but not the form.

In some embodiments, a growth inhibitory region is delivered after the growth permissive region.

In some embodiments, a growth inhibitory region covers the proximal and distal nerves and growth permissive region.

In some embodiments, a kit can include an in situ forming hydrogel. The kit includes a dual applicator system and a powder vial, a reconstitution/diluent solution, and an accelerator solution for use in the dual applicator system. The kit also may include a selection of forms in a range of sizes and lengths for receiving the hydrogel.

In some embodiments, a growth inhibitory region covers the anastomoses junction.

In some embodiments, a growth inhibitory region covers the junction(s) between the nerve and the conduit or wrap.

In some embodiments, a growth inhibitory region covers a healthy, compressed, or contused nerve.

In some embodiments, disclosed herein is a formed in place nerve regeneration construct, comprising: a growth permissive hydrogel bridge having first and second ends and configured to span a space between two nerve ends and encourage nerve regrowth across the bridge; and a growth inhibiting hydrogel jacket encapsulating the growth permissive hydrogel bridge and configured to extend beyond the first and second ends to directly contact the two nerve ends.

In some embodiments, disclosed herein is a method of encouraging nerve growth between a first nerve end and a second nerve end, comprising: placing the first nerve end and the second nerve end in a form cavity; introducing a growth permissive media into the cavity and into contact with the first nerve end and the second nerve end to form a junction; placing the junction into a second form cavity; and introducing a growth inhibiting media into the second form cavity to encapsulate the junction.

In some embodiments, disclosed herein is a form for creating an in situ nerve cap to inhibit neuroma formation, comprising: a concave wall defining a cavity, the wall having a top opening for accessing the cavity, the top opening lying on a first plane and having an area that is less than the area of a second plane conforming to inside dimensions of the cavity and spaced apart into the cavity and parallel to the first plane; and a concave nerve guide carried by the wall and providing a side access to the cavity.

In some embodiments, disclosed herein is a form for creating an in situ wrap around a nerve to nerve junction, comprising: a concave wall defining a cavity, the wall having a top opening for accessing the cavity, the top opening lying on a first plane and having an area that is less than the area of a second plane conforming to inside dimensions of the cavity and spaced apart into the cavity and parallel to the first plane; a first concave nerve guide carried by the wall and providing a first side access for positioning a first nerve end in the cavity; and a second concave nerve guide carried by the wall and providing a second side access for positioning a second nerve end in the cavity.

In some embodiments, disclosed herein is a composition for an in situ forming growth inhibitory hydrogel with: compressive strength greater than 10 kDa for over 3 months, in vivo persistence for at least 3 months comprising less than 15% mass loss, and/or swelling of less than 30% for over 3 months.

In some embodiments, the composition includes one or more of: poly(ethylene glycol) succinimidyl carbonate, a P2XR receptor antagonist, and/or a P2X7 receptor antagonist.

In some embodiments, a P2X7 receptor antagonist is Brilliant Blue FCF (BB FCF) or Brilliant Blue G (BBG).

In some embodiments, a method of in situ formation of a nerve wrap, comprising identifying a section of a nerve; positioning the nerve in a cavity defined by a form; introducing media into the cavity of the form to surround the nerve; and permitting the media to undergo a transformation from a first, relatively flowable state to a second, relatively non flowable state to form a protective barrier around the nerve.

In some embodiments, the nerve is healthy, compressed, or contused.

In some embodiments, the nerve is repaired through direct anastomoses, repair with allograft or autograft, or repair with a conduit.

In some embodiments, the method includes removing the form.

In some embodiments, the form comprises a nerve guide, and positioning comprises positioning the nerve such that the nerve guide maintains the nerve spaced apart from a sidewall of the form.

In some embodiments, a method of in situ formation of a nerve wrap includes where the nerve is covered circumferentially with at least 0.5 mm of a protective barrier.

In some embodiments, the transformation occurs within about 10 seconds of the introducing step.

In some embodiments, the transformation comprises a crosslinking or polymerizing.

In some embodiments, the transformation produces a synthetic crosslinked hydrogel protective barrier.

In some embodiments, the protective barrier has an in vivo persistence of at least about two months.

In some embodiments, the protective barrier has an in vivo persistence of at least about three months.

In some embodiments, the transformation causes the media to swell in volume within the range of from about 2% to about 60%.

In some embodiments, the transformation causes the media to swell in volume within the range of from about 20% to 60%.

In some embodiments, the method includes forming a form in situ before the positioning the severed end; and/or delivering the media around the nerve in two successive steps.

In some embodiments, the severing a target nerve step and the positioning a form at a treatment site step are accomplished by a single instrument.

In some embodiments, the viscosity of the flowable media is less than 70,000 cps.

In some embodiments, the density of the flowable media is less than 1 g/cm³.

In some embodiments, the form is comprised of silicone.

In some embodiments, the form contains an integral posts for seating longer lengths of the nerve.

In some embodiments, the wrap is comprised of PEG.

In some embodiments, the form has a clamshell lid.

In some embodiments, the growth permissive and growth inhibitory region contain a P2XR receptor antagonist.

In some embodiments, the P2X7 receptor antagonist is a P2X7 receptor antagonist, including Brilliant Blue FCF or Brilliant Blue G (BBG).

In some embodiments, the concentration of the P2XR antagonist is between 0.001 to 0.55% in the hydrogel.

In some embodiments, disclosed herein are in situ forming hydrogel(s) as a cap. In some embodiments, the nerve cap is not pre-formed.

Some embodiments as disclosed herein include in situ forming hydrogel scaffolds or ones that can be formed/wrapped in situ around a nerve. In some embodiments, systems and methods do not include a nerve guidance conduit (tube with two open ends) rather than a cap. In some embodiments, disclosed herein are systems and methods for delivering the hydrogel circumferentially around the nerve in appropriately designed forms. In some embodiments, systems and methods can include use of a form or the specific design of the PEG hydrogel to prevent neuroma formation such as circumferential delivery, in vivo persistence, minimal swelling etc. and delivering them into a removable form.

BRIEF DESCRIPTION OF THE DRAWINGS

FIG. 1B is a side elevational cross section through the construct of FIG. 1A.

FIG. 1D is an end view of the construct of FIG. 1A.

FIG. 1E is a cross-sectional view taken along the line 1E-1E in FIG. 1B.

FIGS. 11A-11E illustrate views of a form and methods of use.

FIGS. 14A-14C is a perspective view of a cap form with a partial clamshell.

FIGS. 15A-15C is a perspective view of a tearable nerve cap form.

FIGS. 18A-18B illustrate a mixing element design to improve the consistence of the hydrogel when delivering low volumes of precursor solution.

DETAILED DESCRIPTION

Figure 1A:
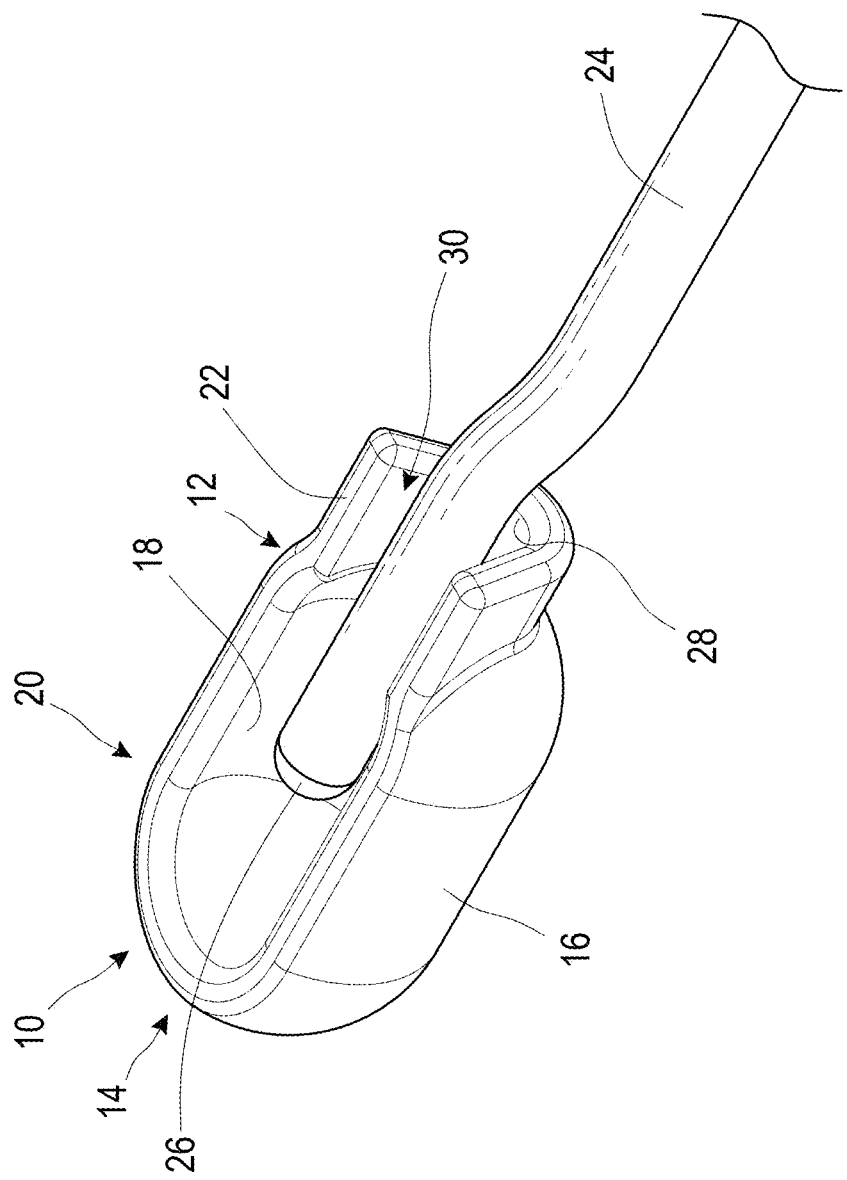
FIG. 1A is a perspective schematic view of a nerve end positioned within a form cavity. An entrance region that permits the nerve to guided into the form. The length of the form is provided to provide a sufficient surface area over which the hydrogel to form and adhere to the nerve tissue.

Some aspects of the present invention involve in situ formation of a protective barrier around an end of a nerve using injectable or surgically introduced media which may be a gel/hydrogel or gel precursors to block nerve regeneration and/or neuroma formation and inflammation and adhesion etc. around/in contact with nerves. Access may be by way of an open surgical approach or percutaneous (needle, endovascular/transvascular). The nerve end or stump may be formed by transection (cutting), traumatic injury, or ablation through any of a variety of modalities including RF, cryo, ultrasound, chemical, thermal, microwave or others known in the art.

The hydrogels may 'adhere' to the end of the nerves providing a snug, conforming, cushioning barrier around the end of a nerve as opposed to a cap with a void (inflammatory cells/fluid cysts present causing neuroma formation). Hydrogels are transparent for visualization, low-swelling, compliant, and are delivered into a form to generate hydrogel caps with volumes 0.1 to 0.5 ml. The barrier may inhibit neuroma formation purely through mechanical blocking of nerve regrowth. The media may additionally comprise any of a variety of drugs such as for inhibiting nerve regrowth as is discussed in further detail herein.

Target nerves can vary widely in diameter or non circular outside configuration, and the cut or severance angle and precision can also vary. In accordance with some embodiments of the present invention, capping is best accomplished by forming a soft, cushioning and conformable protective barrier in situ. A flowable media or media precursor(s) may be introduced to surround and conform to the configuration of the nerve end, and then be transformed into a non flowable state to form a protective plug in close conformity with and bonded to the nerve end. To contain the media before and during transformation (e.g., crosslinking), the media may be introduced into a form into which the nerve end has previously or will be placed. Filling the media into a form allows the media to surround the nerve end and transform to a solid state while contained in a predetermined volume and configuration to consistently produce a protective, conforming nerve cap regardless of the diameter and configuration of the nerve stump.

Referring to FIGS. 1A through 1D, there is illustrated a nerve cap form 10. The form 10 extends between a proximal end 12, a distal end 14 and includes a side wall 16 extending there between. Sidewall 16 is concave to produce a form cavity 18 therein. The form cavity 18 is exposed to the outside of the form by way of a window 20.

The proximal end 12 of the form 10 is provided with a nerve guide 22 to facilitate passage of the nerve 24 to position the nerve end 26 within the form cavity 18. The nerve guide 22 may comprise a window or opening in the proximal end wall 12 of the form 10, and is configured to support the nerve at a level that positions the nerve end 26 within the form cavity 18. In the illustrated embodiment, the nerve guide 22 includes a support surface 28 on an upwardly concave housing to produce a nerve guide channel 30. See FIG. 1D. FIG. 1E is a cross-sectional view taken along the line 1E-1E in FIG. 1B.

Figure 1C:
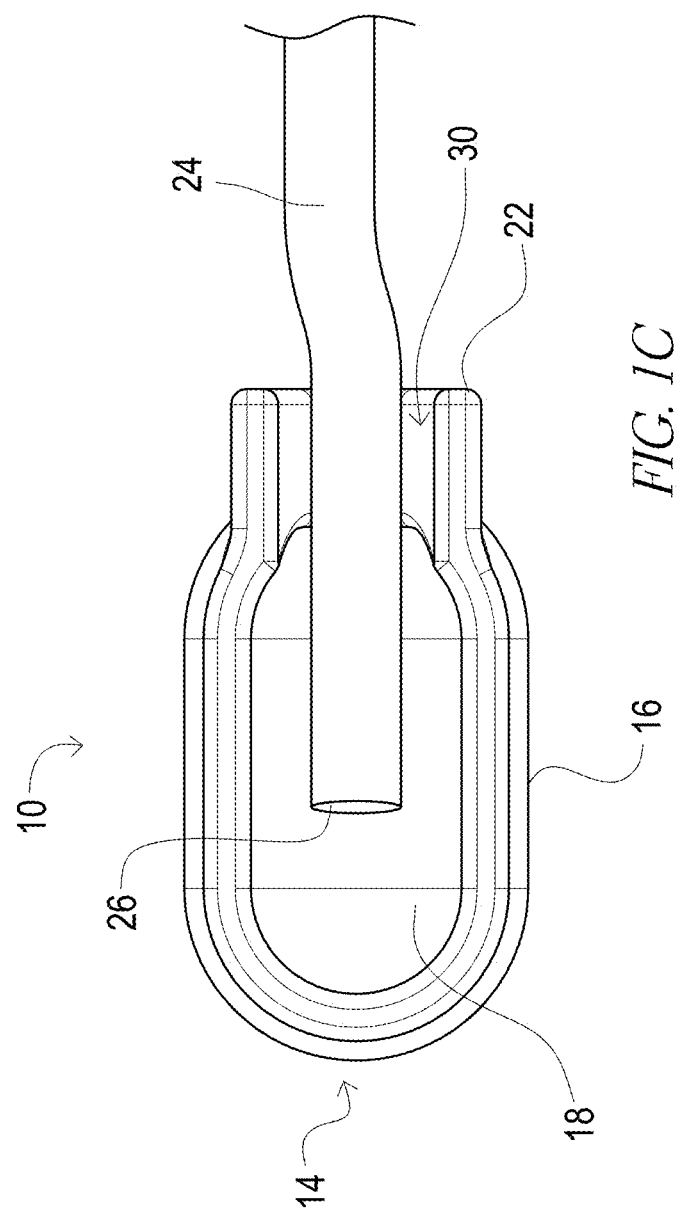
FIG. 1C is a top view of the construct of FIG. 1A.

Referring to FIGS. 1B and 1C, the nerve end 26 is positioned such that at least 1 mm and preferably 2 mm or more in any direction separate the nerve end 26 from the interior surface of the side wall of the form 10. This permits the media 27 to flow into the form cavity and surround the nerve end 26 to provide a protective barrier in all directions.

Figure 2:
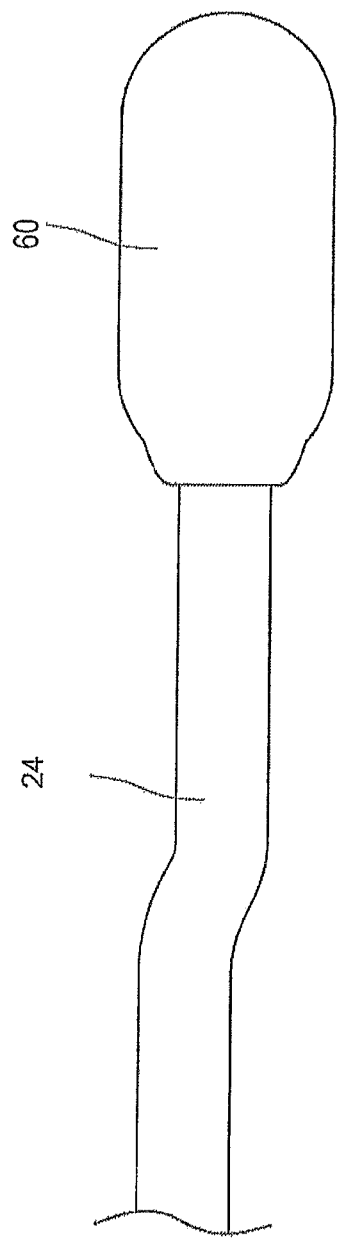
FIG. 2 is a schematic illustration of a formed barrier formed in accordance with some embodiments of the present invention.

Following transformation of the media from a relatively flowable state to a relatively non-flowable state, the form 10 may be left in place, or may be peeled away to leave behind a formed barrier 60 in the form of a plug as is schematically illustrated in FIG. 2.

Figure 3:
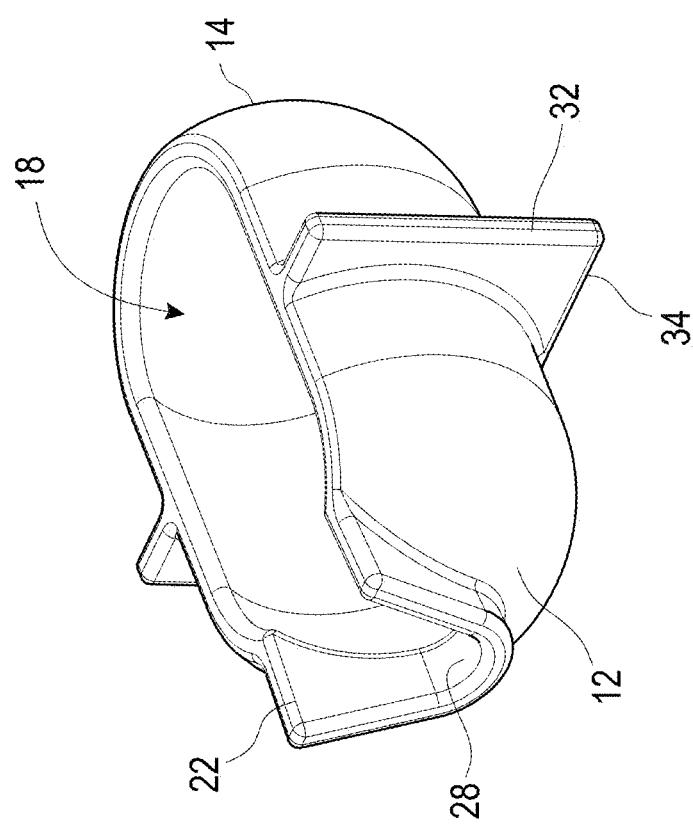
FIG. 3 is a perspective view of a form, having a stabilizing feature.

In order to stabilize the form 10 following placement and during the filling and transformation stages, at least one stabilizing feature 32 may be added. See FIG. 3. The stabilizing feature 32 maybe at least one or two or four or more ridges, flanges or feet which provide a transverse support surface 34 for contacting adjacent tissue and stabilizing the form against motion. The transverse support surface 34 may extend along or be parallel to a tangent to the sidewall of the form 10.

In one implementation of the invention there is provided a dual hydrogel construct with connectivity across the junction between two nerve ends achieved by creating a growth permissive hydrogel junction between the two opposing nerve ends, then encapsulating that junction with a growth inhibitory hydrogel capsule. The use of an in situ crosslinking hydrogel for the growth permissive media produces a junction with sufficient mechanical integrity and adhesiveness that it can be picked up as a unit as if it were an intact nerve and then placed in a second form to form the outer growth inhibitory hydrogel capsule.

Figure 4:
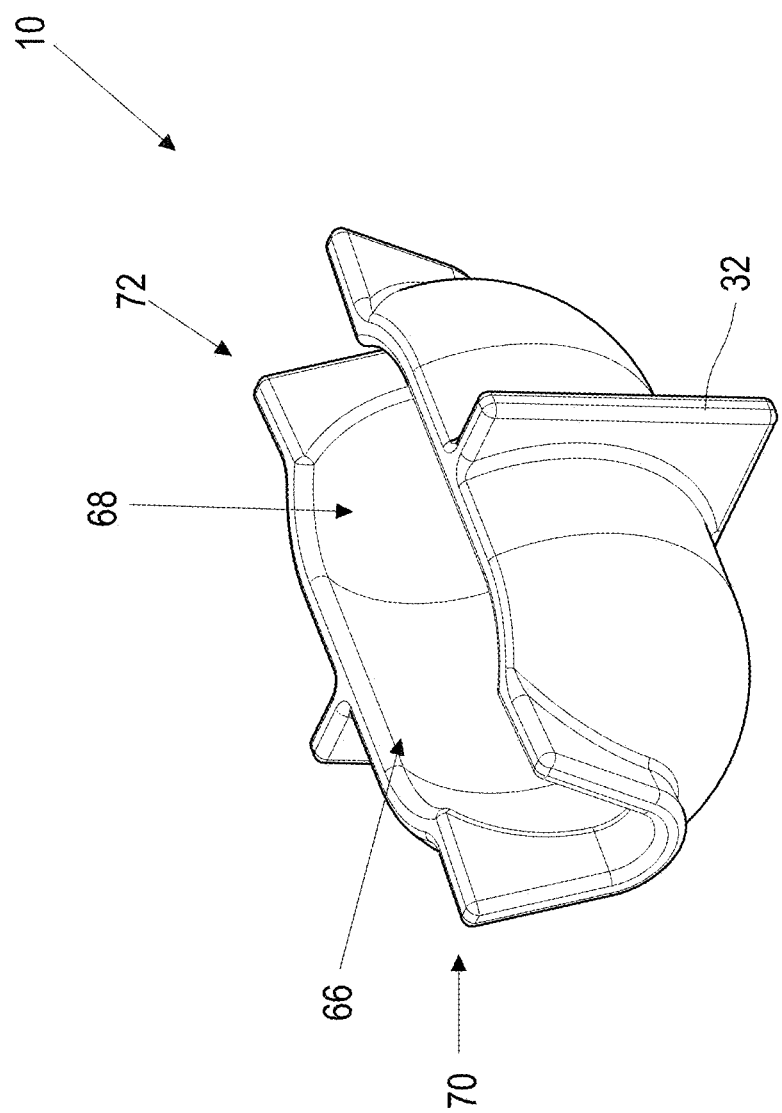
FIG. 4 is a perspective view of a form for creating a wrap around a nerve or a growth permissive region between a nerve. Thus, depending on the application, the wrap form may contain a growth permissive or growth inhibitory hydrogel.

Referring to FIG. 4, a form 10 includes a curved side wall 66 defining a form cavity 68. A first nerve guide 70 and a second nerve guide 72 are in communication with the cavity 68 and dimensioned and oriented to allow positioning first and second nerve ends into the cavity 68 in a position where they will face each other and become surrounded by flowable media introduced into the cavity 68.

Referring to FIGS. 5A-5E, there is illustrated a sequence of steps for forming a dual hydrogel conductive nerve junction between two nerve ends. A first form 50 comprises an elongate side wall curved to form a concavity such as in the form of a half of a cylinder, having an inside diameter larger than the diameter of a target nerve. The form 50 has a first end 52, a second end 54 and an elongate channel 56 extending there between. The first nerve end 58 is positioned within the channel 56 from the first end 52. A second nerve end 60 extends into the channel 56 from the second end 54. The result is a form cavity 62 formed between the first and second nerve endings and the sidewall of the form 50.

Figure 5A:
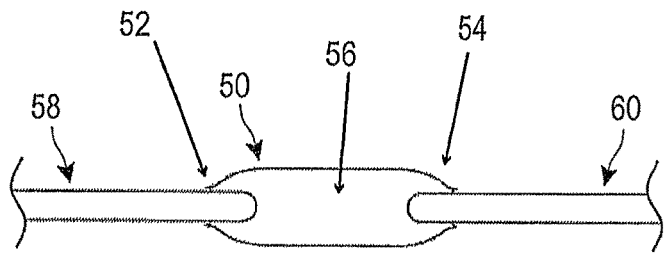
FIGS. 5A-5E illustrate a series of steps for creating a growth permissive hydrogel junction encapsulated by a growth inhibitory hydrogel barrier.
Figure 5B:
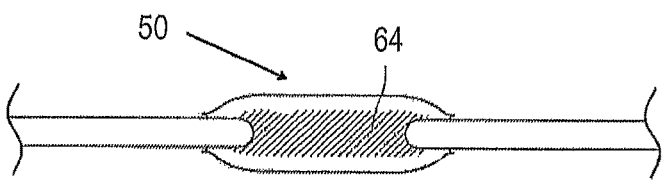
Figure 5C:
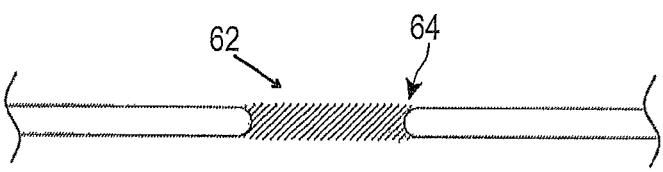
Figure 5D:
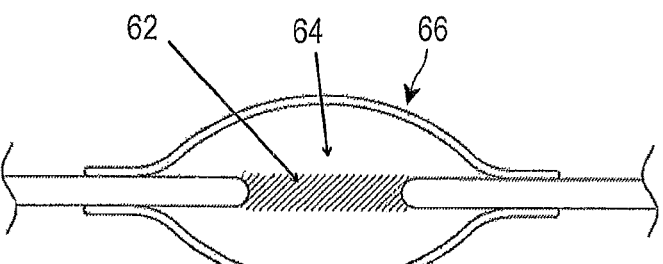
Figure 5E:

A transformable growth permissive hydrogel precursor is introduced into the form cavity 62 to adhere to the nerve ends and polymerize in situ to form a conductive bridge 64 between the first nerve end 58 and second nerve end 60 as shown in FIG. 5B. Following transformation of the gel to a less flowable state, the form 50 is removed as shown leaving a junction comprising the nerve ends connected by a conductive bridge 64 of polymerized growth permissive gel 62. See FIG. 5C.

Thereafter the polymerized junction is placed within a second form 66 having a central chamber 68 separating first and second nerve supports 70, 72, such as that illustrated in FIG. 4. A second growth inhibitory hydrogel precursor is introduced into the central chamber 68 to surround and over form the conductive bridge 64 and nerve ends to produce a final construct in which the first growth permissive polymer bridge 62 is encapsulated by second, growth inhibitory polymer capsule 70. See FIG. 5E.

Figure 6:
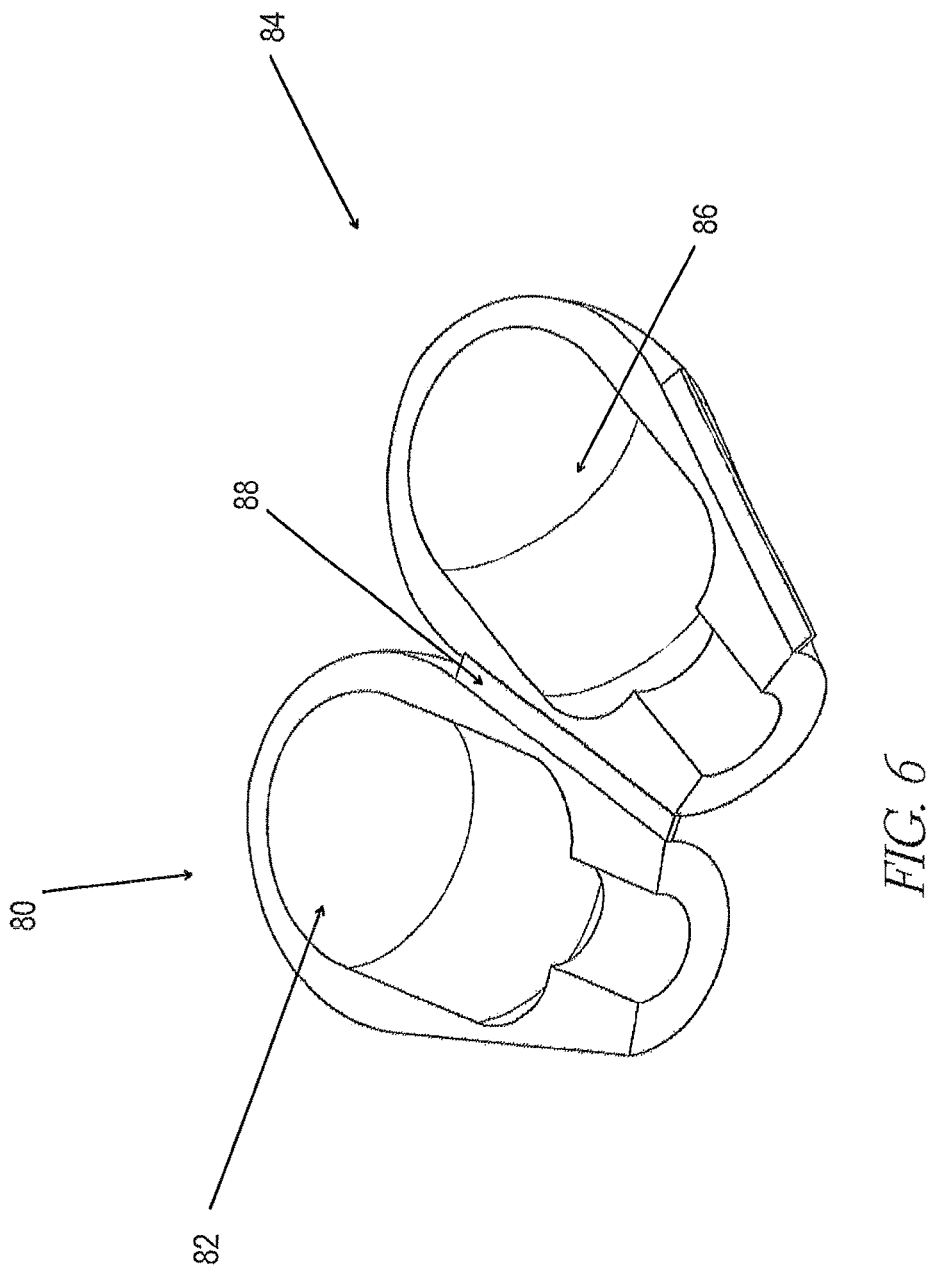
FIG. 6 is a perspective view of a clamshell form.

Either the nerve capping or nerve regeneration forms of some embodiments of the present invention can be provided in a clam shell configuration such as that illustrated in FIG. 6. A first shell 80 defines a first cavity 82 and a second shell 84 defines a second, complementary cavity 86. The first and second shells are joined by a hinge 88 such as a flexible living hinge made from a thin polymeric membrane. The first and second shells 80, 84 can be rotated towards each other about the hinge 88 to form an enclosed chambered form.

Figure 7:
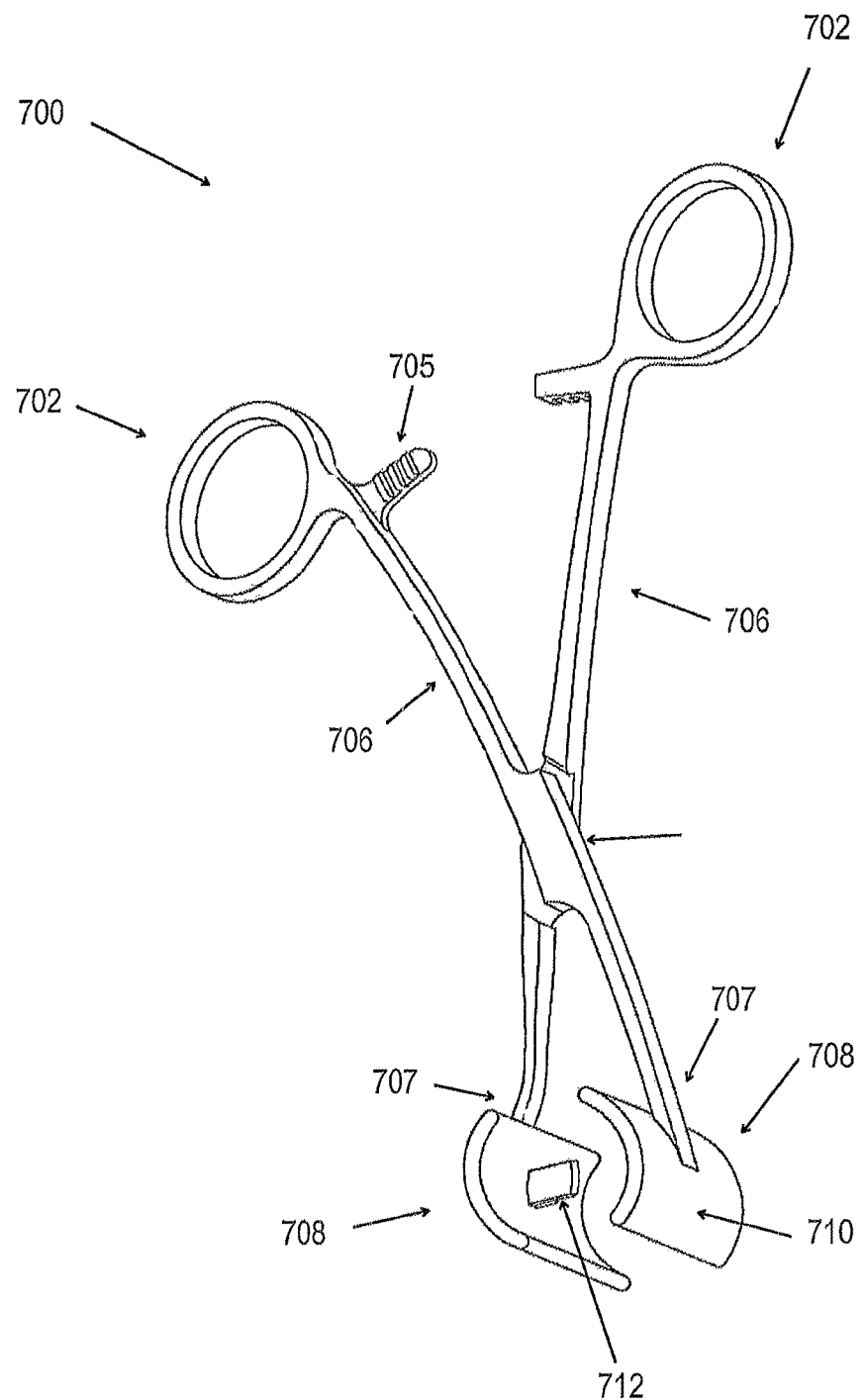
FIGS. 7-10C illustrate embodiments of tools for transecting nerves and/or creating a hydrogel junction.

FIG. 7 illustrates a perspective view of a clamping tool 700 configured to cut nerve tissue, as well as to house a form for forming a hydrogel nerve junction such as disclosed elsewhere herein, e.g., after transecting a nerve. The tool 700 can include a plurality of proximal movable grips 702, each connected to shafts 706 connected at pivot 704, and can have an unlocked configuration as shown, movable to a locked configuration utilizing a locking mechanism 705, such as a series of interlocking teeth. The distal ends 707 of the shafts 706 can include end effectors 708 that can include sidewalls 710 that can have a curved geometry as shown, and complementary cutting elements 712 operably connected to the curved sidewalls. In some embodiments, a form 10 can be connected to the sidewall 710 after cutting the nerve. In other embodiments, a form can include an integrally formed cutting element. In some embodiments, the cutting element can be detached or otherwise removed after cutting, leaving the form in place.

Figure 8:
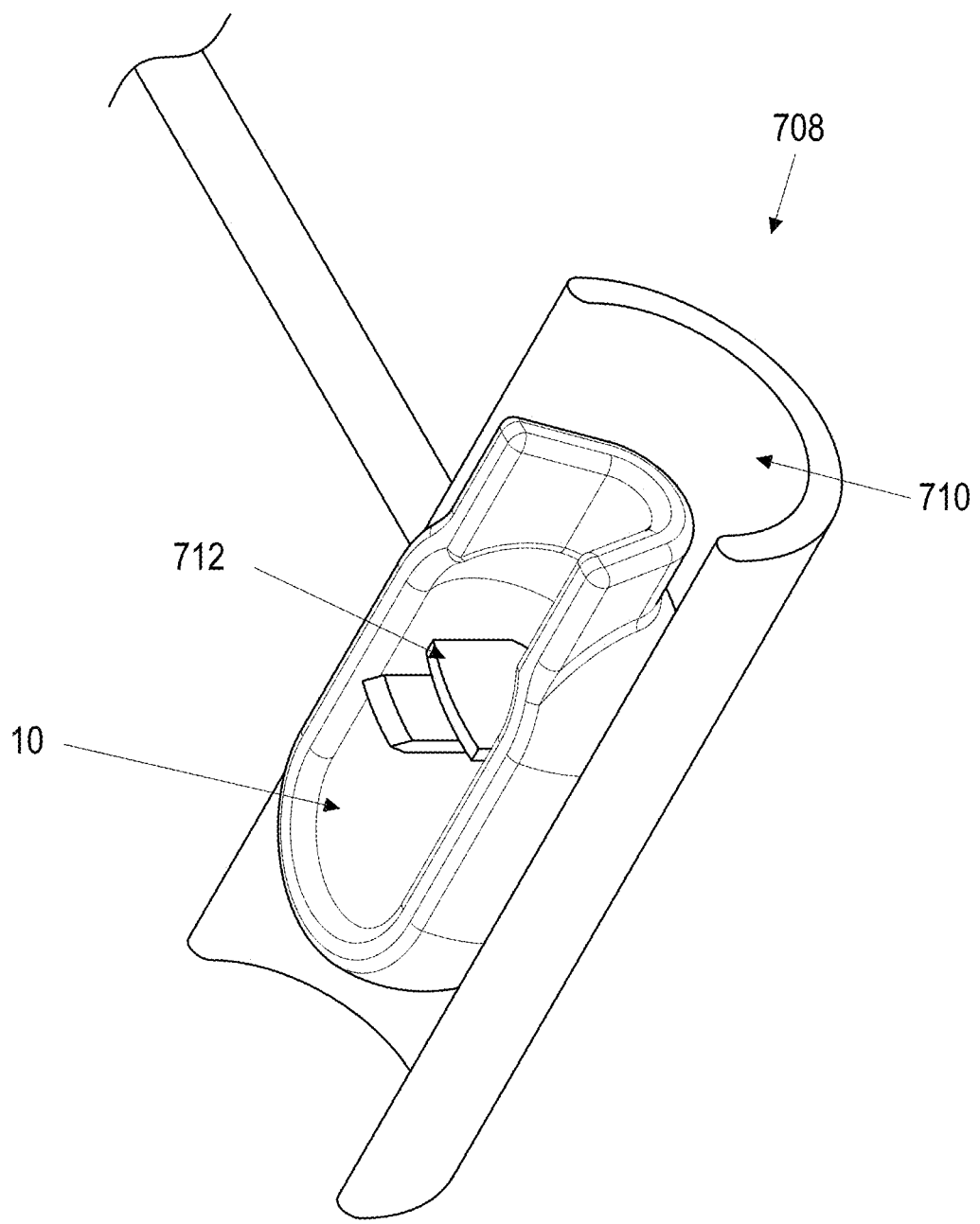
Figure 9:
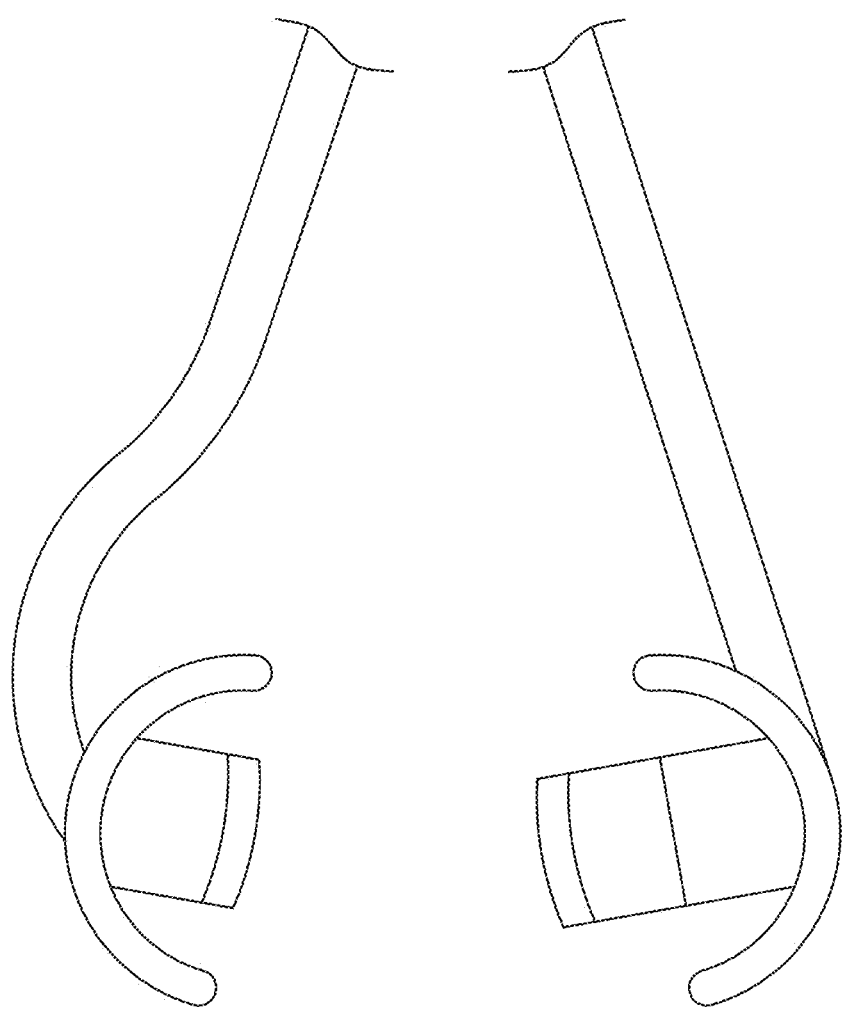

FIG. 8 is a close-up view of an end effector 708 of FIG. 7, also illustrating that the end effector 708 can also carry a form 10. FIG. 9 is a side close-up view of the distal end of an embodiment of the tool, illustrating that each of the end effectors can include cutting elements and/or forms.

Figure 10A:
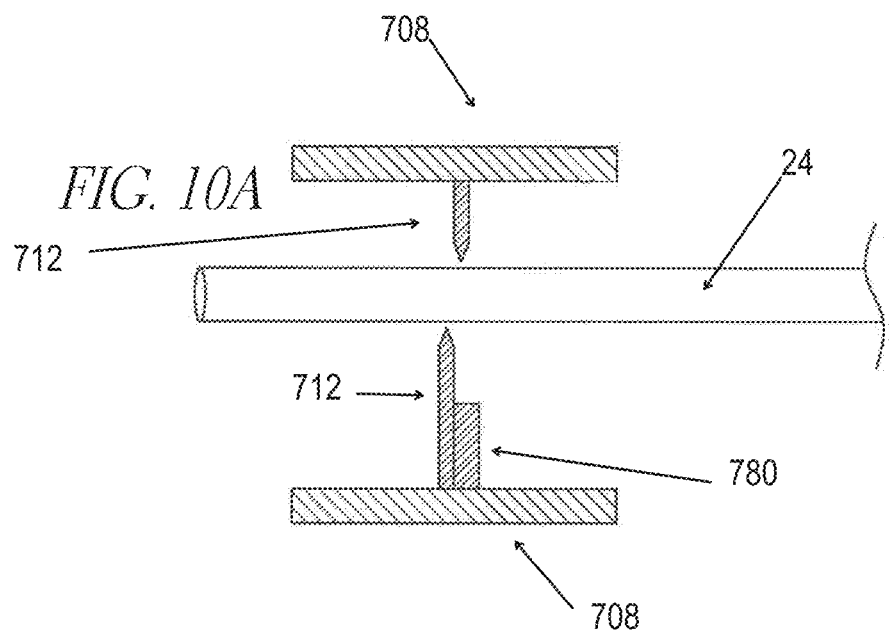
Figure 10B:
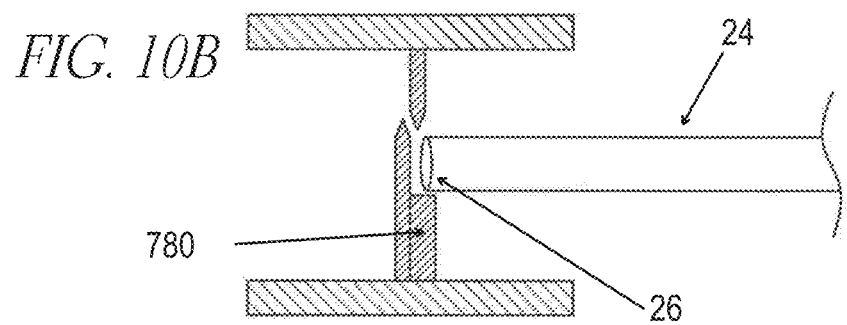
Figure 10C:
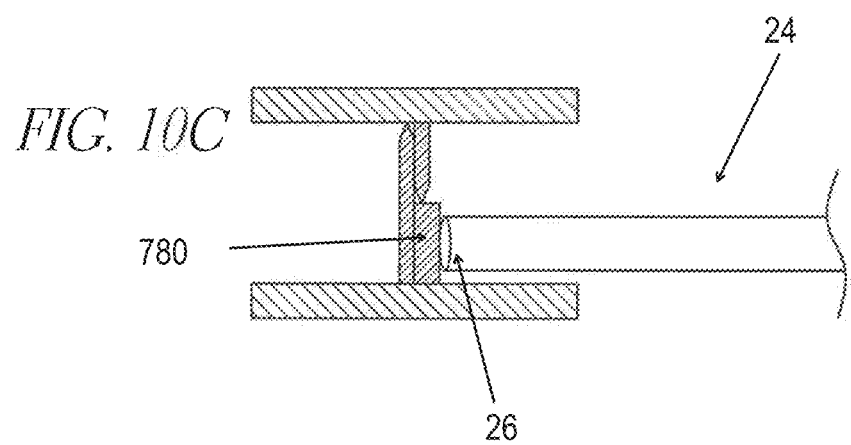

FIGS. 10A-10C illustrate various stages of a method of transecting a nerve while removing axoplasm from the nerve tip, to improve close apposition between the nerve end and the hydrogel. In some embodiments, opposing end effectors 708 can include blades 712, which can be of equal or unequal length. Blades 712 on each end effector 708 can be generally opposing, but offset from each other as shown in some embodiments. Actuating the end effectors 708 can result in the blades transecting the nerve 24 creating a nerve end 26. The blades can be within a form as previously described. An absorbent material 780 such as a swab can be connected to one or more end effectors 708 (such as within a form, for example) and be proximate, such as directly adjacent one or more of the blades 712, in order to absorb any axoplasm after nerve transection. The tip of the swab can be, for example, less than 5 mm, more preferably less than 2 mm in order that it may fit comfortably within the form and hold the nerve while the hydrogel is delivered.

Referring to FIGS. 11A-11E, in some embodiments, a delivery needle 1102 is advanced into an opening 1104 of the cap form 1100 to deliver the hydrogel precursor in and around the nerve 1124. Also shown is nerve guide 1122 which can be as described elsewhere herein. See FIG. 11A. Hydrogel may be delivered in to successive applications, to half fill the form and for a hydrogel 1150 as shown in FIG. 11B and then completely fill the form as shown in FIG. 11C and form a hydrogel cap after which the form is removed. Hydrogel is delivered in a small bolus 1152 to surround the tip of the nerve as shown in FIG. 11D and then the remainder of the cap is subsequently filled to form a hydrogel cap after which the form is removed as shown in FIG. 11E.

Figure 12:
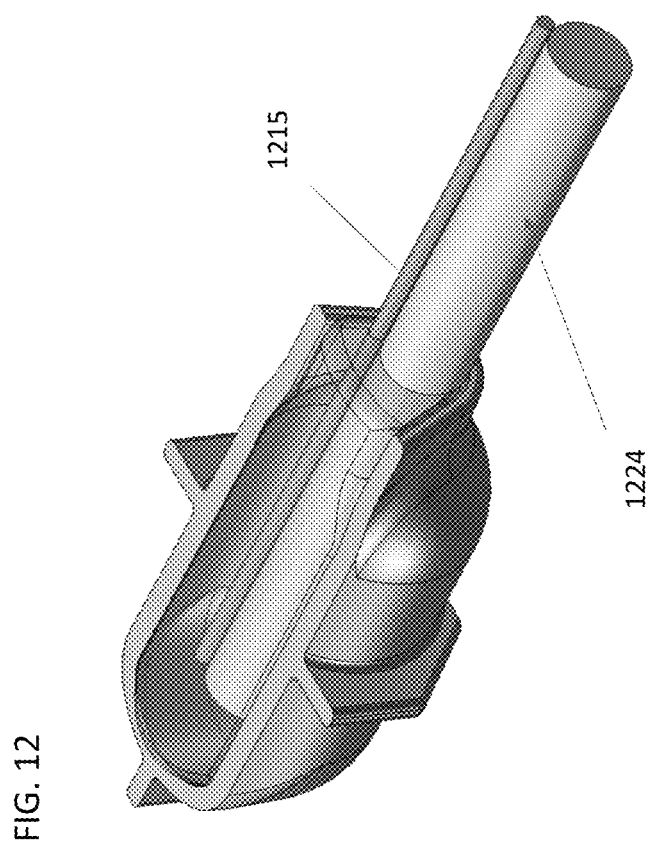
FIG. 12 is a perspective view of a form with a stabilizing rod.

Referring to FIG. 12, in some embodiments, a biodegradable rod 1215 is placed adjacent to and in continuity with the length of the nerve 1224. The rod 1215 provides additional strength to the nerve 1224 and naturally adheres to the nerve 1224 such that, irrespective of the rod's position, the nerve 1224 adheres to the rod 1215. The hydrogel solution is then delivered on or around the nerve 1224 and the biodegradable rod 1215 to form a nerve cap.

Figure 13B:
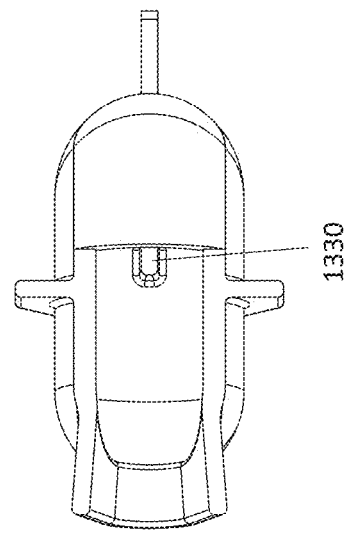
FIGS. 13A-13D is a perspective view of a cap form with a partial cover and in internal rod to support the nerve.
Figure 13D:
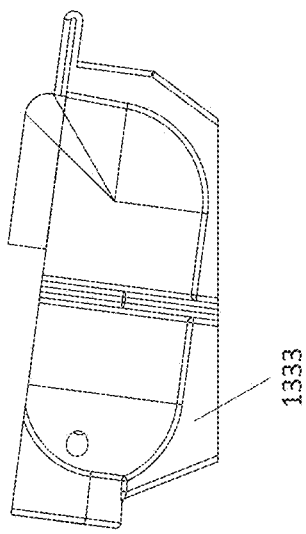
Figure 13A:
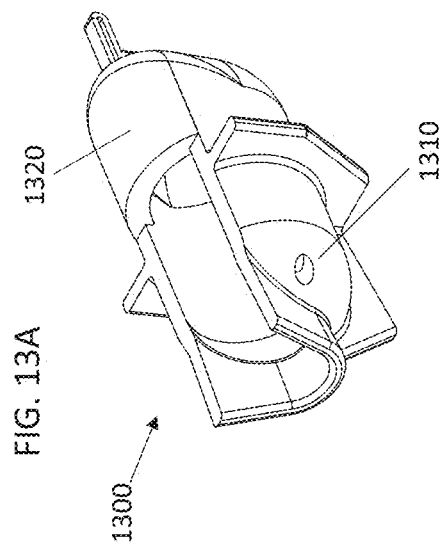
Figure 13C:
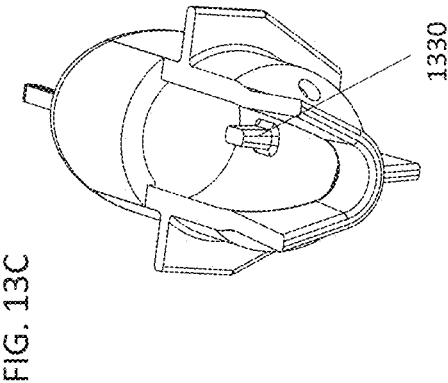

Referring to FIGS. 13A-13D, in some embodiments, one, two, or more apertures 1310 are provided in the side of a cap or wrap form 1300 to guide the needle to deliver the precursor solution in the correct location. The hole 1310 may be in one of many locations around the form as is needed to deliver the precursor solution 13A. A post 1330 may be included in the bottom of a cap or wrap form to provide additional support to the nerve. The nerve length is rested on top of the post 1330 while taking care that the tip of the nerve does not come in contact with the post 1330. The post 1330 may be integral to the cap or wrap form and is subsequently removed when the form is removed. Alternatively, the post 1330 may comprise a biodegradable post that remains integral to the hydrogel cap. See FIGS. 13B and 13C. In some embodiments, a cap form can include a partial lid 1320, shown in FIG. 13A. The form is tilted such that the precursor material will flow to and fill the distal cap first, surrounding the proximal nerve stump end and then subsequently fill the rest of the nerve cap. As shown in FIG. 13D, the cap or wrap form can also include raised tabs 1333.

FIGS. 14A-14C illustrates various views of an embodiment of a nerve cap form 1400 similar to that shown in FIGS. 13A-13D with a partial lid 1420 connected via a hinge 1428 with an insert 1440 to assist in centering the lid 1420 on the cap form 1400. Also shown is nerve guide, which can be as described elsewhere herein.

FIGS. 15A-15C illustrate various views of a tearable cap form 1500 that can include a peelable sheath 1560 including a sidewall 1561, into which the nerve is placed (nerve channel 1562). The precursor solution is delivered into and around a first nerve channel 1562 and the peelable sheath 1560 is subsequently torn off the nerve 1524, such as using a tearable tab 1564 as shown in FIG. 15A. The nerve hydrogel 1570 is then rotated approximately 90 degrees and placed in a second larger diameter peelable cap form 1501. The precursor solution is then applied into the nerve channel to surround the nerve and the first cap form. The peelable sheath is then torn off the second tearable cap form 1501. The resultant cylindrical cap form contains the centered nerve. The nerve 1524 can then be rotated back to the normal physiologic position, as shown in FIG. 15B. FIG. 15C illustrates an alternate tearable cap form design which can include a plurality of tabs.

Figure 16B:
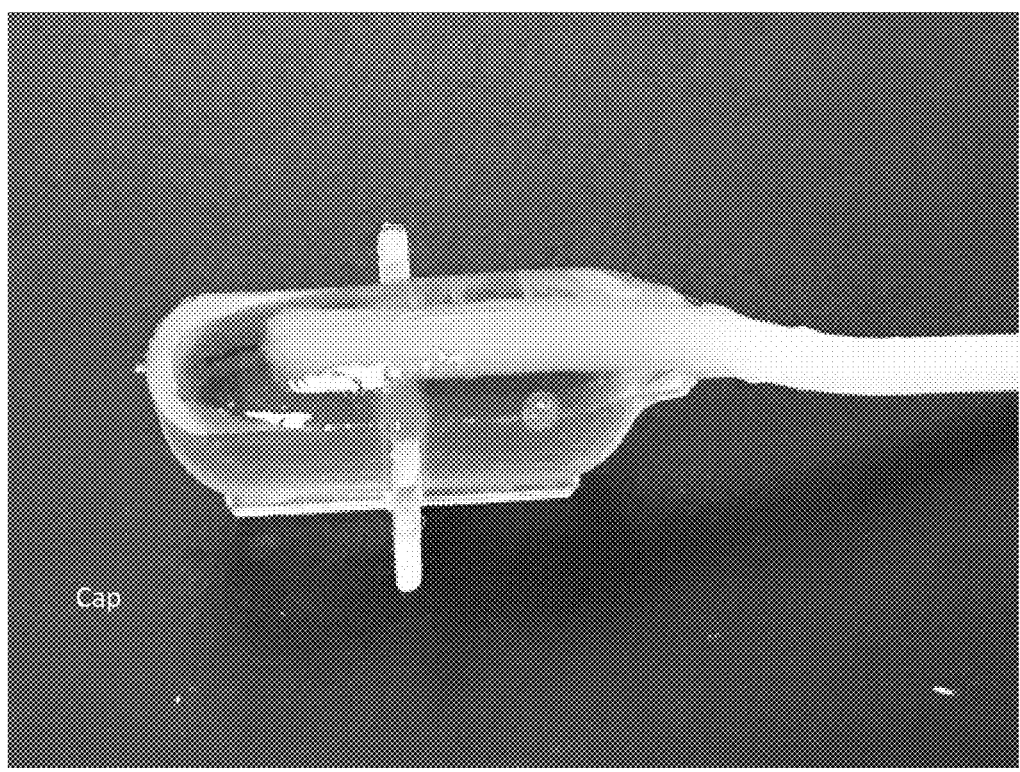
FIGS. 16Ai-16E illustrate perspective views and photographs of in situ formed hydrogels (growth inhibitory and growth permissive) around nerves both in cap and wrap form.
Figure 16C:
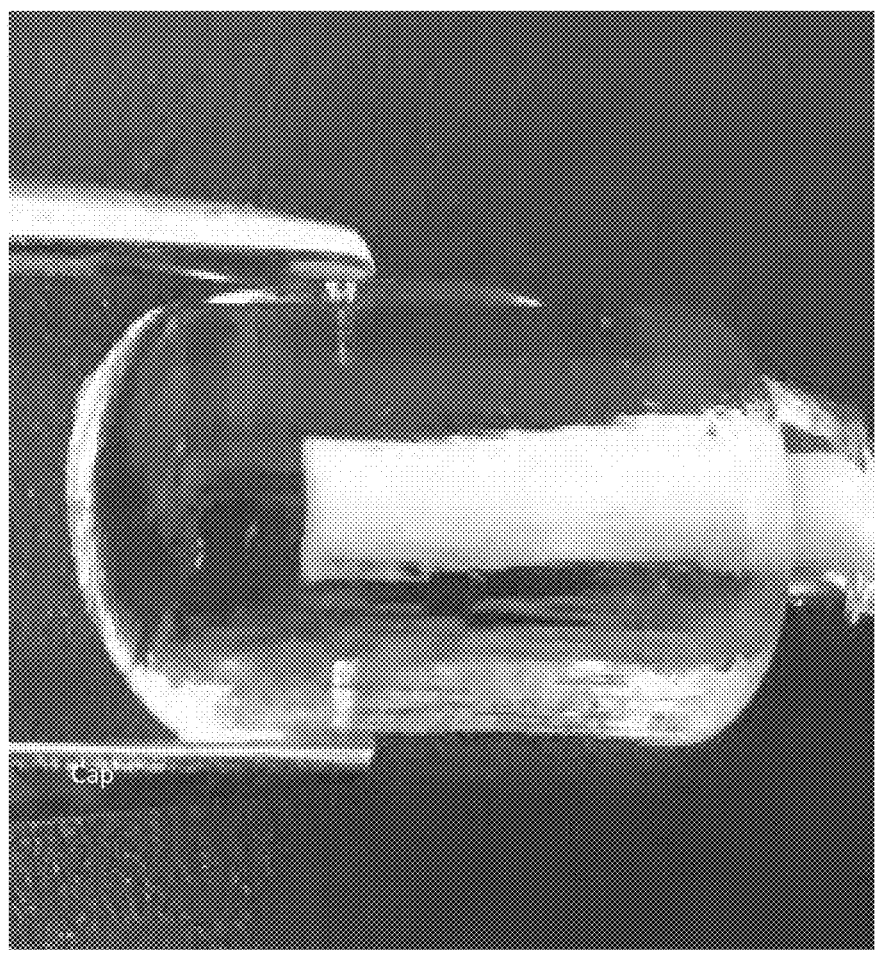
Figure 16D:
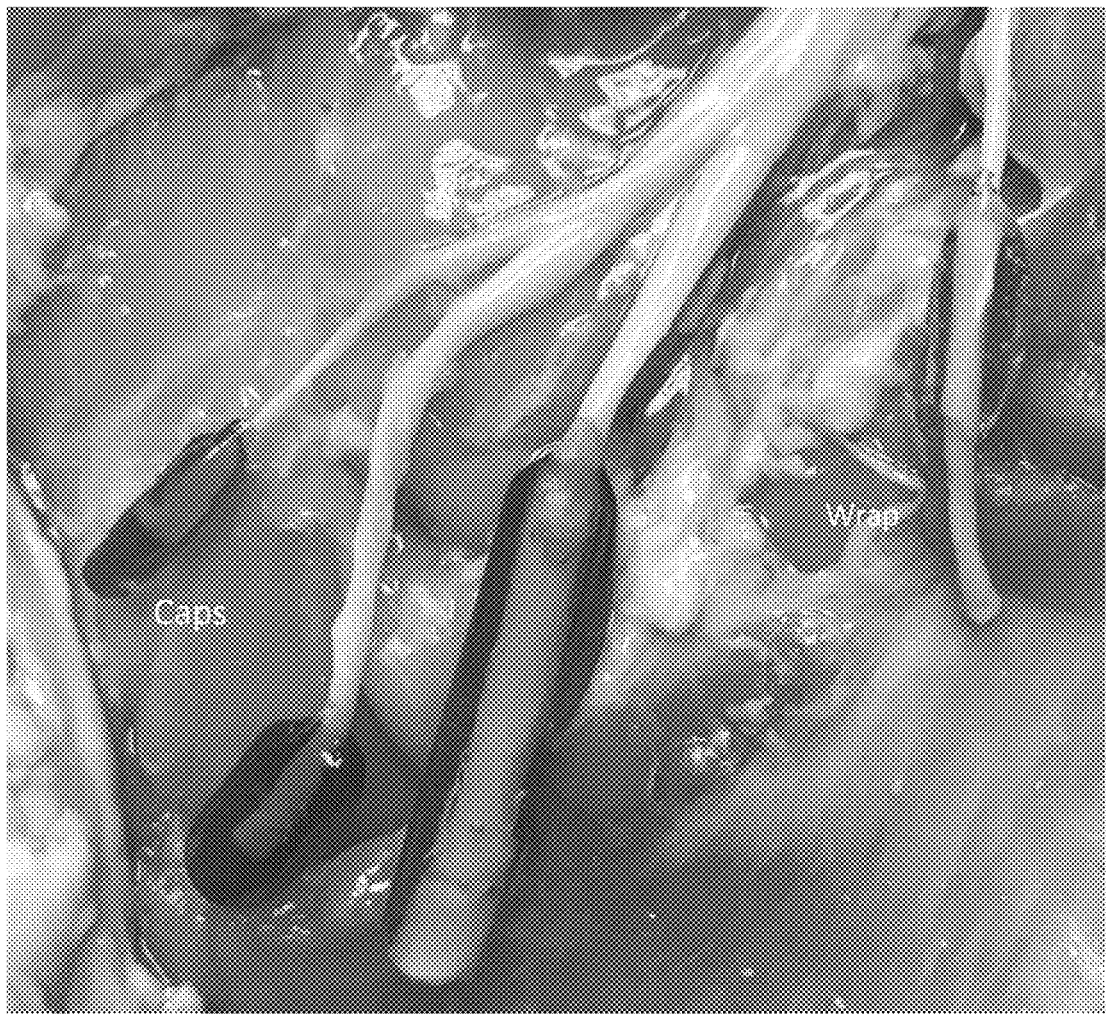
Figure 16E:
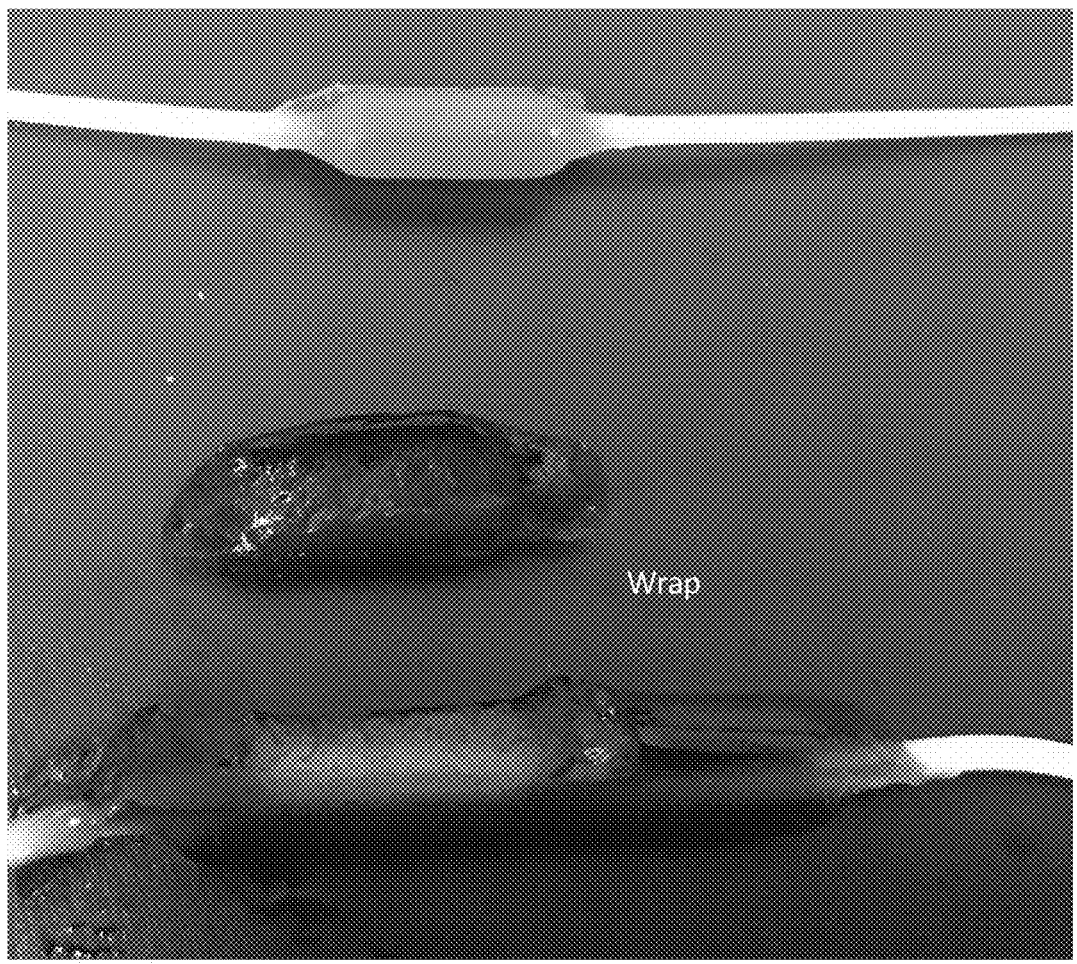

FIG. 16Ai-16E illustrate hydrogel filling and surrounding a nerve in a cap form. FIG. 16B illustrates a photograph of the hydrogel formed inside a cap form. FIG. 16C illustrates a high resolution image of a cap form. FIG. 16D illustrates an example of a cap form and wrap forms around the pig sciatic nerve. Example of a growth permissive hydrogel (pink) in a wrap form around a nerve and then subsequently embedded in a second (blue) growth inhibitory hydrogel wrap. Hydrogels are cut in cross section in order to see the growth permissive (pink) hydrogel embedded within the growth inhibitory (blue) hydrogel, as shown in FIG. 16E.

Figures 17A, 17B:
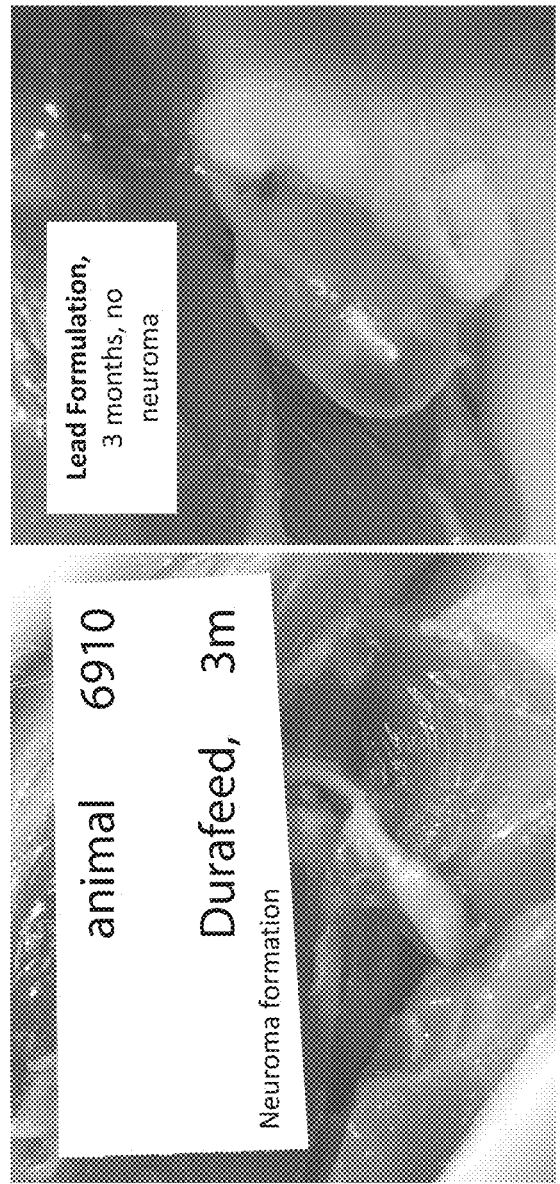
FIGS. 17A-17B illustrate preclinical data demonstrating the formation of neuroma after the delivery of hydrogels with adequate initial mechanical strength but inadequate in vivo persistence relative to hydrogels with longer duration mechanical strength and persistence.

FIG. 17A illustrates neuroma formation after delivery of DuraSeal in a cap form around a transected rat sciatic nerve. FIG. 17B illustrates the absence of neuroma formation after delivery of the lead formulation around a transected rat sciatic nerve. Cap form maintains mechanical strength and in vivo persistence of 3 months.

FIGS. 18A-18B schematically illustrates an embodiment of a mixing element to mix a two-part hydrogel system. In some embodiments, one static mixer 1800 delivers the hydrogel precursor solution into a central chamber, permitting the backflow and recirculation of the initial material coming out of the mixer. A second static mixer captures the well mixed solution and delivers it through the needle tip. The fluid entrance 1802 (from a dual chamber applicator) and fluid exit 1804 (to a blunt needle) are also shown.

The table to follow is related to specific non-limiting embodiments and devices for delivering in situ forming hydrogels.

| Delivery of in situ forming Hydrogels to: | Form Shape Selected | Hydrogel |
|---|---|---|
| 1) Undamaged nerves | Wrap | Growth Inhibitory |
| 2) Nerves that have been compressed, contused or stretched | Wrap | Growth Inhibitory |
| 3) Stump neuroma or transected nerve that can not be repaired | Cap | Growth Inhibitory |
| 4) Nerves that have been transected and undergone direct suture repair (coaptation, end-to-end anastamosed) | Wrap | Growth Permissive and then Growth Inhibitory |
| 5) Nerves that have undergone suture repair and placement in a nerve conduit or wrap | Wrap(s) - protect nerve-conduit junction | Growth Permissive and then Growth Inhibitory |
| 6) Nerves that have undergone connector assisted 'suturelesss' neurorraphy in which sutures are placed between the epineurium and the connector but not to one another | Wrap(s) - protect nerve-conduit juncton | Growth Permissive and then Growth Inhibitory |
| 7) Nerves that have been placed in a connector without suturing | Wrap(s) - protect anastamoses | Growth Permissive and then Growth Inhibitory |
| 8) Nerves that are undergoing conduit detensioning gap repair | Wrap(s) protect nerve-conduit junction | Growth Permissive and then Growth Inhibitory |

-continued

| Delivery of in situ forming Hydrogels to: | Form Shape Selected | Hydrogel |
|---|---|---|
| 9) Nerves undergoing detensioning allograft interposition with connector assisted sutureless repair | Wraps(s) - protect nerve-nerve anastamoses | Growth Permissive and then Growth Inhibitory |
| 10) Nerves undergoing detensioning autologous nerve graft interposition suture repair | Wrap(s) - protect nerve- nerve | Growth Permissive and then Growth Inhibitory |
| 11) Nerves that have non-union gaps (e.g. cannot be repaired directly) | 2 Wraps | Growth Permissive and then Growth Inhibitory |
| 12) Nerves that have been repaired and one or more wraps are placed around the anastomoses site | Wrap(s) - Protect nerve-wrap | Growth Permissive and then Growth Inhibitory |
| 13) Nerves undergoing suture repair in targeted muscle reinnervation | Wrap - Protect nerve-nerve interface | Growth Permissive and then Growth Inhibitory |

Peripheral Nerve Stimulation (PNS). As neurostimulators have advanced from the spine to the periphery and the hardware has been miniaturized, purpose built peripheral nerve stimulators are being developed and advanced for blocking pain, stimulating muscle contractions, and stimulating or blocking nerves to modulate disease and/or symptomatology, and stimulate nerve regeneration. As new applications and new neurostimulators have been developed, so has an increased awareness of the need to be able to maintain the stimulation electrodes and catheters in direct or close apposition with the target nerve as 1) placing the electrodes next to the nerve procedurally can be challenging and electrodes can migrate procedurally even after ideal placement adjacent to a nerve and 2) after placement, electrodes may drift through patient movement or handling as muscles contract or the implant gets better seated within the tissue. This can lead to loss of the therapy reaching the target nerve and thus loss of efficacy.

Percutaneous delivery. With the advent of higher resolution handheld ultrasound and better training amongst interventional pain physicians, percutaneously delivered implantable neurostimulators are increasingly being used as an alternate method to treat chronic pain. In one embodiment once an electrode has been placed adjacent to a nerve using a percutaneous delivery system, the position of the electrode next to the nerve can be maintained by delivering approximately 0.1 to 3 cc of an electroconductive hydrogel to form around the electrode and maintain it in close apposition with the nerve. The hydrogel media can be delivered through the lumen of the catheter delivery system or the lumen of the electrode and will form in situ. In some embodiments, the surface of the electrode can be designed such that it interfaces is rougher, permitting stronger intercalation between the hydrogel and the electrode to prevent lead migration. In other embodiments, a coil or other screw like design is placed on the end of the electrode to provide better purchase between the electrode, the hydrogel, and the surrounding tissue. For the percutaneous applications, delivery of a growth inhibitory hydrogels or hydrogels with medium to long duration mechanical strength are desirable. Again, longer-term the maintenance of mechanical strength to maintain the position of the electrode within the hydrogel is desirable until the chronic foreign body response is sufficient to hold the electrode in place. For example, to maintain longer term lead placement, the selection of crosslinked PEG hydrogels containing more stable ester, urethane or amide linkages is desirable, such as PEG-SG, PEG-SC, or PEG-SGA.

In still other embodiments, the neurostimulators are injectable wireless implants and takes the form of a pellet, rods, beads, a wrap a sheet or a cuff that are held in place with a hydrogel adjacent to a nerve, ganglia, or plexus. In one embodiment, the hydrogel is delivered first to the target site and the neurostimulator is delivered into the hydrogel. In another embodiment, the neurostimulator implant(s) is delivered first, adjusted to the desired location and then the hydrogel is then delivered around it to secure it in the desired location. Similarly, the neurostimulator implant location may be adjusted using an external magnet to orient the implant adjacent to or in contact with the nerve or neural tissue. In this embodiment, the gelation time can be adjusted to provide sufficient time for the appropriate alignment of the neurostimulator. In some embodiments, a plurality of injectable microstimulator implants are injected into a degradable or non degradable in situ forming hydrogel. In yet another embodiment, microstimulators in the form of micro or nanorods are implanted in the growth permissive hydrogel between the two nerve stumps to promote neurite extension and accelerated regeneration. These microstimulators may deliver magnetic, chemical, or electric fields to stimulate nerve regeneration through the gel and potentially along the microstimulator implants. In one embodiment, the microstimulators are nanofibers and can be injected through a low gauge needle or catheter to the nerve. In another embodiment, short- or long-acting microstimulators can be delivered with an injectable biocompatible biomaterial such as a hydrogel to form a neurostimulator anisogel. The microstimulators are magnetic, allowing directional control of the microstimulator implant and, for example, parallel alignment of the microimplants within the hydrogel prior to the gel converting from a precursor solution to a gel. These hydrogels would be injected around or in proximity to nerve bundles or tendrils and then the microstimulators may physically provide regions across which they can grow to and orient along as well as providing chemical, electrical, or magnetic field stimulation to support neurite outgrowth.

Open surgical. For open surgical applications, the hydrogel may also be deposited in a similar manner around the electrode with the electrode in direct contact and/or adjacent to the nerve under direct visualization. Again, deposition of approximately 0.5 to 1 cc of hydrogel is sufficient to maintain the electrode position relative to a nerve. The electrode can be inserted into a groove in the silicone form adjacent to and with the nerve prior to the delivery of the hydrogel. Forms can be envisioned that have a second entrance region for the electrode. In this manner, for example, the electrode can be aligned to run parallel to the nerve or in direct apposition to the nerve when the gel is applied. For applications where the neurostimulation therapy is only required for a day to several weeks, pulling on the electrode will cause it to be removed from the hydrogel with relative ease. Utilizing combinations of growth inhibitory and growth permissive hydrogels described above, may be selected depending on the application. For examples in which electrodes placed next to the nerve only need to stay in place for a matter of days or weeks, a shorter term degradable hydrogel may be employed. This provides sufficient time for the hydrogel to remain in place while the therapy is delivered and then be rapidly cleared from the tissue. One example of this would be the selection of crosslinked PEG hydrogels containing more reactive ester linkages such as PEG-SS or PEG-SAZ. These hydrogels are electrically conductive and thus suitable for applications involving neurostimulators.

Generally, the selection of low swelling formulation is critical to maintain apposition with the electrode; in one embodiment, the hydrogel swelling is less than 30%, more preferably less than 20% in order to maintain apposition with the nerve and the electrode.

In yet another embodiment, the in situ forming hydrogel can be used to secure a convection enhanced delivery system to the site. Like the implantable neurostimulator, a drug delivery catheter can be secured approximately 10 mm proximal to an injury nerve site with the tip approximately 5 mm from the nerve injury. Like the implantable neurostimulator, the silicone form can be designed to include an entrance zone or cut out of the top edge of the silicone form to permit the catheter or stimulator lead to rest in the form in preparation for addition of the hydrogel. After delivery of therapy (neurostimulation, convection enhanced drug delivery), the catheter or neurostimulator can be removed from the hydrogel without disrupting the protective barrier around the hydrogel. For example U.S. Pat. No. 9,386,990 teaches the use of DuraSeal to repair nerves with an in vivo persistence of two to four weeks, the hydrogel does not provide the sustained mechanical strength necessary to prevent neuroma formation or detension a nerve during regeneration, such as at 3 and 4 months after surgical repair. For example, crosslinked multi-arm PEGs containing rapidly degrading ester linkages such as PEG-SS or PEG-SG are well-suited suitable for applications to prevent the acute and subacute adhesion formation. For another example, low molecular weight linear PEGs have been demonstrated to act as a fusogen and promote nerve repair and regeneration when injected around injured nerves (but do not provide mechanical strength or persistence to prevent neuroma formation. For example, PEG hydrogels, such as PEG tetraacrylate hydrogels, have been used to rejoin nerves in preclinical models (Hubbell 2004/0195710)

None of the previous examples contain the degradable linkages necessary to support the required mechanical strength or in vivo persistence required for applications to prevent aberrant nerve outgrowth and neuroma formation. Commercially available PEG hydrogels, particularly conventional PEGs with a hydrolytic ester linkage, do not have the suitable mechanical strength or in vivo persistence to prevent neuroma formation or detension a nerve for three of four months until the nerve is repaired. These PEGs and PEG gels may have sufficient mechanical strength initially to temporarily assist in the repair of nerves across an anastomoses and/or prevent adhesion formation, but the hydrogels do not have sufficient mechanical strength at two months, or more preferably three months post administration to prevent aberrant neuroma formation (cap) and continue to provide mechanical offloading to support to a regenerating nerve (wrap). FIG. 16 provides an example of the lack of durability of the DuraSeal hydrogel in preventing neuroma formation in a rat sciatic nerve transection model. The hydrogels containing ester linkages have either degraded sufficient that they no longer provide a barrier to nerve regeneration, have fallen off the nerve, or have been cleared entirely. As a result, the initial mechanical barrier was not sufficient to act as a long-term barrier to prevent nerve outgrowth and neuroma formation.

Furthermore, the other approaches teach delivering the an in situ forming hydrogel around the nerves directly without protecting the underlying muscle from adhesions or providing a method to systematically circumferentially cover the proximal nerve tip with hydrogel. In situ forming polymeric systems adhere to, albeit with varying to degrees, to the surrounding tissues that they come into contact with during crosslinking or polymerization. If the non-target tissue (e.g. muscle or fascia) is not protected or shielded from the reaction, the hydrogel also adheres to this tissue. Since nerves glide freely within a fascial plane, typically between muscles, limitation to their movement is not desirable and may result in pain and or loss of efficacy. Some embodiments described here provide forms that separate the in situ forming hydrogel from the surrounding environment, preventing tethering between the nerve and the surrounding tissue and permitting the nerve to glide within the fascial tunnel.

Nerve blocking. In order to block nerve regeneration, the in situ forming biomaterial needs to have the physical properties to prevent nerves from migrating into the biomaterial including negative or neutral charge, smaller pore size, hydrophillicity and/or higher crosslinking density. Although most studies are focused on materials through which nerves regenerate, several studies have documented the biomaterials through which nerves will not grow, including poly (ethylene glycol)-based hydrogels, agarose- and alginate-based hydrogels, particularly at higher concentrations of the polymers. Higher concentrations typically have higher crosslinking density and thus smaller pore size. These hydrogels can be employed for their ability to prevent neurite outgrowth in vitro and in vivo by virtue of their charge, inert surface, hydrophilicity, and pore size. One example of this agarose, in which nerves will not extend across the biomaterial above concentrations of 1.25% wt/vol. In another example, PEG hydrogels can prevent neuroma formation at 4% w/v and higher. In other embodiments, even positively charged or natural in situ forming biomaterials can provide a barrier to nerve regeneration if the solid content and crosslinking density are such that the pores are too small for cellular ingrowth.

In order to prevent neuroma formation, the in situ forming biomaterial needs to provide the requisite mechanical strength to act as a barrier to nerve regeneration for two months, more preferably three months or more. Many in situ forming gels, including commercially in situ forming PEG hydrogels with biodegradable ester linkages, may have sufficient mechanical strength initially but hydrolyze at such a rate that their crosslinks have broken sufficient that their mechanical strength at 1 to 2 months is not sufficient to prevent neuroma formation (See Table 1). In vivo experiments in a rat sciatic nerve model demonstrated the formation of bulbous neuromas at between one and three months after delivery of these hydrogels around the end of a transected nerve stump. Preclinical testing has demonstrated that a mechanical strength of at least 10 kPa, more preferably 20 kPa or more is necessary to prevent neuroma formation. At three months, in vivo studies have demonstrated that these hydrogels have been full degraded and cleared from the site or have lost their mechanical integrity sufficient that the nerve has grown out into the soft, collapsed and/or fractured gels and formed a neuroma. Thus, although the prior art teaches the use of PEG hydrogels for the purposes of nerve repair, not all hydrogels are suitable to support the long-term mechanical strength and persistence requirements necessitated to prevent neuroma formation and aberrant nerve outgrowth. Preferably the barrier has an in vivo persistence of at least about two month or at least about three months, preferably four months or more depending upon the desired clinical response to reduce chronic neuropathic pain after surgery. The mechanical integrity of the hydrogels at various points in vitro and in vivo can be assessed through compression testing, described further below.

Persistence The in vivo persistence of biodegradable hydrogels is related to the crosslinking density and thus the mechanical integrity of the hydrogel. For applications to prevent neuroma formation, the hydrogel degradation must be sufficiently slow that the hydrogel does not lose significant structural integrity during the weeks to months during which the nerves are attempting to regenerate, which occurs over approximately 3 months and may be 6 months or more in humans. In this manner, the persistence of the hydrogel and the persistence of the mechanical integrity of the hydrogel is critical to providing ongoing protection and padding from neuroma and aberrant nerve outgrowth preferably for 3 months or more, preferably 4 months or more. In embodiments utilizing a degradable hydrogel, the mechanical strength must be maintained for longer than 2 months, preferably 3 months and thus there must be no substantial degradation of the hydrogel for this period of time, preferably 3 months or more. Similarly, the persistence of the mechanical integrity and, in turn, the hydrogel is critical to the ongoing offloading provided by the hydrogel around the nerve-nerve or nerve-graft interface for a period of preferably 2 months, more preferably 3 months as even nerves that have been directly sutured to one another through direct coaptation still have not regained their original strength (nerves have approximately 60% of original strength at 3 months after a transection).

The development of in situ forming polymers, and particularly, in situ forming synthetic hydrogels, including PEG-based hydrogels with longer in vivo mechanical strength and longer persistence profiles beyond 2.5 months but less than 12 months is challenging. For example, there is a significant gap between the in vivo persistence of PEG hydrogels with biodegradable esters (weeks to less than 3 months) in and around the surgical environment of the nerve and PEG hydrogels containing biodegradable urethane or amide bonds, with degradation profiles in this subcutaneous extramuscular location on the order of 9 months to 18 months or more. Some embodiments focus on in situ forming polymers, preferably multi-arm PEGs, with the requisite mechanical strength and persistence to prevent neuroma formation. In particular, the swelling, mechanical strength and in vivo persistence of PEG hydrogels are described to permit the long-term safety and efficacy in applications requiring the long-term prevention of aberrant nerve outgrowth and the ability to detension and offload nerves over a period of months after the surgical repair.

In order to obtain a suitable in vivo mechanical strength and persistence, conventional PEG hydrogels containing a degradable ester linkers that are widely available commercially as dural and lung sealants are not suitable for applications around nerves given their loss of mechanical strength and/or clearance within a couple months. Simply, degradation occurs at a rapid enough rate that mechanical integrity can not be maintained for sufficient time, making these hydrogels suitable for anti-adhesion prevention but not the prevention of nerve outgrowth. In embodiments utilizing a nondegradable PEG hydrogel, the mechanical strength of the hydrogel is based on the initial mechanical strength of the hydrogel as the crosslinks do not degrade over time. In vitro and in vivo testing of a range of hydrogel with various molecular weights, degradable linkages, crosslinking densities demonstrated that only hydrogels with sufficient mechanical strength at 3 months (and with this, in vivo persistence) were able to prevent neuroma formation. Examples of hydrogels, degradation times, and formation of neuromas are provided in the table below. FIGS. 16Ai-16Aiii illustrate the formation of a neuroma after the delivery of DuraSeal.

Examples of Multi-Armed PEG Hydrogels with Various Hydrolytically labile bonds

| PEG Hydrogel | In Vivo Persistence | Neuroma formation in Rat Sciatic Nerve Transection Model |
|---|---|---|
| PEG-SS (ester bond) | 2 weeks | Large bulbous neuroma observed at 1 month |
| Duraseal (ester bond) | 2 to 8 weeks | Large bulbous neuroma formation observed at 2 and 3 months |
| PEG-SG (ester bond) | 4 to 8 weeks | Large bulbous neuroma formation observed at 3 months |
| PEG-SAP (ester bond) | 6 to 8 weeks | Large bulbous neuroma formation observed at 2 and 3 months |
| PEG-SAZ (ester bond) | 2-3 weeks | Large bulbous neuroma at 2 and 3 months |
| PEG-SGA (amide bond) | 9 months or more | No neuroma formation |
| PEG-SC (urethane bond) | 6 months or more | No neuroma formation |

In vivo persistence refers to the absence of significant absorption of the biomaterial, such as less than 25% resorption, preferably less than 15% at a given time point. Depending on the biomaterial, this can be assessed by mass loss, loss of cross-linking density, or change in the form of the biomaterial. Active bonds that have more extended degradation in vivo such as the PEG-ureas (e.g. PEG isocyanate, PEG-NCO), PEG-urethanes (PEG-succinimidyl carbonate) (PEG-SC) and PEG-carbamate. Hydrogels comprised of polyethylene glycol succinimidyl carbonates (PEG-SCs) with more than 2 arms, such as the 4-arm, 6-arm, or 8-arm PEGs with molecular weights ranging from 1K to 50K, preferably 10K to 20K, such as 10K, 15K or 20 kDa. In some embodiments, the 4-arm 10K PEG-SC, 4-arm 20K PEG-SC, 8-arm 10K PEG-SC, 8-arm 15K PEG-SC, or 8-arm 20K PEG-SC are selected, more preferably 4-arm 10K PEG-SC or 8-arm 20K PEG-SC. The following patent is incorporated for reference 20160331738A1.

Compressive Strength.

The desired compressive strength (elastic modulus, Young's modulus) of the hydrogel is greater than 10 kPa, preferably greater than 20 kPA, preferably greater than 30 kPa. In the preferred embodiment, the compressive strength of the is greater than 10 kPa after 3 months in vivo, more preferably 40 kPa at 3 months after administration.

Compressive strength was measured benchtop after in vitro equilibrium and also after harvesting implanted samples from the subcutaneous space in rats, in which hydrogel cyclinders (d=6 mm) are cut to 100 mm long, pre-equilibrated (for 12 hours at 37° C.) and evaluated for compressive strength. Compressive properties of the hydrogel formulations were measured at a 1 mm/min with the Instron. The modulus was calculated as the tangent slope of the linear region between 0.05 and 0.17 of the stress-strain curve.

Compressive Strength of Various Formulations

| Polymer | Compressive modulus (t = 0) | Compressive modulus (t = 3 months, in vivo) | Neuroma formation |
| --- | --- | --- | --- |
| Formulation G | 20 kPa | 5 kPa | Neuroma formation |
| Formulation H | 12 kPa | 8 kPa | Neuroma formation |
| Formulation I | 1 kPa | 1 kPa | Neuroma formation |
| Formulation I | 25 kPa | 17 kPa | No neuroma formation |
| Formulation J | 72 kPa | 55 kPa | No neuroma formation |

Although in vitro mechanical strength and persistence of the hydrogels (37° C., PBS) typically does not correlate well with in vivo persistence, the maintenance of mechanical strength of the hydrogels at 3 months in vitro is a strong indicator of the ability of the hydrogel to provide a sustained mechanical barrier to nerve regeneration in vivo.

In some embodiments a cleavable carbamate, carbonate, or amide linker in a biodegradable hydrogel permits a more stable slowly degrading bond to maintain the requisite mechanical strength to prevent nerve outgrowth for three months or more and, with this, the in vivo persistence to provide the sustained mechanical barrier to nerve regeneration.

Generally, the structure of multi-armed PEGs are

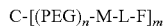

where
C=core structure of the multi-arm PEG
n=repeating units of PEG on each arm (25 to 60 units)
M=Modifier
L=cleavable or noncleavable linker (ester, urethane, amide, urea, carbamate, carbonate, thiourea, thioester, disulfide, hydrazone, oxime, imine, amidine, triazole and thiol/maleimide).
F=reactive functional group for covalent crosslinking, e.g. maleimide, thiol or protected thiol, alcohols, acrylates, acrylamides, amines, protected amines, carboxylic acids or protected carboxylic acids, azides, alkynes, 1,3-dienes, furans, alpha-halocarbonyls, and N-hydroxysuccinimidyl, N-hydroxysulfosuccinimidyl, or nitrophenyl esters or carbonates
m=number of PEG arms (e.g. 2, 3, 4, 6, 8, 10)

In some embodiments, hydrolysis modifiers (M) can be incorporated into the backbone of the hydrogels to slow the hydrolytic degradation of the ester bonds (L) in the hydrogel. This can be accomplished with electron donating groups which regard the reaction or by increasing the length of the carbon chain adjacent to the ester bond in order to increase the hydrophobicity and shield the bond from hydrolysis. For example, PEG-SAP, PEG-SAZ are examples of PEG-ester bonds with longer carbon chains than PEG-SG. In another embodiment, an aromatic group is placed next to the ester group to provide additional stability of the ester bond against hydrolysis, such as a PEG-aromatic carboxyl ester, including a benzoic acid ester or a substituted benzoic acid ester.

In some embodiments, a more stable or slowly degrading bond such as a urethane bond or amide bond may be selected to provide the requisite mechanical strength and in vivo persistence to prevent the neuroma from forming.

In other embodiments, hydrolysis modifiers (M) can be designed in the backbone of the hydrogels to increase the hydrolytic degradation of urethane in the hydrogel. This can be accomplished with the addition of electron withdrawing groups which accelerate the reactions.

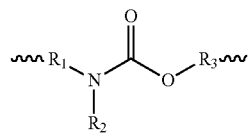

In one embodiment, the hydrolysis rate of carbamate bond can be modulated by the adjacent groups, thus modulating the persistence of hydrogel in vivo. R1 and R3 can be any aliphatic hydrocarbon group (—CH$_2$—, —CHR—, —CRR'—), substituted aliphatic hydrocarbon group, aromatic groups and substituted aromatic group in any arranged forms. The aromatic group includes but not limit to phenyl, biphenyl, polycyclic aryls and heterocyclic aryls. The substitution moiety for aliphatic and aromatic group include but not limit to halogen, alkyl, aryl, substituted alkyl, substituted aryl, substituted heteroaryl, alkenylalkyl, alkoxy, hydroxy, amine, phenol ester, amide, carboalkoxy, carboxamide, aldehyde, carboxyl, nitro and cyanide. R2 can be H and any group in R1 and R3. In addition, R1 can include isocyanate, aromatic isocyanate, diisocyanate (e.g. LDI). In one embodiment, R3 can be Anilide and in another embodiment R1 can be phenyl.

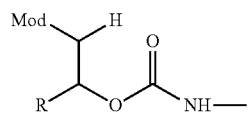

In another embodiment, the hydrolysis rate of carbamate bond can be modulated by the modulator at the beta position. The modulator can be CF$_3$PhSO$_2$—, ClPhSO$_2$—, PhSO$_2$—, MenPhSO$_2$—, MeOPhSO$_2$—, MeSO$_2$—, O(CH$_2$CH$_2$) NSO$_2$—, CN—, (Et)$_2$NSO$_2$—. In yet other embodiments, these modifiers can be adapted for use in PEG hydrogels containing amide, carbonate and urea linkages. Additional modifiers that affect the hydrolysis rate of the carbamate linkage are described in U.S. Pat. No. 7,060,259, incorporated for reference herein. Additional cleavable crosslinks are described in Henise et al (2019) In vitro—in vivo correlation for the degradation of Tetra-PEG-hydrogel-microspheres with tunable b-eliminative crosslink cleavage rates. International Journal of Polymer Science, incorporated in entirety. These modifier groups, M, can be on the backbone itself or a nearby side chain such as with a beta-eliminative linker as described by D. V. S anti et al (2012) Predictable and tunable half-life extension of therapeutics agents by controlled chemical release from macromolecular conjugates. PNAS, 109(6) 6211-6216 and US20170312368A1 incorporated herein for reference. In some embodiments, a soft chain extender is added, such as an amino acid-peptide based chain extender with ester linkages. For example poly (phosphoester urethanes) with chain extenders containing phosphoester linkages. For example poly (DL, lactide) is a chain extender or poly (caprolactone) to extend the PEG chain and add a soft segment. Preferably the molecular weight of the chain extender may be 0.5 kDa to 5 kDa, preferably 1 to 2 kDa, more preferably 2 kDa. The soft segments can provide additional properties to enhance the physical properties of the hydrogel including the thermosensitivity, crystallinity, potential resulting in physical in addition to chemical crosslinking. These hydrogels may be comprised of, for example, PEGs with molecular weight between 1,000 Da and 50 kDa including multi-arm PEG-succinimidyl carbonate (4-arm or 8-arm) with molecular weights of 5 to 40 kDa and arm lengths between 1 and 3 kDa, and PEG-amine (4-arm or 8-arm) with molecular weights between 5 to 40 kDa, preferably 10 or 20 kDa. In one embodiment, PEG-SC (4-arm 10K) is crosslinked with PEG-amine (8-arm 20 k). In another embodiment, PEG-SC (8-arm 15K) is crosslinked with trilysine amine. In another embodiment, PEG-SC (4-arm 20K) is crosslinked with trilysine amine. Examples of other in situ forming PEG-SC formulations are described in U.S. Pat. No. 6,413,507, incorporated herein for reference. In another embodiment, a 4-arm PEG succinimidyl glutaramide 4-arm 10K (PEG-SGA) may used in combination with 8-arm PEG-amine 20K at 8% solid content.

Alternatively, the functionalized PEG urethanes and esters may be covalently crosslinked with another reactive polymer or small molecule (e.g. trilysine) containing amines or protected amines, maleimides, thiols or protected thiols, acrylates, acrylamides, carboxylic acids or protected carboxylic acids, azides, alkynes including cycloalkynes, 1-3 dienes and furans, alpha-hydroxycarbonyls, and N-hydroxysuccinimidyl, N-hydroxysulfosuccinimidyl, or nitrophenyl esters or carbonates.

In yet other embodiments, blends of faster degrading PEG-esters and slower degrading PEG-SGA or PEG-SC with ratios of 10:1 or 5:1 may permit slowing of the in vivo degradation profile. Similarly, blends of multi-arm PEG-SC and PEG-amine that crosslink to form carbamate bonds and PEG-carbonate ester bonds (delayed reaction of PEG-SC and with hydroxyl functional groups) to form blended 60:40 hydrogels (Kelmansky et al (2017) In Situ Dual Cross-Linking of Neat Biogel With Controlled Mechancal and Delivery Properties. Molecular Pharmaceutics, 14(10) 3609-3616.

In yet other embodiments, multi-arm PEGs can be combined with blocks of other hydrolytically degradable polymers that can be used to tailor the degradation time of the PEG hydrogels. For example, soft segments with diblock with polyester or triblocks can be synthesized with low molecular weight polyester regions to permit the hydrogel to be formed in an aqueous environment (polycaprolactone, polylactic acid, polyglycolic acid, polyurethane, polyhydroxyalkanoates (PHA), poly(ethylene adipate) (PEA), alipathic diisocyanates such as isophorone diisocyanate (IPDI) or L-lysine ethyl ester diisocyanate (LDI)). These blocks can be comprised of lactide, glycolide, or caprolactone regions can, depending on the degree of crystallinity (D,L or L,L) be used to provide additional mechanical strength to the hydrogels permit tuning of the degradation profile. For example, a block of caprolactone can be added to a multi-arm PEG which each arm comprising a PEG-PCL-NHS ester. In this embodiment, the PCL domain may extend the degradation of a previously poor in vivo persistent multi-arm PEG with hydrolytic ester linkages. In the preferred embodiment, a PCL block of between 1 and 5 kDa, preferably 1 to 2 kDa is added on the PEG arm. For example, a 4-arm 28K PEG-PCL-NHS ester may react with an 4-arm 10K PEG-amine to form a crosslinked hydrogel in situ, where the PEG is a 2K block. The addition of the block renders the hydrogel in situ forming both through chemical and physical crosslinking. Amino acids can also be incorporated as chain extenders in the PEG-SC to improve the degradation of the PEG-urethane. In some embodiments low molecular weight trifunctional polyester polyols are selected for incorporation. Please refer to FIG. 1—common monomers used for synthesis of biostable and biodegradable polyurethanes, incorporated herein for reference (Chapter: Degradation of Polyurethanes for Cardiovascular Applications, Book: Advances in Biomaterials Science and Biomedical Applications).

In some embodiments heterobifunctional crosslinkers are used to enable polyesters to be conjugated to some arms and NHS esters or other functional group with other arms.

In yet other embodiments, excipients may be incorporated into the hydrogels to modify the mechanical strength, density, surface tension, flowability, and in vivo persistence of the hydrogels. These modifiers are encapsulated in the hydrogel when the hydrogel is formed. Modifiers may include amphiphilic excipients such as vitamin E TPGS, low molecular weight polyesters such a caprolactone or solvents such as ethanol. In one embodiment, ethanol is incorporated in the diluent or accelerator solutions to yield a 5% to 70% v/v ethanol loaded hydrogel. The ethanol improves the elasticity of the hydrogel and reduces the density of the hydrogel precursor solution relative to the nerve density. Further more, low concentrations of ethanol may be incorporated in the hydrogel to improve the pot or functional life of the PEG/diluent solution after PEG powder suspension. In another embodiment, Pluronic may be incorporated in diluent or accelerator solution to yield a 5 to 15% w/v to yield a PEG-SG hydrogel with improved elasticity and in vivo persistence. In yet another embodiment, low molecular caprolactone is incorporated into diluent solutions to yield a 1 to 5% w/v PEG/caprolactone blended hydrogel. In another embodiment, vitamin TPGS can be incorporated into the diluent solution to yield a 5 to 20% w/v of PEG/vitamin E TPGS blend.

Swelling Another critical element of these hydrogels is the swelling of the hydrogels for applications around nerves. The hydrogels, when delivered circumferentially around an object such as a nerve, undergo positive swelling in an outward radial direction. Initially, the hydrogels undergo equilibrium-mediated swelling as they equilibrate with the fluids in the surrounding environment, and, later, when a critical number of hydrolytic bonds have broken, the hydrogels swell as a result of loss of mechanical strength. This latter phase of degradation-mediated swelling results in the progressive loss of mechanical strength and hydrogel softening that the hydrogel collapses and is ultimately cleared from the site. In vivo experiments in which transected rat sciatic nerves were surrounded within hydrogels that swelled 5%, 10%, 20%, 30% and 60%, demonstrated that hydrogels that swell more than 30% were significantly more likely to fall off of the nerve as a result of the creation of a gap between the nerve and the hydrogel. Of note, PEG hydrogels that swell at or less than 0%, shrink when equilibrating in vitro or in vivo and the resultant compression may result in persistent hydrogel-mediated local nerve pain. For example, the DuraSeal hydrogel swells significantly and have a tendency to fall of the proximal nerve stump when delivered in situ.

Equilibrium swelling. For applications in which hydrogels are delivered to nerves to prevent nerve regeneration, maintaining close adherence and apposition between the nerve and the conformable hydrogel is desirable. As a result, minimizing the equilibrium swelling post-hydrogel delivery is desirable. The equilibrium swelling occurs during in the minutes to days as the hydrogel equilibrates with the fluids in the in situ environment. In one embodiment, the hydrogel swells greater than 0% but less than 40%, preferably greater than 5% and less than 30%, more preferably greater than 5% and less than 25%.

Furthermore, in some embodiments, it is desirable to avoid hydrogels that shrink as these hydrogels may compress the nerve and result in aberrant nerve firing and therefore it is preferable to use hydrogels that swell greater than 0%. In addition, the nerve may swell after injury, and so some swelling is desirable to permit some space for the nerve to swell.

Equilibrium swelling may be preferably assessed in vitro at body temperature conditions (37° C. in PBS). Hydrogel samples were prepared in cylindrical silicone tubing (6 mm) and cut to dimensions of 6 mm diameter by 12 mm length. Samples were weighed and merged into PBS at 37° C. After swelling in PBS for 12 to 24 hours at 37° C., samples were taken out and weighted again. The swelling is calculated by the percentage of mass increase.

Degradation swelling. A secondary characteristic in biodegradable or bioerodible hydrogels, after the initial equilibrium swelling, is an appreciation for a second ongoing phase of swelling that occurs as a result of the degradation of the hydrogel. The swelling may occur through the hydrolytic, enzymatic, or oxidatively-sensitive bonds in the hydrogel. This is an equally important characteristic because the hydrogel needs to remain on the nerve for a period of one month or more, more preferably two months or more, more preferably three months. In an animal model, the period of time is shorter and in the clinical setting this period is longer. In some instances, if the degradation rate is too rapid, the hydrogel may fracture and fall off the nerve or be cleared before the hydrogel can serve the function to prevent nerve outgrowth and/or neuroma prevention. In other instances, if the hydrogel appears intact on the nerves, there may be a substantial loss of the mechanical integrity within the hydrogel as a result of degradation that the nerve may extend out into the softened or fractured hydrogel and form a neuroma formation. As a result, it is preferable that a biodegradable system have no more than 50% of the hydrolytically labile linkages cleaved at 3 months, more preferably no more than 30% of the linkages, and even more preferably no more than 20% of the linkages. After the period of time in which the hydrogel provides a mechanical barrier to nerve regeneration, the crosslinking density can drop and the degradation can continue until the hydrogel is entirely cleared. The loss of bonds can be evaluated in part through the reduction in the mechanical integrity of the hydrogel. The loss of bonds can be evaluated in part through the reduction in the mechanical integrity of the hydrogel. Thus, it is desirable that the hydrogel maintain a compression modulus of 40 kPa at 3 months post delivery, this hydrogel is sufficiently stiff that nerves will not grow through it.

Pressure. In addition to ensuring that the swelling is not so great that the hydrogel falls off of the nerve, confirmation that the swelling (or low swelling, shrinkage) will not result in nerve compression is also desirable. In one experiment, a pressure transducer catheter was placed next to a nerve and an in situ forming hydrogel was delivered to form around the nerve/pressure transducer (Millar Mikro-Tip pressure catheter, 3.5 F, single straight, AD Instruments). The hydrogel was then placed at 37° C. in PBS and measurements of the pressure as a function of time were taken. Hydrogels with approximately 0% or negative swelling resulted in high and sustained increases in the pressure (>80 mmHg) exerted on the embedded nerve whereas hydrogels that swelled 10% or more did not result in any significant increases in pressure (~20 mmHg). In the preferred embodiment, the pressure reading after equilibrium swelling is around 5 mmHg In preclinical and clinical models, pressure at the site of nerve damage may be between 5 and 15 mmHg (Khaing et al 2015—Injectable Hydrogels for Spinal Cord Repair). For example, although a variety of materials have been evaluated for modulating nerve regeneration in a spinal cord model, the majority do not have the requisite linear compressive modulus (G) to prevent neuroma formation (Table 1, Khaing et al, 2015).

Stiffness. Stiffness of the hydrogel can measured/inferred either by rheology (G'=storage modulus, G*=shear modulus, or the linear compressive modulus (G). Preferably the stiffness of the hydrogels, as measured through the linear compressive modulus (G) is greater than 10 kPa, preferably greater than 30 kPa, more preferably greater than 50 kPa. The stiffness prevents nerve outgrowth into the surrounding hydrogel.

Compression and rebound. In addition to injectable gels that have minimal swelling, gels that are compressible are desirable. In this manner, even if the hydrogel implant is pressed, it will not fracture. Compression and rebound testing is performed on cylindrical samples (6 mm diameter, 10 mm long) that have been incubated for at least one hour at 37° C. until equilibrated. The samples are loaded into the Instron and a displacement perpendicular to the longitudinal axis of the cylinder will be applied at a crosshead speed of 1 mm/min to a final displacement of 60% of the diameter of the conduit. Verification that the hydrogels can withstand compressive forces of greater than 0.25N and that no changes in the shape and diameter have occurred after removal of the compressive forces.

Flexibility. Another critical parameter of these in situ forming polymers is the ability of the hydrogels to bend and flex at physiologically relevant angles in the body. To evaluate the flexibility of the hydrogels, the hydrogels were formed inside 0.1 to 0.25" inner diameter silicone tubing to form 12 to 24" long cylindrical hydrogel cables. Preferably, the hydrogels have sufficient flexibility to bend greater than 90° and more preferably cylindrical strands of hydrogel can be readily be tied into a knot. Since the flexibility and elasticity is determined, in part, by the distance between the core of one multi-arm PEG to the core of the adjacent multi-arm PEG, PEG hydrogels with core-to-core distances of 3 kDa, more preferably 5 kDa or more. Flexible robust hydrogels that will not fracture in the highly mobile and compressive environment of the body. As a result, more flexible hydrogels are desired such as combinations of the 4-arm 10K or 20 K PEGs with 4-arm or 8-arm 20K PEG-amines may be desirable.

Viscosity. Low and medium viscosity precursor solutions may be selected to encapsulate the hydrogel with generally better adhesion in the low viscosity solution and improved handling of the nerve in the medium viscosity precursor solutions. In one embodiment of the invention, the flowable media is a low viscosity hydrogel precursor solution, having a viscosity of no more than about 100 cP and in some embodiments no more than about 20 cP or no more than about 5 cP. In yet another embodiment, the flowable media is a medium viscosity hydrogel precursor solution, having a viscosity preferably 300 to 10 kcP, more preferably 300 to 900 cP. In one embodiment, a viscosity enhancer/modifier or thickening agent can be added to the gel precursor to modify the fluidic properties and help to positioning the nerve in the cap before gelling. The viscosity modifier can be natural hydrocolloids, semisynthetic hydrocolloids, synthetic hydrocolloids and clays. Natural hydrocolloids include but not limited to Acacia, Tragacanth, Alginic acid, Alginate, Karaya, Guar gum, Locust bean gum, Carrageenan, Gelatin, Collagen, Hyaluronic acid, Dextran, Starch, Xanthan gum, Galactomannans, Konjac Mannan, Gum tragacanth, Chitosan, Gellan gum, Methoxyl pectin, Agar, Gum arabic, Dammar gum. Semisynthetic hydrocolloids include but not limited to Methylcellulose, Carboxymethylcellulose, Ethyl cellulose, Hydroxy ethyl cellulose, Hydroxy propyl methyl cellulose (HPMC, 0.3%), Modified starches, Propylene glycol alginate. Synthetic hydrocolloids include but not limited to Polyethylene glycol, Polyacrylic acid, polyvinyl alcohol, polyvinyl pyrrolidone, polyglycerol, Polyglycerol polyricinoleate. Clays include but not limited to Magnesium aluminum silicate (Veegum), Bentonite, Attapulgite.

In another embodiment, viscosity can be modified by pre-crosslinking PEG-amine and PEG-urethane. PEG-amine and PEG-urethane can pre-crosslinked at a ratio from 10000:1 to 1:10000 at total PEG concentration of 0.01% to 100%. The pre-crosslinking can be further cross-linked by itself, or with PEG-amine, or with PEG-urethane, or with PEG-amine and PEG-urehtane to form a higher viscosity precursor solution.

Density of precursor solution. Nerve tissue, as a result of the myelin and adipose tissue, is hydrophobic and thus has a tendency to float in solutions with density approximating that of water (~1 g/cm$^3$). By adjusting the density of the flowable media, the nerve position can be adjusted to reduce the propensity of smaller diameter nerves to float up in the precursor solution without sacrificing adhesion strength that comes with increasing precursor viscosity. In some embodiments, the density of the precursor solution or media solution is decreased so that the nerve is relatively more dense than the solution to <1 g/cm$^3$, preferably <0.9 g/cm3. In still other embodiments, the density of the precursor solution is adjusted to be approximately equivalent to that of the nerve. Polar and less dense solvents can be added including ethanol (10 to 70%), toluene (10%), ethyl acetate or chlorobenzene to reduce the density of the precursor solution. In another embodiment, vitamin E TPGS (1-2 kDa, 10-20%) can be added to reduce the propensity of the nerve to float up. Some of these solvents also reduce the surface tension of the precursor solution, causing the nerve to sink.

Open Surgical Neuroma Procedure. After openly exposing the surgical site and isolating the target nerve, fresh transection of the nerve is desirable to clean up the nerve end. In some embodiments, the clinician may elect to transect the nerve at a 90 degree or, alternatively, a 45 degree angle. In some embodiments, the clinician may elect to use other methods such as electrocautery of the nerve end, ligation of the nerve stump, apply low molecular weight end-capped PEG (e.g. 1-5 kDa, 50 w/v % hypotonic solution) or other approaches that they have developed to seal or ablate the end of the nerve.

Axoplasm. As axoplasm, a viscous and sticky material that oozes from the end of the cut nerve after transection, may reduce close apposition between the nerve end and the hydrogel, it may be desirable to remove it from the nerve tip. This can be accomplished through the contact between the nerve and an absorbent material, such as a swab. An absorbable swab may be provided in order to absorb any of the axoplasm after nerve transection. The tip of the swab is preferably less than 5 mm, more preferably less than 2 mm in order that it may fit comfortably within the form and hold the nerve while the hydrogel is delivered. The swab may be provided as part of the kit. Alternatively, this can be accomplished by contacting the nerve tip with the surrounding tissue, which results in the rapid formation of an adhesion between the nerve and the tissue that must then be secondarily severed.

Coverage of the proximal nerve stump. The hydrogel itself preferably extends at least 0.5 mm, preferably 1 mm to 20 mm, preferably 2 mm to 10 mm beyond the end of the proximal nerve stump.

Length coverage. It is preferable that a minimum of 10 mm of nerve be embedded/encapsulated in the hydrogel although, in some instances, 5 mm may be sufficient. A greater length of nerve embedded in the hydrogel accomplishes several things a) increased surface area of apposition between the nerve and the hydrogel and b) decreased likelihood of proximal sprouting from nodes of Ranvier proximal to the transection as these proximal nodes are embedded in hydrogel. Again, the greater the length of nerve encapsulated, the higher the likelihood that even the regions that were damaged through handling with forceps, previous trauma, etc. are embedded in the hydrogel, thereby preventing sprouting of nerve fibers.

Once an approximately 10 mm section of nerve is isolated, whether the nerve is adherent to the swab, the side of a forcep or rod, or is gently held by a pair of forceps, the nerve is elevated slightly to allow a form to be placed underneath the nerve. In one embodiment, the nerve is then gently lowered into a channel or entry zone to align the nerve in the center of the form. See, e.g. FIGS. 1A and 1B. The form, once the desirable position is reached, is left in place.

While holding the nerve tip in one hand in the center of the form, the clinician then delivers the in situ forming hydrogel using the other hand to fill the form and retain the nerve in the center of the form. The top of the silicone form serves as a guide for when to stop filling the form. As the hydrogel fills past the top of the nerve, the swab/forcep is removed so that the nerve is retained within the hydrogel and not the tool. In this manner, there is no direct path for a nerve to regenerate through the surrounding tissue and the nerve is completely surrounded by the hydrogel.

Gel thickness. Preventing nerve regeneration requires providing a conformable barrier at the proximal end of a transected nerve. The hydrogel also preferably surrounds the nerve with a thickness of 100 μm to 5 mm radially. In one embodiment, the hydrogel precursor solution is dripped over the nerve to form a thin protective coating approximately 100 microns to 2 mm in thickness circumferentially around the proximal nerve stump and remain in the place to block neurite outgrowth. A thin coating is sufficient to provide a barrier to nerve regeneration and thus in some embodiments, the nerve is dip-coated in the flowable media and the hydrogel subsequently forms in a thin layer around the nerve. In this embodiment, the hydrogel gelation time is adjusted to 10 to 20 seconds to permit the removal of the coated nerve prior to the conversion to a nonflowable form with gel formation. Thin coatings providing adhesion to and coverage of the circumference and tip of the nerve stump on the order of 50 microns to 500 microns to cover the end of the nerve are desirable.

In yet another embodiment, it is desirable to form the hydrogel around the nerve in an implant or bolus, providing a robust adhesive layer of hydrogel around the nerve, approximately 0.5 to 5 mm, more preferably 1-2 mm in thickness around the circumference of the nerve and 1 to 5 mm beyond the tip of the nerve stump tip.

Pore size. In order to prevent nerve regeneration into the biomaterial, the pore size of the hydrogel needs to be sufficiently small to prevent nerves and other supporting cells from infiltrating the biomaterial. Nerve axon diameters are between approximately 0.5 and 30 µm. Preferably, the growth inhibitory hydrogel is microporous or mesoporous, with pores less than 1 µm, preferably less than 0.5 microns, more preferably less than 500 nm in diameter.

Charge Neutrally or negatively charged biomaterials are preferred as growth inhibitory gels as neurites prefer to grow into positively charged biomaterials. Similarly, hydrophilic materials or amphiphilic are preferable to hydrophobic materials.

Nondegradable hydrogels. If a nondegradable hydrogel system is used, the same equilibrium swelling characteristics apply but, since the hydrogel is nondegradable or biostable, degradation swelling is not relevant. For example, the non-degradable in situ forming thermoresponsive copolymer, Pluronic (PEO-PPO-PEO), polyvinyl alcohol, or PEO may be utilized to form hydrogels.

Clarity. In the preferred embodiment, the hydrogel is clear and transparent to confirm the location of the nerve after hydrogel formation. A visualization agent may be incorporated in the hydrogel to aid in contrast relative to the background tissues. The color additive or color additive blend may be included in a the polymer powder solution. In the case of the use of multiple hydrogels (described below), the use of one or more different visualization agents is desirable to provide visual confirmation, for example, that the growth permissive hydrogel was correctly delivered between the nerves and the growth inhibitory hydrogel was delivered around the growth permissive hydrogel. Elasticity. In some embodiments, the elasticity of hydrogel can be modulated by incorporating hydrophobic domain into the hydrogel. The hydrophobic domain can be incorporating by crosslinking or mixing of molecules, particles, fibers and micelles. The molecules incorporated can be amphiphilic molecules including pluronic, polysorbate and tocopherol polyethylene glycol succinate. The particles, fibers and micelles can be made from amphiphilic molecules described in the above section. In addition, many low molecular weight hydrophobic drugs that are incorporated into the hydrogel (described below) improve the elasticity of the hydrogel.

Kit. The in situ forming hydrogel is delivered through a dual applicator system comprising a dual channel applicator, a dual adapter, one or more mixers, and one or more blunt needles. Also included in the kit is a powder vial with associated vial adapter, diluent solution, and accelerator solution for use in the dual applicator system. The kit may include one or more forms into which the hydrogel is delivered. The kit may also include on or more mixer-blunt syringes. The Mixer syringes may be conventional single lumen mixers with a static mixing element or the mixers may be mixers in which there is recirculation and turbulent flow of the contents to improve the mixing of the precursor solution.

Chemical and physical. Preferably, the hydrogel networks are predominantly hydrophilic with high water content and are formed through the physical or chemical crosslinking or synthetic or natural polymers, copolymers, block copolymers or oligomers. Examples of synthetic hydrogels that are not growth permissive include agarose, PEG, or alginate, PVA hydrogels with 2% w/v solid content or higher, preferably 6% w/v solid content, more preferably 8% w/v solid content or higher. PEGs. Multi-arm PEGs are described above but may be selected according to the desired properties from PEG-amine, PEGarboxyl, PEG-SCM, PEG-SGA, PEG-Nitrophenyl carbonate (carbonate linker), PEG-Maleimide, PEG-Acrylate, PEG-Thiol, PEG-Vinysulfone, PEG-Succinimidyl Succinate (SS), PEG-Succinimidyl Glutarate (SG), PEG-Isocianate, PEG-Norbornene or PEG-Azide. Alginate. Viscous injectable alginate sol (1 to 5%) may be delivered around the nerve. Similarly, agarose gel at concentrations of 1% wt/vol or more prevent nerve extension.

Hypotonic solutions. In one embodiment, a hypotonic solution (Ca2+ free, slightly hypotonic, saline solution containing 1-2 mM EGTA) is delivered to the cut nerve to assist in the sealing of crushed or transected axonal ends prior to repair with the in situ forming biomaterial.

PEG Fusion Combined with an In Situ Nerve Cap or Wrap. As described in the many publications outlining methods for PEG fusion of nerves (3.35-5 kDa, 30-50% w/v solution), a PEG solution can be delivered to the nerves to first fuse the nerves, alone or in combination with methylene blue. After sealing the membranes, the growth permissive hydrogel is delivered in between and around the compressed or severed nerves.

Cross-linked Particles. In some embodiments, the hydrogel can be made with cross-linkable particles, fibers, or micelles. These particles, fibers or micelles are functionalized with reactive groups, including but not limited to active ester, amine, carboxyl, aldehyde, isocyanate, isothiocyanate, thiol, azide and alkyne, which can be cross-linked with small molecules, polymers, particles fibers or micelles with reactive groups to form bonds including amide, carbamate, carbonate, urea, thiourea, thioester, disulfide, hydrazone, oxime, imine, amidine and triazole. In some embodiments, the micelles, fibers and particles can be formed from amphiphilic macromolecules with hydrophilic and hydrophobic segments. The hydrophilic segments can be natural or synthetic polymers, including polyethylene glycol, polyacid, polyvinyl alcohol, polyamino acid, polyvinyl pyrrolidone, polyglycerol, polyoxazolines, and polysaccharides. Hydrophobic segments can be fatty acids, lipids, PLA, PGA, PLGA, PCL and the polymer ester copolymer at different ratio. In another embodiment, functionalized microparticles form physical crosslinks with one another after a pH change, and then, when placed in situ, the functionalized particles crosslink to form an interconnected network of microparticles.

Sealants. Some of the in situ forming gels developed for adhesion prevention and sealants may also be adapted for this application to preventing neuromas and aberrant nerve outgrowth into scar tissue, such as low molecular weight polyanhydrides of acids like sebacic acid, including poly (glycerol-co-sebacate) (PGSA) based sealants (U.S. Pat. No. 9,724,447, US20190071537, Pellenc et al (2019) Preclinical and clinical evaluation of a novel synthetic bioresorbable, on demand light activated sealant in vascular reconstruction, incorporated herein and adapted for use around nerves, for reference). Another sealant that may be adapted for delivery around peripheral nerves is the Adherus Dural Sealant, which comprises a PEG-polyethylenimine (PEI) copolymer that forms in situ, as it exhibits low swelling and degrades in about 90 days (U.S. Pat. No. 9,878,066, incorporated herein). Other sealants include BioGlue Surgical Adhesive (Cryolife), composed of bovine serum albumin and glutaraldehyde, Omnex (Ethicon), ArterX (Baxter), Coseal (Baxter) and TissuGlu, composed of lysine based urethane (Cohera Medical).

Photoresponsive. In some embodiments, photoresponsive, photopolymerizing or photocrosslinked biomaterials are envisioned that could be delivered in a liquid (low to medium viscosity) state into the form (cap or wrap form) around the nerve, and then, when the proper positioning of the nerve is obtained within the form, the photopolymerization is initiated with either ultraviolet or visible light. In one embodiment, the light source can be attached directly or via fiber optic cable that interfaces directly with an opening in the cap or wrap form. The cap form diffracts the light such that it ensures that the entire form is sufficiently illuminated to achieve consistent homogenous crosslinking across the gel. In the preferred embodiment, the light source housing is coupled directly with the form at the distal end of the cap facing the nerve stump face to ensure that the light directly penetrates. Alternatively, the form may be designed with embedded light-emmitting elements that permit the light to be delivered circumferentially around the nerve. Hydrogels include PNIPAAM hydrogels modified with a chromophore such as trisodium salt of chlorophyllin.

Other forms. In addition to a cross-linked network, hydrogels may be comprised of dendrimers, self-assembling hydrogels, or low molecular weight synthetic polymer liquids.

In one embodiment, lower molecular weight hydrogels (2 kDa, liquid) can be formed in situ without water as a solvent as described in Kelmansky et al (2017) In Situ Dual Cross-Linking of Neat Biogel with Controlled Mechanical and Delivery Properties), Molecular Pharmaceutics, 14(10) 3609-3616, incorporated herein. In yet other embodiments, hydrogels can be photocrosslined to form hydrogels, as extensively described in the literature. Crosslinking agents include eosin,) In yet other embodiments, electroconductive hydrogels are usied including poly(3,4-ethylenedioxythiophene) (PEDOT), poly(pyrrole), polyaniline, polyacetylene, polythiophene, ester derivative, 3,4-propylenedioxythiophene (ProDOT), natural or synthetic melanin, derivatives, and combinations thereof.

Addition of sulfated proteoglycans. In some embodiments, it may be desirable to deliver inhibitory environmental cues to the nerves in addition to the mechanical barrier provided by the hydrogel. This can be accomplished by the addition of inhibitory molecules and/or extracellular matrix to the hydrogel either through physical blending or chemical crosslinking. Sulfated proteoglycans, such as side chains with a negative charge such as glycosaminoglycans are of interest. Of particular interest is dermatan sulfate (DS).

Blends. In some embodiments, it may be desirable to create blends of two PEGs to improve the degradability of the system. In one embodiment, the PEG-SC is combined with PEG-SG prior to crosslinking with trilysine amine to create a hydrogel that has sufficient mechanical support to prevent nerve outgrowth but then degrades more rapidly than PEG-SC. The persistent time of gel in vivo is fine-tuned by the ratio of PEG-SG and PEG-SC. With the increase of PEG-SC content, the persistent time of gel in vivo increases. In another embodiment, the PEG-carbamates are blended with the PEG-carbonates. Other hydrogels include PEG hydrogels comprised of carbamate derivatives (U.S. Pat. No. 7,060,259).

Incorporation of agents. In some embodiments, agents can be dissolved or suspended in the diluent or accelerator solution and surfactants or ethanol can be added to stabilize the suspension. The drug can be also encapsulated in microparticles, nanoparticles or micelles and then suspended in diluent or accelerator. In some embodiments, the hydrogel can be made with cross-linkable particles and micelles. These particles or micelles have reactive groups such as the active ester, amine, carboxyl, thiol and those described in U.S. Pat. No. 7,347,850 B2 and can be crosslinked with small molecules, polymers, particles or micelles with reactive groups which reacts with the former particles or micelles and forming bonds including amide, carbamate, carbonate, urea, thiourea, thioester, disulfide, hydrazone, oxime, imine, amidine and triazole. In other embodiments, gel can be form by the swelling of particles. The large volume of swelling can increase the particle contact and lock them into their location to form gel.

Solid content. The solid content can be adjusted to fine tune the swelling and tensile properties of the hydrogel. For example, the solid content can be adjusted above the critical gelation concentration, such as between 6 to 15% loading, more preferably 7-9% loading, more preferably 8-8.5% solid content.

Crosslinking. Hydrogels may be formed in situ through electrophilic-nucleophilic, free radical, or photo-polymerization.

In vivo Persistence. In some embodiments a longer in vivo persistence may be preferred, in which the hydrogel remains in situ for between 3 months and 3 years, more preferably 6 months and 18 months, more preferably 6 months and 12 months.

Adhesion. Adhesive strength is an important criterion for maintaining the hydrogel in close apposition to the nerve. Adhesion may occur through crosslinking reactions between the hydrogel and the primary and secondary amines on the tissue surface e.g. the epineurium or the amine groups found on the surface of nerves, glia, and associated cells. The adhesion strength should be greater than 10 kPa, preferably greater than 50 kPa, more preferably greater than 100 kPa. Adhesive strength on nerves can be estimated by embedding the sciatic nerve in the hydrogels. The ends of the nerves are embedded in superglue between sandpaper and placed in titanium clamps in a Bose ElectroForce 3200-ES. Nerves are pulsed at a rate of 0.08 mm/s until failure. Care was taken to ensure that the nerves were used shortly after harvest and that the hydrogel and nerve were equilibrated in PBS at 37° C. prior to testing.

Other hydrogels. In situ forming polyanhydrides are also of interest for developing applications directed towards nerves. In one embodiment, polyanyhydride polymers can be acrylated so that they can form in situ through free radical polymerization. Alternatively, they can form through photocrosslinking. At lower concentrations, the polymers are water soluble e.g. 10%. The prevention of nerve regeneration is conferred in part through their hydrophobicity. Incorporated for reference are US20180177913A1, U.S. 62/181, 270, and US201562181270P.

Applicator. Dual channel applicators used to deliver the in situ forming hydrogels are commercially available (Nordson Medical Fibrijet Biomaterial Applicators, Medmix Double Syringe Biomaterial Delivery System, K-System). However, these mixers, delivering between 2.75 and up to 10 ml of hydrogel, include a single lumen with a static mixing element and are designed for the adequate mixing and delivery of large volumes of hydrogel solution and are not ideal for delivering small volumes (<1 ml) of hydrogel solution to a site. As a result, there is a need for a mixer that provides mixing of small volumes of two component systems as inevitably, one of the two solutions is typically advanced slightly ahead of the other solution, leading to a small volume of partially or inadequately mixed gel existing the needle first. In one embodiment, a custom mixer is designed to fit onto the Nordson Medical or K-System applicator, through either a luer or a snap fit, as the dual chamber applicator system necessitates, to recirculate some of the initial solutions that enter the mixer in order to ensure better mixing of the hydrogel, including the initial components. FIG. 18 illustrates the design (transparent) of the center portion of the mixer containing an entrance port with at least one static mixer, a larger container through which the contents are delivered and recirculated and a second port which captures the mixed recirculated fluid and delivers it to the exit port of the mixer. The second port may or may not contain additional static mixers.

Example 1

In some embodiments the 4-arm-PEG 10K-SC is crosslinked with an 8-arm PEG 20K amine. The PEG-SC and PEG-amine were dissolved in an acidic diluent at a ratio of 1:1. The suspension was mixed with accelerator buffer and delivered through a static mixer to form a hydrogel. This formulation gelled in 4 seconds.

Example 2

In other example, 8-arm 15K PEG-SC is crosslinked with trilysine. The PEG-SC was suspended in buffered trilysine solution and then mixed with accelerator buffer through a static mixer. This formulation gelled in 2 seconds and the gel provided compression strength up to 200 kPa.

Example 3

In other example, 8-arm 20 K PEG-thioisocyanate is crosslinked with trilysine at a ratio of 1:1. The formulation gelled in 3 seconds and has a compression strength of 120 kPa and 5% swelling.

Cap Form. The method may comprise the step of positioning a form at a treatment site before the positioning the severed end step. The form is provided as part of the kit containing the delivery system and is composed of an inert, biocompatible, flexible and nonadhesive material to provide the desired shape to the in situ formed material. The form is designed to be filled with the flowable media such that it flows around the proximal nerve stump end where it transforms to a non flowable composition, conforming to the nerve stump and preventing neuroma formation. In the preferred embodiment, the form creates a low profile nerve cap with a smooth transition between the nerve and the cap and approximately cylindrical shape around the nerve.

Shape. A form is desirable, not only because it reduces off target spread of the in situ forming material but because it provides a low-profile circumferential lubricious shape that cannot be achieved with the application of the hydrogel alone. The profile and transitions of the form design reduce the friction and interference with the surrounding tissue, allowing the hydrogel to glide and rotate relative to the surrounding tissue. The cap is designed to be able to cover at least 5 mm, preferably a 10 mm length or more of nerve.

In accordance with another aspect of the present invention, there is provided a form for creating a formed in situ nerve cap to inhibit neuroma formation. The form comprises a concave wall defining a cavity, the wall having a top opening for accessing the cavity. The top opening lies on a first plane and has an area that is less than the area of a second plane conforming to inside dimensions of the cavity and spaced apart into the cavity and parallel to the first plane. A concave nerve guide is carried by the wall and provides a side access to the cavity for receiving a nerve end. The wall is flexible so that it can be removed from a crosslinked nerve cap formed within the cavity, and may comprise silicone, preferably with a durometer of 30-50, most preferably a durometer of 40. The wall design of the form has a slight undercut such that the material, when filling the form to the top edge of the form, forms a convex surface due, in part, to surface tension of the media, that completes the cylindrical shape of the hydrogel.

Silicone. In one embodiment, the form is comprised of a nonadherent nondegradable material. In the preferred embodiment, the material is medical-grade silicone, sufficiently flexible to be peeled or popped off of the in situ formed material (e.g. durometer 40). After the transition of the media to a substantially non-flowable state, the silicone form is removed and discarded. In one embodiment, the silicone form is colored to provide contrast against the surrounding tissue so that the nondegradable polymer is not accidentally left in situ. Darker colors are preferable to enhance the light that enters the cap and illuminate the nerve, such as dark blue, dark purple or dark green.

Biodegradable. The method may alternatively comprise the step of placing a biodegradable form before the positioning the severed end step. The biodegradable form may be comprised of a non-crosslinked lyophilized (or dried) synthetic biomaterial that remains in place for approximately 5 to 10 minutes during the time that the in situ forming hydrogel is delivered, and then is rapidly dissolved and cleared from the site in less than, for example, one or two days. In one embodiment, the bioerodible form is comprised of lyophilized multi-arm end-capped or non crosslinked PEG, lyophilized linear PEG (3.35 kDa) or crosslinked multi-arm PEG (e.g. 8-arm 15 kDa). The method may alternatively comprise the step of forming a biodegradable form in situ before the positioning the severed end step. In alternate embodiments, the form is composed of materials typically used for nerve conduits and wraps, such as polyvinyl alcohol, chitosan, polylactic acid, polyglycolic acid, polycaprolactone.

In yet another embodiment, the ex vivo implantable form is comprised of the same material as the in situ formed material that is delivered into the form. In this manner, the properties of the equilibrated form are comparable and match well with the equilibrated in situ formed hydrogel. In these embodiments, the biodegradable form for remains in place after delivery of the hydrogel and is not removed but is cleared from the implant site at approximately the same rate as the in situ formed material. In yet another embodiment, the form is comprised of lyophilized non-crosslinked PEG into which the in situ formed hydrogel media is delivered. The non-crosslinked PEG is readily solubilized and cleared from the site, making the form a rapidly bioerodible form. In yet another embodiment, the form is comprised of a crosslinked PEG matrix that will be cleared rapidly from the site as a result of a rapidly cleaved hydrolytic bond, such as can be obtained with the ester linkage in a PEG succinimidyl succinate (PEG-SS).

Forms can be synthesized by injection molding, crosslinking or polymerizing in a cavity, solvent casting, or 3D printing. A range of synthetic and natural materials can be selected for the implantable form, including collagen, PEG-PEI, alginate, chitosan, or agarose.

Forms may be rapidly dissolving forms, that, upon wetting, dissolve and are cleared within an hour so after the procedure, leaving the in situ formed biomaterial in place. Alternatively, forms may be more slowly degrading forms that swell to a similar or greater extent that the in situ formed material that is delivered inside them. The swelling prevents scenarios in which the hydrogel swells during equilibrium swelling and compresses the nerve if the form into which it is delivered is shrinking or has minimal compliance.

In some embodiments, the nerve positioned is held in the desired location or orientation with forceps in one hand and the media is delivered with the other hand into the form. As the media fills the form, the nerve is released and subsequently the media changes to a non-flowable state. Alternatively, a supporting physician or nurse may assist with the procedure. In another embodiment, the growth inhibitory hydrogel is formed around the nerve in a two-step process. In the first step, the hydrogel is delivered to the nerve tip to encapsulate the nerve end. In the second step, the hydrogel is applied to fill the entire form, including the nerve tip. In another embodiment, the growth inhibitory hydrogel is formed around the nerve in a first layer and then a second layer of hydrogel is subsequently applied, in a two-step process.

Conformability. Unlike wraps, which still have a gap between the wrap and the nerve, the hydrogel conforms directly to the nerve itself providing a barrier to inflammatory and pro-scar forming cells to the site while allowing nutrients through. Because the hydrogel adheres to the nerve, there is no need to suture the nerve to the hydrogel. The proximity of the hydrogel to the nerve also helps to prevent scar and adhesion formation around the nerve in the initial healing phase.

Centering. Nerves, by virtue of their low density and high fat content and flexibility, particularly smaller nerves, have a tendency may flow upwards in a low viscosity solution. The following embodiments are designed to assure that the nerve does not float up after delivery of the media to the top of that surface.

Viscosity. As described above, the viscosity of the flowable solution can be increased to minimize the nerve floating up within the solution.

Flow. In another approach, the needle that delivers the flowable media is directed in such a way that the flow of the media permits the circumferential spread of the solution around the nerve prior to the gel forming. The cap form can also be designed to improve the flow dynamics of the media and improve nerve alignment. In one implementation of the invention the severing a target nerve step and the positioning a form at a treatment site step are accomplished by a single instrument. In another implementation of the invention, the nerve cap form is designed such that the delivery system and the form are integrated. In the preferred embodiment, the delivery system is connected to the form via a catheter. The catheter entrance in the cap resides at the same entrance where the nerve is entering the form. The catheter permits the flow of material down the shaft and circumferentially around the nerve such that the media acts to self-center the nerve within the form.

Stabilizer. In another embodiment, a stabilization rod or piece is aligned directly under the nerve or against the nerve such that it provides sufficient adhesive forces that the hydrogel can be delivered around the centered nerve into the form.

Peelable conduits In yet another embodiment, the nerve is positioned in the center of the in situ biomaterial through the consecutive placement within two peelable conduits. In brief, the nerve is placed inside the first peelable conduit and the in situ forming material is delivered to surround the top and distal end of the nerve. The peelable conduit may be an open ended or close ended conduit. After the hydrogel forms, the sheath is pulled apart along weaker peel lines in the material an discarded. The resultant nerve-hydrogel is then placed in a second larger peelable conduit. By rotating the nerve slightly, the hydrogel surface can be placed on the bottom of the second sheath so that the nerve is centered in approximately the middle of the second sheath. A second application of the in situ forming hydrogel results in the cumulative formation of a circumferential hydrogel around the nerve which protects and centers the nerve within the nerve cap. In one embodiment, the sheath is composed of an extruded splittable PTFE tube with a vertical tab to assist in tearing the piece apart in the surgical setting, similar to vascular introducers.

In another embodiment, the nerve is placed so that the proximal stump rests at a ninety degree angle downward in a cup-shaped form and the hydrogel delivered into the cup-shape to form around the nerve. The cup-shaped form is subsequently removed and discarded and the proximal stump is adjusted back to its resting position in the tissue.

In yet another embodiment, the nerve can be delivered in an amphiphilic or hydrophobic solution to prevent the nerve from floating to the surface of the medial. In yet another embodiment, the in situ forming material may be more viscous, to prevent the nerve from migrating within the form.

Tilted. Alternatively, the form may have a tilt in the form, to bias the nerve filling from the distal to the proximal end. In this manner, the nerve can be positioned in such a way that the hydrogel forms circumferentially around the proximal nerve tip first and then, either through a second application or a continuation of the first application, fills the rest of the form.

Entrance centering. In one embodiment, the forms are designed in such a way that the nerve enters at a lower level relative to the top of the form to permit the material to be delivered circumferentially around the nerve. In another embodiment, the entrance region of the form is sloped so that the nerve enters the form at a downward angle, biasing the proximal nerve tip location downward.

Ribs. Tabs or ribs are provided on the external face of nondegradable temporary forms, such as silicone forms, to assist with the removal of the form after formation of the gel. These tabs are placed in such a place to provide additional stability for the cap form on irregular surfaces or to provide a surface to grip with forceps or other surgical instruments. In yet another embodiment, the form is designed to be self centering. In other words, the form may naturally seat itself so that the top surface of the form is level in preparation for delivery of the in situ forming hydrogel.

Holes. In some embodiments, a hole or guidance sheath is provided to direct the needle to deliver the media into the form in a particular direction. The direction of the media flow can be designed to better position the nerve in the channel. In one embodiment, the hole is provided adjacent to or on top of where the nerve enters the form to guide the solution from proximal to distal in the conduit and encourage laminar flow within the form.

Lids. In some embodiments, the form contains a partial or complete hinged lid to permit the centering of the nerve according to the direction of flow within the form.

Volumes delivered. As with the cap form, the volume of media delivered may range from 0.1 cc to 10 cc, typically 0.2 to 5 cc, more typically 0.3 to 1 cc.

Needle size. The kits contain a 21 gauge or 23 gauge needle for delivering smaller volumes into smaller size wrap (or cap) forms and 18 gauge needles for filling larger forms. These needles provide additional control to the speed of delivery of the in situ forming material, permitting, the deposition of a bead of the hydrogel to the rapid filling of a larger conduit.

Gelation time. Similarly, the gelation time can be adjusted depending on the fill volume of the wrap or cap forms, providing longer gelation times of 10 to 20 seconds for larger wraps and a shorter gelation time of around 5 seconds for smaller wraps or caps.

Form sizes and hydrogel thickness. The range of form sizes are designed with an entrance region to accommodate a nerve diameter ±1 to 3 mm, or more preferably ±1 mm. The diameter of the form determines the thickness of the gel that forms around the nerve. The thickness of the hydrogel that forms around the nerves may be 0.05 mm to 10 mm, more preferably 1 mm to 5 mm, more preferably 1 to 3 mm depending on the size of the nerve.

Kit design. Instead of each kit containing one form for only one size of nerve, as is the case with implantable nerve conduits and wraps, kits will contain one to ten, more typically one to cap forms (or wrap forms, or combinations thereof), allowing the physician to select the appropriate size for the procedure as well as the ability to switch the form out without having to request an additional kit. Kits may be labelled according to forms selected—for example forms for a ranges of nerve sizes, forms for a type of surgical procedure (nerve protector for inguinal repair), or forms appropriate for a specific location of the procedures (nerve cap for hand surgery, nerve protector for upper limb, nerve form for brachial plexus).

Sheets. In some embodiments, the in situ forming material may be delivered to a nerve that is placed on a temporary nonadherent biocompatible sheet such as an Esmarch bandage or other biocompatible sheet or background (Mercian Surgical Visibility Background Material) routinely used to isolate the nerve from the surrounding tissue. The gelation time can be shortened to limit the spread of the hydrogel around the nerve, for example to 10 seconds or less, preferably 5 seconds or less. Any excess hydrogel can then be removed from the surgical site and discarded.

Liquid Cap Form. In another embodiment, the form is not a physical form but created by the injection of a soluble hydrophobic solution, preferably a viscous solution, such as glycerol. For example, while securing the nerve out of the way, a viscous oil can be delivered to the surrounding tissue to coat it and prevent the hydrogel from adhering the surrounding tissue. The solution, if viscous enough, can create a rapidly bioerodible form for delivering the in situ forming hydrogel. In the preferred embodiment, Solution A is delivered first to block the amine and tissue binding sites and to create a space or region into which Solution B can be delivered. In the next step, Solution B is delivered in the space created by Solution A, or it is delivered in the center of Solution B, displacing Solution B away from the site.

No Form. In some embodiments, the space or access does not permit the use of a form. In some cases, such as in brachial plexus injuries, the surgical window is so small or the concern of damaging adjacent tissues is so small that placing a form in the site into which to deliver the hydrogel is not possible. In these instances, the hydrogel may be delivered directly into a surgical pocket or region in or around the nerve. If the region around the nerve is utilized as a natural form, the cap has an irregular shape that is defined by the boundaries of the tissue on the bottom and sides of the nerve. In one embodiment, since the hydrogel is adherent to both the nerve and the tissue, the in situ formed material should be carefully peeled off of the muscle and fascia so that it forms a free-floating bolus in contact with the nerve. This will permit the nerve to continue to move within the region without being tethered to the surrounding tissue.

In still further embodiments, it is desirable for the hydrogel to take the shape of the surrounding tissue around the nerve. For example, in embodiments where the nerve is to be ablated and the hydrogel needs to fill the potential space where the nerve is/was and the surrounding area to prevent regeneration. Alternatively, when the hydrogel is delivered around visceral nerves where there is frequently a loose and fine network of tiny nerve fibers and the space around these nerve fibers needs to be filled. In another embodiment, the hydrogel fills around irregularly shaped nerves or bundles/clusters of nerve fibers and/or cell bodies. In this way, the hydrogel can most effectively deliver therapeutic agents to the region.

Hydrogel placed in a controlled manner in situ around a nerve. In another embodiment, however, particularly in dynamic environments in which nerves are sliding during motion between muscles, joints, bones, or tendons, such as between muscles in the periphery, it is not desirable for the nerve to be tethered via the hydrogel to the surrounding tissue. Instead, it is desirable to develop solutions in which the nerve can glide freely within the channel. In these embodiments, the hydrogel can be physically separated from the surrounding tissue during in situ crosslinking or in situ polymerization. This can be achieved with something as simple as a nonadhesive sterile sheet which can be placed at the site and then removed after gel formation. This can also be achieved through the placement of a form in/around the nerve. The form may take several forms depending on the size and location of the nerve, the presence or absence of a sheath, the goal of the therapy that is delivered to the site (nerve stimulation, nerve blocking, nerve ablation, or a barrier to nerve regeneration). In one embodiment, the form is a cap that can be gently placed around the end of a nerve and the in situ forming gel injected into this form in order that it assume the shape of the form. The material in the cap can then be pushed out and the cap form removed and discarded. In yet other embodiments, the cap is biocompatible and thus is not removed. In another embodiment, a half-cylinder (halved longitudinally) can be placed underneath the nerve and the in situ forming material delivered into the half cylinder. In this same manner, it is possible to deliver a gel circumferentially around the nerve without the gel developing attachments to the surrounding tissue.

Alternate cap forms. In order to reduce the chances of adhesions forming, the 3 to 10 mm sections of nerve can be placed inside a syringe barrel (with the luer lock end portion removed) and the plunger pulled back to the appropriate gel distance that is desired on the end of the nerve. The hydrogel is delivered into and around the nerve inside the plunger where the gel sets. After the gel forms, the plunger is gently depressed to extrude the nerve encased in the hydrogel. Using this approach again, minimal or no sutures are required to avoid additional damage or over handling of the nerve. Preferably the syringe barrel has a lubricious coating.

Laprascopic or endoscopic surgery. The forms may be advanced down a channel during laprascopic or endoscopic surgery and placed under a nerve, similar to the approach in open surgery. The form may be folded to permit transit through smaller conduits and then released at the site of the procedure. Alternatively, instruments can be designed with the nerve form (cap or wrap) build into the tip of one instrument with the in situ forming biomaterial delivered through the lumen of another instrument. Gelation time of the in situ forming biomaterial needs to be adjusted to 20 to 30 seconds or more to allow for travel time of the hydrogel down the instrument lumen.

In a needleoscopic approach to the procedure, a first material can be injected that coats the outside tissues to prevent direct adhesion between the gel and the surrounding tissue. After this, the hydrogel can be delivered into the same site, forming a depot around the nerves and displacing the first material to the periphery of the injection site. This can be achieved with a hydrophobic substance, such as an oil or a viscous substance such as glycerol. This may also be achieved with a low molecular weight PEG solution which has the added benefit of helping seal the membranes of the nerve prior to the hydrogel forming the nerve block/cap around the nerve.

In another embodiment, the nerve is dipped in the flowable material solution prior to it crosslinking to form a thin protective surface on the hydrogel. In some embodiments, only a thin coating of the biodegradable polymer is necessary around the nerve. The coating may be only 100 microns to 500 microns thick. In other embodiments, a coating is not sufficient to prevent the inflammatory infiltration and or prevent early degradation—in these cases it is desirable to use a coating of between 0.5 mm to 10 mm thick.

Attempts at developing nerve caps to date have been focused on solid physical caps that are sutured in place around the end of a transected nerve. These caps have, by necessity, had a gap around the end of the nerve at the end of the proximal stump as well as circumferentially. As a result, neuroma formation occurs into the end of the cap. Examples include resorbable poly(D,L lactide-co-caprolactone) implant, aligned silk fibroin (SF) blended with poly (L-lactic acid-co-e-caprolactone) (SF/P(LLA-CL)) nanofiber scaffolds, poly(lactic acid)-co-(glycolic acid)/ arginylglyclaspartic acid) modified poly(lactic acid-co-glycolic acid-alt-L-lysine) (PRGD-PDLLA) implant with pores on the order of 10 microns in diameter [), Yi et al 2018, Adv Sci]. The PRGD/PDLLA conduit was 10 mm long with an inner diameter of 2 mm and a tube wall thickness of 200 microns, the SF/P(LLA-CL) conduit is 1.5 cm long with an internal diameter of 1.5 mm. These caps require suture placement. Another approach, called Neurocap®, is a synthetic nerve capping device including of a solid tube with a closed end that is placed over the nerve bundle and then has to be both sutured to the nerve to keep the nerve within the cap and sutured to the surrounding tissue to hold the cap in position, published as WO2016144166A1. Another approach also utilizes a solid implant, published as US20140094932A1. In contrast, the injectable gel approach can flow around nerves of any size from tiny fibers to large nerve bundles, does not require cutting or suturing, and provide a reduction in pain and neuralgia. In short, an injectable flowable system is not limited to nerve stumps but also can prevent aberrant nerve outgrowth in fibers too small to be picked up.

NERVE PROTECTOR/WRAP. In accordance with a further aspect of the invention, there are provided methods and devices to protect intact or compressed nerves. In some instances, it may be desirable to protect nerves that are surgically exposed as a result of a procedure or adjacent nerves or tissues, such as in the instance where these nerve would otherwise dry out. In some instances, it may be desirable to protect and mark the nerves that are exposed as part of another surgery so that additional handling, stretching, contusion and/or compression can be reduced or avoided. In one embodiment, an in situ forming material is delivered around the nerve to provide a protective layer and prevent the nerve from damage from forceps and other surgical equipment in the region. Additionally, a dye in the hydrogel can provide sufficient contrast from the surrounding tissue that the physician can also visually stay away from the nerve during the procedure. This may dramatically reduce the incidence of iatrogenic nerve injury during surgical procedures.

In accordance with a further aspect of the invention, there is provided a form for creating a formed in situ capsule around a nerve to nerve junction. The form comprises a concave wall defining a cavity, the wall having a top opening for accessing the cavity. The top opening lies on a first plane and has an area that is less than the area of a second plane conforming to inside dimensions of the cavity and spaced apart into the cavity and parallel to the first plane. A first concave nerve guide is carried by the wall and provides a first side access for positioning a first nerve end in the cavity; and a second concave nerve guide is carried by the wall and provides a second side access for positioning a second nerve end in the cavity.

One example of this is the prophylactic treatment of the ilioinguial and iliohypogastric nerves during procedures to repair hernias, particularly inguinal hernia repair. These nerves may be partially or completely exposed during the repair of the hernia, resulting in compression, contusion, and partial or complete transection. Post-surgically, the damaged nerve may send aberrant nerve sprouts out into the post-surgical scar tissue which may result in neuroma formation and nerve entrapment resulting in a high rate of post-operative and chronic pain. In addition, these nerves may be incidentally or purposefully transected surgically in an attempt to prevent the nerves from being entrapped surgically or tangled in the mesh used to repair the hernia. In one embodiment, a kit containing the in situ forming growth inhibitory hydrogel and appropriate forms permit the surgeon to select a form to provide either a 'cap' or 'wrap' shaped form cavity. Depending on the surgery, the physician may then select a wrap if the nerve is not transected and the physician wishes to protect the nerve from further damage or a cap if the nerve is transected and the physician wishes to prevent the formation of distal neuroma at the end of the transected nerve.

Another example of this is the exposure of the sciatic nerve during hip procedures. Although the nerve is not the target of these procedures, the nerve is often exposed and placed in traction such that it runs a risk that it be damaged and/or dry out during the procedure. In one embodiment, a wrap-shaped form is provided to deliver hydrogel around the region of sciatic nerve at risk. For larger nerves, these region may be 5 to 50 cm or more. Wrap-shaped forms may be provided to span this entire length or alternately multiple cap forms can be placed in series along the nerve to provide protection. In another embodiment, an anti-inflammatory agent is delivered in the hydrogel in order to reduce the inflammation around the nerve that may result as a result of positioning or moving the nerve during the surgery. In another embodiment, a local anesthetic is delivered into the hydrogel that is placed around the nerve.

In another embodiment, the hydrogel is delivered around the nerve to reduce inflammatory neuropathies that may result after surgery, particularly peripheral neuropathy that may result in slowly developing severe pain and/or weakness in the affected limb. The in situ forming hydrogel may be delivered after open surgery or through a percutaneous image-guided procedure. For percutaneous ultrasound guided or fluoroscopic delivery, echogenic needles are desirable to confirm not only depth but location of the needle relative to relevant structures.

In another embodiment, an in situ forming hydrogel is delivered around the nerve in a 'wrap' form cavity to form a protective compliant wrap around the nerve. The wrap form cavity is left place, providing additional support and protection during the surgery, and then the wrap form is removed and discarded after completion of the procedure prior to closing the site. The hydrogel remains in place is to protect the nerve, prevent aberrant nerve outgrowth, and any scar tissue from infiltrating the nerve.

Coaptation aid. In some embodiments, a nerve that has undergone direct coaptation with sutures can be placed into a wrap form cavity. The direct coaptation site may be filled with an injected growth permissive hydrogel or temporary spacer material (e.g. fibrin glue) that can spread into the interstices of the site and the growth inhibitory hydrogel delivered directly around the anastomoses site using a wrap form cavity.

Wrap or protector form. The wrap form cavity comprises a form with two entrance zones for the nerve with a variable cavity length around the region of the nerve that needs protection. In shorter wrap forms, the cavity is designed such that the nerve rests on the entrance zones and the nerve is 'floating' between this region and does not make contact with the walls of the form. The needle that delivers the in situ forming hydrogel delivers the flowable hydrogel solution into the form, surrounding the nerve, where it forms a protective hydrogel around the nerve. The form prevents the off target spread of the hydrogel to adjacent tissues and maintains a consistent thickness of hydrogel around the nerve.

Longer lengths. In situations where there is a long length of nerve to protect, a longer wrap form cavity may be utilized with small posts designed in the bottom of the form to prop and provide stability to the nerve over longer distances. These posts are then removed when the form is removed, leaving only a small exposure between the nerve and the surrounding environment at a non-critical location away from the proximal nerve stump tip (if one exists). In yet another embodiment, in which it is desirable to protect longer lengths of nerve, the in situ forming hydrogel solution may be delivered in multiple layers or regions. In one embodiment, the form is filled in multiple sections in order to maintain the nerve within the center of the form. In another embodiment, a first layer of in situ forming hydrogel is delivered to the bottom of the form, either with the nerve or without the nerve completely or partially embedded, and then a second layer of hydrogel is delivered on top of the first layer in order to completely cover and protect the nerve.

In one embodiment, kits are provided which contain the appropriate volume of in situ forming hydrogel to fill the wrap form as well as multiple mixers and needle components to allow the physician to switch the mixer-needle tip and continue to deliver more of the media in second or third applications, as needed.

Protecting anastomoses sites. With the increased use of allograft in addition to autograft in larger nerve gap repairs, there is an increased recognition that aberrant nerve outgrowth from the peripheral nerve stump into the surrounding tissue at the nerve-allograft, nerve-autograft, or nerve-conduit junction can result in local pain and reduce the effectiveness of the nerve repair. In addition, the compliance mismatch between a solid implantable conduit used to secure two nerve stumps and the nerves themselves may cause friction at the interface between the nerve and the conduit resulting in additional aberrant nerve tethering into surrounding tissue. In one embodiment, the delivery of an in situ forming hydrogel at the interface between the proximal nerve and the allograft or autograft anastomoses, or the delivery of the hydrogel between the allograft or autograft and distal nerve stump, or similarly at the junction between where the nerve stump enters and exists the conduit, is anticipated. A smaller volume of hydrogel delivered either directly or in a shorter wrap form segment provides protection of neurite outgrowth and reduction in scar formation and immune cell infiltration into the graft and conduit. Alternatively, a wrap form may span the entire length of the anastomoses to cover the allograft/autograft/conduit in addition to the nerve.

Nerve gliding. Some peripheral nerves undergo a considerable amount of motion in the fascial plane in which they reside and thus scarring and tethering of these nerves is particularly painful. For example, the median nerve in the carpal tunnel or the ulnar nerve location relative to the elbow, are locations where a provision for gliding is important. With implantable conduits, wraps and protectors, the form of the implant is such that the gliding of the nerves is not enhanced with the biomaterial and may be further inhibited. In one embodiment, the in situ forming hydrogel is delivered as a protector around these nerves to permit the nerves to continue to glide within their fascial plane. One way this can be accomplished is by delivering a higher swelling in situ forming material that swells significantly, e.g. greater than 30%, preferably greater than 60% outward radially after delivery around a nerve such that the nerve can glide within the channel created after the hydrogel reaches equilibrium. In this manner, even though the hydrogel eventually becomes enchased in a thin capsular layer, the nerve itself, within the hydrogel, is free to glide within the channel and is free from significant scar tissue, nerve outgrowth into surrounding tissue and also is not compressed in these critical locations.

Indications. The in situ forming hydrogels can also be introduced intraoperatively to aid in the maintenance of a successful microsurgical anastomosis of donor and recipient nerves using a wrap form. They hydrogels can be injected in a wrarp form at the junction of the anastomoses to protect the aberrant inflammatory response, the formation of scar tissue, and aid in the coaption of the donor and recipient nerves. The transfer of a noncritical nerve to reinnervate a more important sensory or motor nerve is known as neurotization. In one example, a patient undergoing breast reconstruction after mastectomy can select autologous flap reconstruction to connect the nerves with the chest wall. Wrap forms can be placed at the junction between the proximal nerve stump and distal nerve tissue to which it is sutured and the hydrogel delivered to protect the anastomoses sites. This repair may lead to restoration of sensory function and an improvement in physical and quality of life advancement for women.

Compression repair. In another embodiment, the in situ forming hydrogels can be delivered in a wrap form around the nerve as a barrier to the attachment of surrounding tissue while the nerve repairs. This approach allows the hydrogel to infiltrate and conform to the nerve and act as a replacement for vein wrapping, in which autologous vein in wrapped around the nerve in a spiral wrapping technique, providing a barrier to attachment of surround tissue. This also provides an alternative to the AxoGuard Nerve Protector which has to be wrapped around the nerve potentially stretching and damaging it further. The solid nerve protector requires extensive handling of the nerve with forceps, stretching open the solid wrap to hold it open, and then suturing the nerve to the wrap. Using a soft, conformal, hydrogel based approach, a liquid or viscous liquid may be delivered directly around the nerve in a form with minimal nerve handling. Soft tissue attachments are minimized, swelling is minimized and mechanical support provided by the gel reduces the tension and stress on the coaption site. Nutrients can diffuse through the hydrogel network. Also, the hydrogel may reduce the physician's procedure time.

In one embodiment, the solution in based on hyaluronic acid. In another embodiment, the solution is based on a hydrogel slurry (TraceIT, Boston Scientific).

Distance applied. The hydrogel can be delivered circumferentially around the nerve using a syringe or applicator tip, in this manner, the nerve has protection over the length of the damage. Ideally, the hydrogel would be applied between e.g. 5 and 15 mm on each site of the damaged or transected nerve. Volumes administered may be between 100 microliters and 10 ml, more preferably 0.2 to 3 ml. The syringe contains the hydrogel (or the two precursor components to the hydrogel) can be designed with the exact volume to be delivered to allow for controlled automated delivery of the in situ forming hydrogel. Alternatively, an excess volume can be provided to allow the individual to use his/her judgment on how much to deliver around the site. At minimum, the hydrogel should form a cellular barrier approximately 200 microns thick around the outside of the nerve, although the hydrogel may also be delivered to fill a site and thus form a circumferential bolus with a 2 cm radius around the hydrogel site.

End-to-side Repair. A window in the outer nerve sheath is made and a nerve transfer is attached to the side of the nerve. After the suturing, the in situ forming hydrogel is delivered around this to keep these in close apposition with one another.

Internal neurolysis. After a nerve is stretched or chronically compressed, internal scarring and swelling my occur. The outer sheath of these nerves may be opened to relieve pressure and assist with blood flow.

External neurolysis. If nerves have become scarred or develop neuromas, stretching or moving may result in additional nerve damage, pain, and additional nerve scarring. Neurolysis can be used to remove the scar tissue around the nerve without entering into the nerve itself. The in situ forming hydrogel can be delivered around the nerve after the external neurolysis to prevent additional nerve scarring and reduce pain.

Neurotization. In one embodiment a percutaneous nerve protector is delivered around the damaged or crushed nerve. In this embodiment, if applied within a day to several days after injury, the local inflammatory response can be reduced. In situ forming hydrogels that are 1) biocompatible, 2) biodegradable or bioerodible, 3) permit diffusion of nutrients and oxygen into and out of the tissue while preventing inflammation, 4) flexible and compliant so that the axons are protected without being compressed, 5) non or minimally swelling, and 6) prevent fibrous ingrowth to the injury site.

Location. An injectable conformable hydrogel also permits the same product to be delivered to multiple nerve diameters and multiple locations (between bones, fascia, ligaments, muscle) as the material will flow in the region around the nerve.

Delivery location. In some embodiments, the needle location impacts the delivery of the hydrogel. In some embodiments, the needle delivers the hydrogel directly on top of the target nerve or region. In another embodiment, the needle is run distally to proximally to first fill the end of the form and the distal nerve stump and later to fill the rest of the conduit.

TMR. In another embodiment, the hydrogels can be delivered around nerve that are reconnected as part of targeted muscle reinnervation (TMR) procedures. Due to frequent the size mismatch between the transected donor nerve and the typically smaller denervated recipient nerve, it may be desirable to apply a hydrogel at the junction to help direct the regenerating fibers into the target receipient motor nerve. For these indications the hydrogel may be applied directly or within a form. Typically this is performed between a mixed motor and sensory nerve.

Inhibitory drugs to caps and wraps. Depending upon the desired clinical performance, the mechanical barrier may be assisted or enhanced by any of a variety of chemical agents that inhibit or prevent nerve regrowth (sometimes referred to as "anti-regeneration agents"). These agents include inorganic and organic chemical agents, including small molecule organic chemical agents, biochemical agents, which may be derived from the patient and/or from an external source such as an animal source and/or a synthetic biochemical source, and cell-based therapies. Anti-regeneration agents may be applied directly to target tissue prior to or following forming the nerve end. Alternatively, the anti-regeneration agents may be carried within the media where they become trapped in the media and are then released over time in the vicinity of the nerve end.

Some specific examples of anti-regeneration agents that may be used in conjunction with some embodiments of the present invention include, among others: (a) capsaicin, resiniferatoxin and other capsaicinoids (see, e.g., J. Szolcsanyi et al., "Resiniferatoxin: an ultrapotent selective modulator of capsaicin-sensitive primary afferent neurons", J Pharmacol Exp Ther. 1990 November; 255(2):923-8); (b) taxols including paclitaxel and docetaxel (i.e., at concentrations are sufficiently elevated to slow or cease nerve regeneration, as lower concentrations of paclitaxel may facilitate nerve regeneration; see, e.g., W. B. Derry, et al., "Substoichiometric binding of taxol suppresses microtubule dynamics," Biochemistry 1995 Feb. 21; 34(7):2203-11), botox, purine analogs (see, e.g., L A Greene et al., "Purine analogs inhibit nerve growth factor-promoted neurite outgrowth by sympathetic and sensory neurons," The Journal of Neuroscience, 1 May 1990, 10(5): 1479-1485); (c) organic solvents (e.g., acetone, aniline, cyclohexane, ethylene glycol, ethanol, etc.); (d) *vinca* alkaloids including vincristine, vindesine and vinorelbine, and other anti-microtubule agents such as nocodazole and colchicine; (e) platinum-based antineoplastic drugs (platins) such as cisplatin, carboplatin, oxaliplatin, satraplatin, picoplatin, nedaplatin and triplatin; (f) ZnSO.sub.4 (i.e., neurodegenerative factor); (g) latarcins (short linear antimicrobial and cytolytic peptides, which may be derived from the venom of the spider Lachesana tarabaevi); (h) chondroitin sulfate proteoglycans (CSPGs) such as aggrecan (CSPG1), versican (CSPG2), neurocan (CSPG3), melanoma-associated chondroitin sulfate proteoglycan or NG2 (CSPG4), CSPG5, SMC3 (CSPG6), brevican (CSPG7), CD44 (CSPG8) and phosphacan (see, e.g., Shen Y et al. "PTPsigma is a receptor for chondroitin sulfate proteoglycan, an inhibitor of neural regeneration", Science, 2009 Oct. 23; 326(5952):592-6); (i) myelin-associated glycoprotein (MAG); (j) oligodendrocytes; (k) oligodendrocyte-myelin glycoprotein; and (l) Reticulon-4, also known as Neurite outgrowth inhibitor or Nogo, which is a protein that in humans is encoded by the RTN4 gene (see, e.g., Lynda J.-S. Yang et al., "Axon regeneration inhibitors, Neurological Research, 1 Dec. 2008, Volume 30, Issue 10, pp. 1047-1052) (m) ethanol or glycerol.

Further examples of anti-regeneration agents include agents that induce the formation of the inhibitory scar tissue, which may be selected from the following, among others: (a) laminin, fibronectin, tenascin C, and proteoglycans, which have been shown in inhibit axon regeneration (see, e.g., Stephen J. A. Davies et al., "Regeneration of adult axons in white matter tracts of the central nervous system," Nature 390, 680-683 (18 Dec. 1997); (b) reactive astrocyte cells, which are the main cellular component of the glial scar, which form dense web of plasma membrane extensions and which modify extracellular matrix by secreting many molecules including laminin, fibronectin, tenascin C, and proteoglycans; (c) molecular mediators known to induce glial scar formation including transforming growth factor.beta. (TGF.beta.) such as TGF.beta.-1 and TGF.beta.-2, interleukins, cytokines such as interferon-.gamma. (IFN-.gamma.), fibroblast growth factor 2 (FGF2), and ciliary neurotrophic factor; (d) glycoproteins and proteoglycans that promote basal membrane growth (see, e.g., C C Stichel et al., "The CNS lesion scar: new vistas on an old regeneration barrier", Cell Tissue Res. (October 1998) 294 (1): 1-9); and (e) substances that deactivate Schwann cells. Still other examples of anti-regeneration agents include Semaphorin-3A protein (SEMA3A) (which may be used to induce the collapse and paralysis of neuronal growth cones) to block regeneration is incorporated into the hydrogels to release approximately 1 μg per day for a total of 2 μg over a couple weeks, calcium (which may lead to turning of nerve growth cones induced by localized increases in intracellular calcium ions), f) inhibitory dyes such as methylene blue, and g) radioactive particles. Yet other inhibitory drugs include ciguatoxins, anandamide, HA-1004, phenamil, MnTBAB, AM580, PGD2, topoisomerase I inhibitor (10-HCT), anti-NGF, and anti-BDNF.

Pain and inflammation. The media may additionally include one or more agents intended to relieve pain in the short-term post-procedure timeframe where increased pain over baseline may be experienced due to local tissue reaction depending upon the ablation procedure. Examples of suitable anesthetic agents that can be incorporated into the hydrogel for this purpose include, for instance, bupivicaine, ropivicane, lidocaine, or the like, which can be released to provide short-term local pain relief post-procedure around the treatment region Inflammation and scar tissue in the surrounding tissue can also be minimized with the incorporation of methylprednisolone into the hydrogel.

Growth permissive form. Regarding the examples of FIGS. 5A-5E in some instances, it is desirable to provide a growth-permissive substance between the proximal and distal stump of the nerve to encourage nerve regeneration rather than growth inhibition. In some embodiments, the growth permissive substance simply provides a temporary barrier to the growth inhibitory gel leaking into the anastomoses site or damaged nerve tissue and inhibiting regeneration. In other embodiments, the growth permissive substance provides a medium through which nerves can regenerate without the need for autograft/allograft or conduit/wrap.

In accordance with a further aspect of the invention, there are provided methods and devices to encourage guided nerve growth, such as to span a gap between two opposing nerve stumps and restore nerve function or to fill a small gap between nerves that have been directly coapted with sutures. The method may comprise the steps of placing a first nerve end and a second nerve end in a first form cavity; Introducing an in situ forming growth permissive media into the cavity and into contact with the first nerve end and the second nerve end to form a junction; the media changing from a flowable to a nonflowable state. The nerves, coupled together by the in situ formed media, are then removed from the first form cavity and placed inside a second larger form cavity; and Introducing a growth inhibitory media into the second form cavity to encapsulate the junction. The growth inhibitory media changes from a flowable to a nonflowable state, covering the nerves and the growth permissive media; The second form is then removed and discarded. In another embodiment, the first and/or second forms remain in place.

There is also provided a formed-in-place nerve regeneration construct, comprising a growth permissive hydrogel bridge having first and second ends and configured to span a space between two nerve ends and encourage nerve regrowth across the bridge; and a growth inhibiting hydrogel jacket encapsulating the growth permissive hydrogel bridge and configured to extend beyond the first and second ends of the growth permissive region to directly contact the proximal and distal nerves, respectively. In yet another embodiment, growth permissive media is delivered into an inhibitory form cavity where it undergoes a change from a substantially flowable to a nonflowable state. The form remains in place and provides acts as a growth inhibitory substrate through which nerves cannot regenerate.

Preferably, the growth permissive media is comprised of an in situ forming gel, such as a hydrogel and the growth inhibitory media is comprised of an in situ forming gel, such as a hydrogel. However, the growth permissive media may be comprised of an in situ forming gel and the form into which it is delivered is comprised of an ex vivo crosslinked gel.

In some embodiments it is desirable that the growth permissive hydrogel adheres to the nerve tissue, providing a method to anastamose the tissue without the need for sutures. In doing so, the nerve-growth permissive gel-nerve unit can be picked up and handled as one continuous nerve unit, permitting their later placement of the unit in a growth inhibitory hydrogel. In other embodiments, the growth permissive hydrogel can provide a temporary glue lasting approximately half an hour. The glue is strong enough to lightly adhere the two nerves but has comparable mechanical strength to e.g. fibrin glue.

Tensionless repair. Another advantage of in situ forming hydrogels is that they can be designed to provide tensionless repair of nerves. In one embodiment, the wrap form of the conduit is deep enough such that the directly repaired/anastamosed nerve ends are placed in the form with the repaired region detensioned inside the form. When the hydrogel is formed around the detensioned nerve, the nerve-nerve repair is not under tension; any tension is carried by the hydrogel around it. In this manner, the nerves are not under tension and the hydrogel carries the load in a more evenly distributed way than a suture repair can.

In another embodiment, tensionless repair is additionally provided by the growth inhibitory hydrogel. In this embodiment, the proximal and distal nerves are placed in the conduit and the growth inhibitory hydrogel is delivered at the nerve-conduit interface to prevent nerves from escaping out of the conduit and tethering with the surrounding scar tissue. In another embodiment, the nerves are purposefully detensioned within the growth permissive hydrogel, by creating slack in the nerves within the form. In cases where the nerves are directly reanastamosed, care is taken to make sure that the tension, if any, is at the interface between the nerve and the entrance to the form on either side of the wrap form, and that the nerve inside the wrap is slack or free of tension before applying the growth permissive hydrogel prescursor solution into the wrap. In this manner, the nerve anastomoses, nerve-gel-nerve or nerve-nerve interface is without tension. In the preferred embodiment, the nerve-growth-permissive hydrogel-nerve unit sits entirely within the cavity of the second nerve form. The delivery of the inhibitory hydrogel provides additional protection and detensioning, providing approximately 3 to 10 mm of circumferential coverage around the nerve on either side of the injury.

Coverage. In one embodiment, the growth permissive media is located substantially in between the two nerve ends and does not appreciably cover the outer surface of the nerves. Thus, the diameter of the growth permissive media closely approximates that of the diameter of the nerve. As a result of the location of the growth permissive media, the growth inhibitory media is delivered around the external or epineurial surface of the proximal and distal nerves as well as the growth permissive media, covering preferably 10 mm or 5 mm of more of healthy nerve on either side. This permits the guidance of nerves directly from the proximal nerve stump into the distal nerve stump. The additional coverage provides adhesion strength and protection from aberrant nerve outgrowth at the junction of the proximal nerve-gel.

Color. In one embodiment, the growth permissive hydrogel is one color, such as blue, and the growth inhibitory hydrogel has no color. In another embodiment the growth permissive hydrogel is blue and the growth inhibitory hydrogel is green or turquoise.

Preferably, the growth permissive substance is an in situ forming hydrogel. Preferably, the growth permissive substance contains growth inhibitory and growth permissive microdomains. Nerves will naturally pathfind along the growth inhibitory domains and within the growth permissive domains. Growth permissive hydrogels leveraging the in situ forming PEG platform are desirable. These hydrogels may be crosslinked chemically or using photo-crosslinkable approaches as with the non-growth permissive hydrogels described above. The in situ growth permissive hydrogels are preferably more rapidly degrading than the growth inhibitory hydrogels, encouraging cellular ingrowth and replacement of the synthetic matrix with natural extracellular matrix. As a result, preferred PEG hydrogels for these applications are formed through the crosslinking of PEG-NHS esters with hydrolytically labile ester bonds (PEG-SS, PEG-SG, PEG-SAZ, PEG-SAP), preferably PEG-SS. These PEGs can be crosslinked with PEG-amines or trilysines, for example.

Other hydrogels may be selected to provide non-growth permissive zones of the growth permissive hydrogel including PEG-PPO-PEG, PEG-polyesters (triblocks, deblocks), alginate, agar, and agarose. Other synthetic hydrogels include PEG-poly(amido amine) hydrogels, PEO, PVA, PPF, PNIPAAm, PEG-PPO-PEO, PLGA-PEG-PLGA, poly (aldehyde guluronate), or polyanhydrides. An extensive list of hydrogel matrices that may be adapted for in situ formation is found in Hoffman (2012) Hydrogels for biomedical applications. Advanced Drug Delivery Reviews, 64: 18-24, incorporated herein for reference. Another soft hydrogel that may be suitable includes the InnoCore Liquid Polymer (LQP) (PCLA-PEG-PCLA) which is a liquid polymer which forms a soft macroscopic depot after delivery in vivo and degrades slowly over a period of two to three moths. Another potentially suitable hydrogel includes a six-armed shar-shaped poly(ethylene oxide-stat-propylene oxide) with acrylate end groups (star-PEG-A) can be photocured. Other start-shaped PEGs include a 6-arm or 8-arm NHS ester PEGs include mPEG-SCM (PEG-NHS: Succinimidly Carboxyl Methy elster) and mPEG-SG (PEG-NHS: Succinimidly Glutarate ester), PEG-co-poly(lactic acid)/poly(trimethylene carbonate), PEG-NHS and trilysine, PEG-NHS and PEG-thiol, PEG-NHS and PEG-amine, PEG-NHS and albumin, Dextran aldehyde and PEG-amine functionalized with tris (2 aminoethyl) amine. PEG concentration. If PEG is used in the growth permissive matrix, preferably the PEG concentration in these hydrogels is preferably between 3 and 8%, more preferably 3 to 5 wt % for the applications to support nerve extension.

In some embodiments, the growth permissive region is directly conjugated or chemically linked to the non-growth permissive hydrogel region. For example, chitosan may be coupled to the inhibitory region. The chitosan may be a 100 kDa to 350 kDa molecular weight, more preferably 130 kDa to 160 kDa with a 0.85 degree of deacetylation. In another embodiment, an interpenetrating network of gelatin methacrylamide polymerized with a PEG famework.

Alternative growth permissive matrices. In addition to incorporating positively charged matrix components that encourage glial invasion, cellular division, and three-dimensional cellular organization, the growth permissive components can also support nerve ingrowth with or without the presence of supporting cells. These growth promoting substances are applied at a concentration sufficient to support growth but not at such a high concentration to impact the mechanical properties of the hydrogel. Growth permissive hydrogels contain combinations of natural growth promoting biomaterials such as natural polymers collagen type I (0.01 to 5 wt %, preferably 0.3-0.5 wt %, 1.28 mg/ml), laminin (4 mg/ml), hyaluronic acid, fibrin (9 to 50 mg/ml, strength 2.1 kPa) or synthetic/semi synthetic polymers such as poly-L-arginine or poly-L-lysine (0.001-10 wt %). By combining the growth inhibitory domains above with the growth permissive matrices, growth supportive matrices can be formed. These blends support the 1) creation of a path through which regenerating nerves can path find, 2) provide a substrate to which neurites can adhere and Schwann cells can migrate in. In one embodiment the hydrogel is 8-arm 15K PEG-succinimidyl succinate (PEG-SS) crosslinked with trilysine, containing 5 wt % collagen. In another embodiment, the hydrogel comprises an 4% PEG (4-arm 10K PEG-SG crosslinked with 4-arm 20K PEG-amine) containing 0.01% poly-L-lysine. By reducing the concentration of the crosslinked PEG solution relative to the growth inhibitory PEGs used in neuroma blocking applications and increasing the concentration of the positively charged growth permissive biomaterial, an in situ forming hydrogel can be created with both inhibitory and permissive domains to encourage nerve outgrowth.

In another example, a non-growth permissive hydrogel (e.g. crosslinked PEG hydrogel, alginate, methacryloyl-substituted tropoelastin MeTro hydrogel) may be blended with a growth permissive hydrogel (e.g. fibrin gelatin-methacryloyl GelM, GelM/PEG or GelMA/MeTro composites) Soucy et al (2018) Photocrosslinable Gelatin-Tropoelastin Hydrogel Adhesives for Peripheral Nerve Repair, Tissue Engineering, PMID: 29580168. Incorporation of polylysine. Polylysine—either the D,L, or L forms, can be incorporated into the growth permissive hydrogel region. For example Epsiliseen (Siveele, Epsilon-poly-L-lysine). The growth permissive hydrogel may be an in situ forming hydrogel comprising chitosan and poly-lysine (https://pubs.acs.org/doi/10.1021/acs.biomac.5b01150). The growth permissive hydrogel may be an in situ forming hydrogel comprising PEG and polylsyine (http://pubs.acs.org/doi/abs/10.1021/bm201763n).

PEG+Collagen in Backbone. Alternatively, natural polymers, such as type I collagen, can be crosslinked with PEG hydrogel (e.g. 8-arm 15K SG) with collagen concentrations ranging from 30 to 60 mg/ml and PEG concentration at 50 or 100 mg/ml ((Sargeant et al 2012. An in situ forming collagen-PEG hydrogel for tissue regeneration. Acta Biomaterialia 8, 124-132 and Chan et al (2012) Robust and semi-interpenetrating hydrogels from PEG and Collagen for Elastomeric Tissue Scaffolds. 12(11) 1490-1501.

Other gels. In yet another embodiment, the first growth permissive material may comprise a viscous solution, a nanoparticle- or microparticle-based gel, a slurry, or a macrogel. In one embodiment a fibrin glue can be delivered around nerves. In another embodiment, the solution is a slurry of biocompatible nanoparticles or microparticles through which nerves can regenerate. In another embodiment, a microgel or modugel is delivered to the site. Microgels are created for stable dispersions with uniform size, large surface area through precipitation polymerization. Modugels, scaffolds formed from microgels, properties can be varied through the degree of crosslinking and scaffold stiffness (Preparation of the gels, including PEG-based hydrogels, can be found in Scott et al (2011) Modular Poly (ethylene glycol) scaffolds provide the ability to decouple the effects of stiffness and protein concentration on PC12 cells. Acta Biomater 7(11) 3841-3849, incorporated herein for reference.) In addition, the use of electrically conductive hydrogels, such as piezoelectric polymers like polyvinvylidene fluoride (PVDF) which generates transient surface charges under mechanical strain, may be beneficial in supporting the growth of nerves through the hydrogel. For example, dendrimers comprised of metabolites such as succinic acid, glycerol, and beta-alanine may be incorporated into the hydrogels to encourage extracellular matrix infiltration (Degoricija et al (2008) Hydrogels for Osteochondral Repair Based on Photocrosslinkable Carbamate Dendrimers, Biomacromolecules, 9(10) 2863.

Plain natural hydrogels. In another embodiment, an entirely growth permissive hydrogel is provided without growth inhibitory microdomains. In one embodiment, a fibrin hydrogel (such as those crosslinked with thrombin) with a lower linear compressive modulus is selected. Numerous other biomaterials have also been demonstrated to support nerve regeneration in 2D and 3D scaffolds and include chitosan, chitosan-coupled alginate hydrogels, viscous fibronectin, collagen type I (~1.2 mg/ml), assist in regeneration, fibrin (9 to 50 mg/ml),fibronectin, laminin (https://www.ncbi.nlm.nih.gov/pubmed/15978668)), Puramatrix, heparin sulfate proteoglycans, hyaluronic acid (1% sodium hyaluronate viscous solution), polylysine (poly (D, or L, or D,L) lysine), xyloglucan, polyornithine, agarose (0.5% to 1% w/v) and blends of these materials. Additional growth permissive hydrogels include thermosensitive hydrogels like chitosan-beta-glycerophosphate hydrogels (C/GP) mixtures. Other thermosensitive hydrogels include poly (N-isopropylacrylamide) (PNIPAAM). In one embodiment, a poly(propylene fumarate) PPF can be injected as a liquid and chemically, thermally, or photo cross-linked in situ to form a gel to provide a growth supportive hydrogel.

In another embodiment, an interpenetrating network of HA and photocrosslinkable glycidyl methacrylate hyaluronic acid (GMHA) provides a growth permissive substrate. Other growth permissive hydrogels include: crosslinked hyaluronic acid gel (Hyaloglide gel) or ADCON-T/N gel (Gliatech). These materials may be physically or covalently crosslinked. Other scaffold materials may be anticipated for the growth permissive region (https://www.ncbi.nlm.nih.gov/pmc/articles/PMC5899851/).

Charge. It is well known in the art that nerves prefer to grow on or through positive charged surfaces. In some embodiments, the positive charges are incorporated into the polymer backbone. In other embodiments, these charges are incorporated in other components, such as extracellular matrix proteins that become trapped in the hydrogel when it forms in situ.

Incorporation of Adjuvants. In some embodiments, anti-inhibitory molecules can be incorporated into the hydrogel to improve the growth permissive environment, such as chondroitinase, which breaks down chondroitin sulfate proteoglycans (CSPGs). https://www.ncbi.nlm.nih.gov/pubmed/20620201 These may be incorporated with the polymer powder, diluent, or accelerator depending on the stability requirements of the adjuvant.

Incorporation of Lipid Domains. Lipid domains may be added to the backbone or side chains or these polymers to encourage nerve outgrowth. Hydrophobic domains may also be incorporated into the backbone of the hydrogel to support nerve ingrowth through soft and hard regions of the hydrogel. In one embodiment, lipids are added to diffuse between polymer chains and act as plasticizers for the polymeric material that facilitates chain moving and improves elasticity.

Adhesion strength. The growth permissive media and the growth inhibiting media may transform into hydrogels and have sufficient adherence that, once formed, the nerve ends can be picked up and handled with ease. The adhesive strength of the subsequently formed nonflowable growth permissive media, though, permits the nerve-gel-nerve unit to be picked up with forceps. The unit can be gently placed within a second form to permit circumferential delivery of the inhibitory hydrogel. The adhesion strength also permits good coupling between the nerve end and the hydrogel.

Stiffness. As matrix stiffness and compressive strength of the hydrogel play a significant role in promoting or inhibiting nerve regeneration, the mechanical properties of the growth inhibitory and growth permissive hydrogels differ substantially. The growth permissive hydrogel is significantly softer and less stiff to support and encourage the regeneration of nerve growth cones into the media. Gel stiffness (G*, dynes/sq cm) of the growth permissive hydrogel is preferably softer and more elastic in character with G* less than 800 dynes/sqcm, more preferably less than 200 dynes/sqcm. In some embodiments, regions of soft substrate (100-500 Pa) are placed adjacent to regions of stiffer substrate (1,000 to 10,000 Pa). The elasticity of this growth permissive substrate should preferably be less than 0.1-0.2 MPa, preferably less than 1.5 KPa. On the other hand, the growth inhibitory hydrogel provides the necessary mechanical strength to maintain the coupling and relationship between the proximal and distal nerve stumps, reduce or eliminate the need for suturing, and potentially permit tensionless repair. Nerve extension into the growth permissive matrix is strongly dependent on matrix stiffness, and pore interconnectivity of pores, charge. As the gel degrades, the nerve extension may also be impacted by the hydrolytic, oxidative, or enzymatic degradation of the matrix. For the growth permissive hydrogel, the stiffness of the gel should more closely approximate the elastic modulus of the nerve tissue, at or below 1 kPa, preferably 200-300 Pa. Swelling. Given the placement of the growth inhibitory hydrogel around the growth permissive hydrogel, the growth permissive hydrogel swelling must be less than or equal to the swelling of the growth inhibitory hydrogel. Alternatively, the growth permissive hydrogel must be sufficiently soft that it does not have the strength to push on the growth inhibitory hydrogel. Porosity. In some embodiments, the growth permissive media comprises a growth inhibitory hydrogel filled with highly interconnected macroscopic growth permissive pores that provide a channel through which regenerating nerves can pathfind. Pores may created in the hydrogels through porogen leaching (solid, liquid), gas foaming, emulsion-templating to generate macroporosity. The pores may be created by a growth permissive porogen and/or contain therapeutic agents or simply be filled with saline. The pores may be created by phase separation during hydrogel formation. The average pore size, pore size distribution, and pore interconnections are difficult to quantify and therefore are encompassed in a term called tortuosity. Preferably, the hydrogel is a macroporous hydrogel with pores greater than 1 µm, more preferably greater than 10 µm, preferably between >100 µm more preferably >150 µm, with an average pore radius of 0.5 to 5%. The density of the pores should be greater than 60%, or preferably greater than 90% pore volume, of sufficient density that the pores are interconnected. In this manner, the remaining PEG hydrogel provides a non-growth permissive scaffold through which neurons can grow. In one embodiment, porosity is created by creating air or nitrogen bubbles in the hydrogel through shaking, pushing the plunger in the applicator back and forth, or introducing the air through another port in the applicator. In another embodiment, a surfactant is used as an air-trapping agent to create porosity in the hydrogel, such as sodium dodecyl sulfate (SDS). In situ gas foaming with up to 60% porosity and 50 to 500 micron pores and a compressive modulus of 20-40 Mpa, described in https://www.ncbi.nlm.nig.gov/pmc/articles/PMC3842433/. In another embodiment, the creation of a foaming agent which generates macroscale pores to permit cellular migration and proliferation. In some embodiments, the porogen is a degradation enhancer. Preferably, the concentration of pores is sufficient that the pores are interconnected with one another. Preferably, >70% of the pores are interconnected, more preferably 80% or more. The pores create and define growth permissive zones and preferably the interconnectivity is sufficiently high that the tortuoisity is low that neves will extend out into them. In addition, if the walls of the pores are formed of PEG, nerves can pathfind along the walls of the hydrogel. Pores may be created by low molecular weight end-capped PEGs, such as PEG 3350, which can be delivered in up to 50 wt % solution. The growth permissive regions or pores may contain natural biomaterials such as collagen/gelatin, chitosan, hyaluronic acid, laminin (Matrigel), fibrin that provide a growth permissive substrate for nerve outgrowth.

Channels. In another embodiment, channels are created in the hydrogel in situ to permit nerve guidance. In one embodiment, channels are approximately 150 µm, 300 µm in diameter, more preferably 500 µm in diameter to 1 mm. Preferably, the channels are filled with saline in situ.

Fibers and other structural elements. Adding fibers or structural elements (e.g. beads, macrospheres, gel particle slurry, microspheres, rods, nanoparticles, liposomes, rods, filaments, sponges) to reinforce the structural integrity of the hydrogel, improve the hydrogels in vivo persistence and/or to provide a substrate along which neurites can extend and growth for guidance, is desirable. The nanofibers can be flexible or rigid and can range in size from nanometers to micrometers in diameter, and can be linear or irregularly shaped. In the preferred embodiment, the fiber deposition through the needle containing the media into the form permits the generally longitudinal parallel alignment of the fibers within the conduit. The fiber-loaded media is laid down in the conduit by first filling the distal end and advancing the needle to proximal end of the form in a smooth continuous motion while depositing the hydrogel. Rapid gelation (less than 20 seconds, preferably less than 10 seconds, more preferably less than 7 seconds) permits the fibers to be captured in the desired orientation as the media changes to a nonflowable form. In another embodiment, the media solutions is more viscous, between 10 and 20 cP, permitting the suspension of these fibers within the growth permissive media. In another embodiment, the fibers are provided in the kit and are placed in the lumen with forceps.

Fibers, rods, filaments, sponges. In another embodiment, the fibers are added to the form either immediately before or after the delivery of the growth permissive hydrogel solution in the wrap form to provide a surface along which nerves can grow en route to the distal stump. The fibers may be added using forceps, another syringe, or sprinkling them within the conduit. The gelation time of the hydrogel media is sufficiently delayed that the fibers can be embedded within the media prior to the media change to a substantially nonflowable form.

Injecting nanorods Similarly, shorter nanorods may be incorporated into the polymer solution, polymer powder, diluent, or accelerator and then injected in situ. By injecting smoothly and in one direction and utilizing a fast gelling hydrogel, the alignment of these fibers may be improved. The fibers may be constructed from nondegradable or biodegradable materials. In some embodiments the fibers are made of chitosan, polycaprolactone, polylactic or glycolic acid, or combinations thereof. The fibers may be inert of functionalized with a positive charge or addition of a coating such as laminin. https://www.ncbi.nlm.nig.gov/pubmed/24083073. In another embodiment the fibers undergo molecular self-assembly to form a fiber or cable.

In one embodiment, fibers will be incorporated either randomly or in an aligned fashion in order to provide the support for nerve regeneration across a gel. Filaments and sponges can be formed out of collagen. Rods can be formed out of collagen-gag, fibrin, hyaluronic acid, polyamide, polyarylonitrile-co-methacrylate, PAN-MA, PGA, PHBV/PLGA blends, PLLA, PLGA or PP. The filaments may be between 0.5 and 500 µm in diameter, more preferably 15 to 250 µm in diameter. In one embodiment, the rods, fibers, and filaments may be coated with laminin.

Nanofibers can be incorporated into the hydrogel to provide structural support. Fibers may be composed of PEG, PGA, PLA, PCL, PCL mixed with gelatin, PCL with a laminin coating, chitosan, hyaluronic acid, gels, hyaluronan, fibrin, or fibrinogen (10 mg/ml). In one embodiment, a fibrillar fibrin hydrogel (AFG), or P(D,L, LA) fibers, fabricated through electrospinning is are incorporated into in situ forming gels. (Electrospinning methods are described in McMurtrey (2014) Patterned and functionalized nanofiber scaffolds in three-dimensional hydrogel constructs enhance neurite outgrowth and functional control. J. Neural Eng 11, 1-15, incorporated herein.) In another embodiment, polyethylene glycol is incorporated as a porogen and nanofibers, such as cellulose nanofibers, are employed to provide structural integrity to the soft porous hydrogel (Naseri et al (2016) 3-Dimensional Porous Nanocomposite Scaffolds Based on Cellulose Nanofibers for Cartilage Tissue Engineering: Tailoring of Porosity and Mechanical Performance. RSC Advances, 6, 5999-6007, incorporated for reference herein.)

Microparticles. In yet another embodiment, microparticles, nanoparticles or micelles can be introduced into the growth permissive media to deliver drugs to the nerve tissue. In one embodiment, microparticles are composed of PEG hydrogels (e.g. 8-arm 15K SG, 10%), poly(D,lysine) microparticles. For example, cross-linked PEG particles formed ex vivo can be formulated into a slurry lubricated by low MW PEG (1-6%, 12 kDa). Alternatively, the particles can be suspended in a collagen or hyaluronic acid solution to provide a growth permissive matrix through which the nerves can regenerate. Similarly, hydrophobic particles and oils may be incorporated to create growth permissive voids in the hydrogel to encourage nerve outgrowth.

Compressive modulus of growth promoting hydrogels. Matching the compressive modulus of the nervous tissue to the growth permissive hydrogel may also be advantageous—approximately 2.6 to up to 9.2 kPa (Seidlits et al (2010) The effects of hyaluronic acid hydrogels with tunable mechanical properties on neural progenitor cell differentiation are promising (Biomaterials 31, 3930-3940). Similarly, the linear compressive modulus is less than 20 kPa, preferably less than 10 kPa, more preferably less than 1 kPa to encourage nerve and Schwann cells ingrowth into the gel.

In situ forming growth-permissive hydrogels that can be delivered in a wrap form or thin layer around partially transected, compressed, or completely transected nerve ends are desirable. The use of an in situ forming gel eliminates the need to transect otherwise largely intact nerves and provides a mechanism to support nerve regeneration through a substrate and into the distal tissue. Coupling the growth-permissive hydrogel with a growth-inhibitory hydrogel assists in guiding and directing these neurites within the growth permissive region. In one embodiment, the in situ forming hydrogel has sufficient adhesive strength and stiffness that it can be delivered between the nerve stumps into an appropriate form and then be picked up and removed from the first wrap form and placed into a second larger wrap form into which the growth inhibitory in situ forming hydrogel is delivered.

Hydrogel thickness. Growth permissive gel. The thickness or diameter of the growth permissive gel should roughly approximate the diameter of the nerves to which it is being delivered. In the case where only a small defect exists in the nerves, the growth permissive gel can be dropped directly on the injured tissue to form a thin layer. Growth inhibitory gel. Given the often rigorous environment in which a nerve is located, often in a fascial plain between or along muscles, in some embodiments it is desirable that a minimum thickness of growth inhibitory hydrogel be maintained around the nerve, preferably 1 mm circumferentially, more preferably 2-3 mm. For example, for a form that would be place around the common digital nerve, approximately 2-2.5 mm in diameter, a conduit of approximately 3 to 4 mm in diameter is used, providing a 0.5 to 2 mm hydrogel layer around the nerve. For the digital nerve, approximately 1 to 1.5 mm, a conduit approximately 2 to 2.5 mm in diameter is selected. For larger nerves embedded in the arm or thigh, between 2 and 10 mm, preferably the gel thickness is 2 to 6 mm, preferably 2 to 3 mm around the nerve circumferentially.

Gelation time. After 30 seconds or less, preferably 20 seconds or less, more preferably 10 seconds or less, more preferably 3 to 7 seconds, the hydrogel forms around the nerve. The hydrogel is transparent so the location of the nerve can be visually confirmed in the hydrogel. The clinician visually or mechanically confirms the hydrogel formation and the silicone form is slipped off of the hydrogel cap and discarded. See FIG. 2. The surrounding tissues (muscles, skin) are then sutured up again per standard surgical technique.

In Vivo Persistence of Growth Permissive Gel or Slurry. The in vivo persistence may be considerably less in the growth permissive hydrogel than the growth inhibitory gel, permitting the progressive invasion by Schwann cells and regenerating nerve fibers. For growth permissive hydrogels, more rapidly degrading hydrogel networks are desirable to permit cellular infiltration and subsequent nerve regeneration. Preferably, the hydrogels should degrade in between 2 months and 6 months, more preferably 3 months. Degradation of the inhibitory region. The inhibitory guide preferably remains in place for 1 month or more, more preferably 3 months or more, to provide support to the regenerating nerve. In some embodiments, the degradation of the growth permissive hydrogel is days to months, preferably days to weeks, permitting the clearance of the material as the cellular tissue replaces and regenerates.

Charge. Preferably, the growth permissive hydrogels are positive charged or contain positively charged domains. Addition of PEG fusogens. In some embodiments, it may be desirable to add a nonreactive fusogen to the hydrogel formulation. Thus, in addition to the mechanical blocking properties of the hydrogel, the damaged proximal surviving nerves may be protected from excitotoxic damage and their membranes resealed. Furthermore, the hyperexcitability of the cell bodies is reduced, such as the dorsal root ganglia, reducing neuropathic paresthesia and dysthesia accompanying nerve injury. In one embodiment, low molecular weight end-capped or nonreactive PEG (methoxy-PEG) to the formulation. For example, the trilysine buffer may contain nonreactive low molecular weight linear PEG (0.2 kDa, 2 kDa, 3.35 kDa, 4 kDa, or 5 kDa). When mixed with the 8-arm 15K star-shaped PEG, the resulting hydrogel will have low molecular weight PEG (2 kDa, 10-50% w/v) which may help to seal up the damaged nerve endings and thus further reduce the influx and efflux of ions. In this manner, lysosome formation, demyelination, and and other membrane debris can be prevented from accumulating at the site. In another embodiment, cyclosporin A may be applied with the solution to improve the survival of the ablated axons.

In another embodiment, six-armed star-shaped end-capped PEG (poly(ethylene-oxide-stat-propylene oxide) or star-PEG-OH) can be added as the fusogen. The linear PEG that is mixed in the polymer blend can diffuse out of the crosslinked network, creating micropores up to one micron in diameter, facilitating diffusion of nutrients but not neurite extension. The linear PEG based hydrogels are more stiff than the star-PEG based fusogen addition. The addition of the linear PEG is based on findings which had been demonstrated 2 kDa PEG to be beneficial in rapidly restoring axonal integrity, called 'PEG-fusion' between nerves of cut- and crushed-axons (Britt et al 2010, J. *Neurophysiol,* 104: 695-703). The theory is that this is in part because of sealing of the plasmalemmal and axolemma at the lesion site.

Reapplying or repositioning. Should the clinician not be happy with the location of the nerve, the hydrogel 'cap' can be removed with forceps and the procedure repeated. Nerve sparing. In yet another embodiment, it may be desirable to deliver the in situ forming hydrogel around a nerve in order to reduce the handling of the nerve during a procedure. By delivering it in and around the nerve bundle, the hydrogel can set and prevent forceps or any other micromanipulators from crushing it during the procedure. In additional to protecting the nerve from mechanical damage, the hydrogel may also protect from thermal damage such as through cauterizing or RF ablation, cryoablation.

There are several embodiments where existing nerve wraps (e.g. conduits with a top slit in them that allow the nerve to be pushed into the semi-rigid wrap) and/or conduits are still desired but the physician would like to provide additional support for regeneration either in the form of the application of a growth permissive hydrogel, a growth inhibitory hydrogel, or the combination.

The form for the growth permissive hydrogel is designed to be substantially the same size as the nerves into which they are placed. In one embodiment, a silicon form which is a hemi-tube with an inner diameter approximately equivalent to the outer diameter of the nerves is selected. The nerve are placed in the form either in direct apposition, within close approximation, or, with a gap in order to prevent tension, so that they rest within the form without any tension. The nerves rest directly on the surface of the form itself for delivery of the growth permissive hydrogel.

Drugs to Promote Nerve Regeneration. Drugs may be delivered to the nerve directly prior to the placement of the form. For example, local anesthetic, anti-inflammatory, growth factors agents may be delivered directly to the nerve prior to encapsulation with the hydrogel. Alternatively, drugs may be incorporated directly into the hydrogel or incorporated through encapsulation in drug-loaded microspheres, micelles, liposomes, or free-base to achieve an improved sustained release profile.

Drugs for pain relief. In some embodiments, drugs used for the treatment of chronic neuropathic pain may be delivered in the hydrogels including tricyclic antidepressants, selective serotonin and noradrenaline reuptake inhibitors, antiepileptics, and opioids. For example, pregabalin and gabapentin may be selected for their analgesic properties. Similarly, duloxetine, vennlafaxine, the SNRI inhibitor and combinations thereof to provide more comprehensive pain relief. Anti-inflammatories such as diclofenac may also be promising. Other potential targets include ligands for the FK506-binding protein family, neuroimmunophilin ligands, which are neuritotrophic, neuroprotective and neuroregenerative agents.

The local delivery of taxol and cetuximab have also shown promise for improving the survival and regeneration of neurons and may be suitable for stimulating nerve regeneration when delivered locally in an in situ forming hydrogel. In another embodiment, cyclic AMP (cAMP) or cAMP analogue dibutyryl cAMP promotes regeneration of nerves and may be incorporated into an in situ forming hydrogel to promote nerve regeneration after injury. In another embodiment, Kindlin-1 and Kindlin-2 (fermitin family) and drugs which bind to the integrin superfamily of cell surface receptors, allow nerves to extend across inhibitory matrix and can be incorporated into the hydrogels to enhance regeneration across inhibitory extracellular matrix.

In another embodiment, tacrolimus (FK506), an immunosuppressant, may be incorporated into the hydrogel to enhance axon generation and speed. The final concentration of FK506 in the formed hydrogel is 100 ug/ml to 10 mg/ml, more preferably 0.1 mg/ml. The drug is released for weeks to months, preferably at least a month, more preferably at least 3 months to aid in immunosuppression and enhance nerve outgrowth. Drugs include FK506, drugs selective for selective inhibition of FKBP12 or FKBP51.

Drugs that are P2X receptor antagonists (P2XR), P2X3 receptor antagonists (e.g. AF-219 Gefapivant, AF-130), P2X4 and P2X7 receptor antagonists that are implicated in visceral and neuropathic pain (as well as migraine and cancer pain), are of interest. P2X7 Receptor Antagonists. The purinergic receptor antagonist Brilliant Blue G (BBG) and the structurally similar analogue, Brilliant Blue FCF (BB FCF), are of particularly interest for their ability to modulate the nerve environment after injury (Wang et al. 2013. The food dye FD&C Blue No. 1 is a selective inhibitor of the ATP release channel Panx1. J. Gen. Physiol. 141(5) 649-656)). Other dyes of interest include the FD&C Green No. 3 dye which, like BBG and BB FCF, inhibit the ATP release Pannexin1 channel with an IC50 between 0.2 and 3 uM. A structurally similar analogue, Brilliant Blue FCF (BB FCF) otherwise known as FD&C #1 (https://pubchem.ncbi.nlm.nih.gov/compound/Acid_Blue_9), has also been demonstrated to improve nerve survival and regeneration after injury when used in combination with a low molecular weight end capped PEG 3350 Da (https://www.ncbi.nlm.nig.gov/pubmed/23731685). Similar efficacy has been demonstrated using BBG in rat models of sciatic nerve crush (Ribeiro et al 2017) and ischemia in the myenteric plexus (Palombit et al 2019). In addition, BBG is thought to have anti-inflammatory and anti-nociceptive effects through reducing high extracellular ATP concentrations and high calcium influxes after nerve damage. In one embodiment, Brilliant Blue FCF is incorporated into the in situ forming hydrogel. The dye can be incorporated into the polymer vial, the diluent, or the accelerator solutions to yield a final concentration in the gel of 0.0001 to 5%, preferably 0.001 to 0.25%, more preferably 0.01 to 0.02% wt % or approximately 1 to 1000 ppm, preferably 10 to 100 ppm. On a per site anatomic basis, local doses of between 5 μg to as high as 25 mg of dye may be delivered in a hydrogel locally. For example, the FD&C #1 dye may be delivered at 0.01% concentration in the hydrogels to reduce neuronal injury after stroke (Arbeloa et al 2012—Referenced in Palmobit et al 2019). By incorporating the dye into the hydrogel, the dye may help improve the survival of the transected axons, reduce the local inflammation while the hydrogel provides a barrier to regeneration.

In another embodiment, TRPV1 agonists, such as capsaicin are delivered to the nerve to deliver a preconditioning injury to the nerve that in term results in a neuroregenerative response downstream to enhance nerve regeneration (PMID: 29854941). In one embodiment, capsaicin loaded hydrogels (1 to 8 wt % drug loading) are delivered percutaneously to intact nerves to reduce painful diabetic neuropathy). In another embodiment, pifithrin-u or acetyl-L-carnitine is delivered in the hydrogel to reduce and treat chemotherapy-induced peripheral neuropathy (CIPN) by reducing neuronal mitochondrial damage.

In another embodiment, drugs that block the deregulated long non-coding RNAs may also be incorporated into the hydrogels, such as targets of endogenous Kcna2 antisense RNA. In one embodiment, mitomycin C is incorporated into the in situ forming hydrogel in order to inhibit Schwann cell proliferation and stimulate apoptosis in fibroblasts. In one embodiment, 0.1 to 5 mg mitomycin C are loaded into the polymer powder and utilized to form an in situ formed gel with 0.01-0.5 wt % mitomycin C releasing between 0.1 and 0.5 mg/ml are released per day, preferably for 7 days or more. In still another embodiment, Rho Kinase (ROCK)

inhibitors or ROK antagonists or Rac1 antagonists may be incorporated, such as ripasudil hydrochloride.

Additional drugs include the anti-inflammatory curcurmin, rapamycin, paclitaxel, cyclosporin A, pyrimidine derivatives (RG2 and RG5) to stimulate remyelination, Axon guidance molecule Slit 3, triptolide, KMUP-1. calcium modulating agents including calcitonin, calcium antagonist nifedipine, nimodipine, nerve growth factor (NGF, 500 ng), insulin-like growth factor (IGF-1), thymoquinone, duloxetine (10-30 mg), melatonin, c-Jun or mTORC1 agonists may help support Schwann cell differentiation and nerve remyelination, nicotine, and adrenomedullin—used as a neuroprotective and neurotrophic drug.

Example 1. Growth inhibitory hydrogel. Into the vial containing 80 mg PEG with NHS ester reactive group, 80 µg of BB FCF is added to yield a 0.1% dye concentration in the PEG hydrogel.

Example 2. Growth inhibitor hydrogel with a fusogen. Into the vial containing 80 PEG with NHS ester reactive group, 80 µg of BB FCF and 500 mg PEG 3350.

Example 3. Phospholipids are incorporated into the PEG hydrogel, such as cephalin, to improve fusion. Phospholipids are surface active amphiphilic molecules and can be incorporated as an emulsifier, wetting agent, solubilizer, and membrane fusogen. These may include phosphatidylcholine, phosphatidylethanolamine or phosphatidylglycerol (https://www.ncbi.nlm.nig.gov/pmc/articles/PMC4207189/, incorporated for reference herein).

Example 4. In some embodiments, hydrogels are loaded with amiodarone with or without the addition of ethanol. For example, 0.1 to 5 wt % loading of amiodarone or more can be achieved. This can also be accomplished and improved with the incorporation of ethanol into the solution. For example, 50 to 75% ethanol can be incorporated with 0.25 wt % amiodarone to achieve burst release of amiodarone between 3 to 5 days. Similarly, 1% amiodarone can be delivered from the hydrogels for a period of 30-60 days.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Furthermore, various theories and possible mechanisms of actions are discussed herein but are not intended to be limiting.

What is claimed is:

1. A method of in situ formation of a nerve cap, the method comprising the steps of:
   identifying a severed end of a nerve;
   positioning the severed end into a cavity defined by a form;
   introducing media into the cavity to surround the severed end; and
   permitting the media to undergo a transformation from a first, relatively flowable state to a second, relatively non flowable state to form a protective barrier surrounding the severed end; wherein the transformation occurs within about 10 seconds of the introducing step; wherein the form is composed of a nondegradable material that can be removed from the surgical site after the media is transformed to the second, relatively non flowable state to form the protective barrier surrounding the severed end.

2. A method of in situ formation of a nerve cap as in claim 1, further comprising the step of removing the form.

3. A method of in situ formation of a nerve cap as in claim 1, comprising identifying a surgically severed nerve.

4. A method of in situ formation of a nerve cap as in claim 1, wherein the form comprises a nerve guide, and said positioning step comprises positioning the nerve such that the nerve guide maintains the severed end within the cavity spaced apart from a sidewall of the form.

5. A method of in situ formation of a nerve cap as in claim 4, comprising positioning the severed end between 0.1 mm and 2 mm away from the sidewall.

6. A method of in situ formation of a nerve cap as in claim 1, additionally comprising the step of blotting a volume of axoplasm from the severed nerve prior to the introducing step.

7. A method of in situ formation of a nerve cap as in claim 1, wherein the transformation comprises a crosslinking or polymerizing.

8. A method of in situ formation of a nerve cap as in claim 1, wherein the transformation produces a synthetic crosslinked hydrogel protective barrier.

9. A method of in situ formation of a nerve cap as in claim 1, wherein the form comprises a first configuration in which the cavity is exposed, and a second configuration in which the cavity is covered; and further comprising the step of advancing the form from the first configuration to the second configuration prior to the introducing media step.

10. A method of in situ formation of a nerve cap as in claim 1, wherein the form comprises a first configuration in which the cavity is exposed and a second configuration in which the cavity is covered, and wherein the step of positioning the severed end comprises advancing the form from the first configuration to the second configuration prior to introducing media into the cavity.

11. A method of in situ formation of a nerve cap as in claim 1, wherein the protective barrier has an in vivo persistence of at least about two months.

12. A method of in situ formation of a nerve cap as in claim 1, wherein the transformation causes the media to swell in volume within a range of from about 2% to about 30%.

13. A method of in situ formation of a nerve cap as in claim 1 further comprising the step of positioning the form at a treatment site before the positioning the severed end step.

14. A method of in situ formation of a nerve cap as in claim 1 further comprising the step of forming the form in situ before the positioning the severed end step.

15. A method of in situ formation of a nerve cap as in claim 1 further comprises delivering the media around the nerve in two successive steps.

16. A method of in situ formation of a nerve cap as in claim 1, wherein the form contains an integral post for seating the nerve.

17. A method of in situ formation of a nerve cap as in claim 1, wherein the form has a clamshell lid.

18. A method of in situ formation of a nerve cap as in claim 1, wherein the viscosity of the flowable media is between 300 cP to 70,000 cP.

* * * * *